United States Patent
Kim et al.

(10) Patent No.: US 10,011,595 B2
(45) Date of Patent: Jul. 3, 2018

(54) ETHYLDIAMINE OREXIN RECEPTOR ANTAGONISTS

(71) Applicant: Merck Sharp & Dohme Corp., Rahway, NJ (US)

(72) Inventors: Ronald M. Kim, Summit, NJ (US); Scott D. Kuduk, Harleysville, PA (US); Nigel Liverton, Harleysville, PA (US); Gang Zhou, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/532,602

(22) PCT Filed: Dec. 14, 2015

(86) PCT No.: PCT/US2015/065454
§ 371 (c)(1),
(2) Date: Jun. 2, 2017

(87) PCT Pub. No.: WO2016/100161
PCT Pub. Date: Jun. 23, 2016

(65) Prior Publication Data
US 2017/0355692 A1    Dec. 14, 2017

Related U.S. Application Data

(60) Provisional application No. 62/094,616, filed on Dec. 19, 2014.

(51) Int. Cl.

| | | |
|---|---|---|
| C07D 213/84 | (2006.01) | |
| C07D 239/42 | (2006.01) | |
| C07D 401/12 | (2006.01) | |
| C07D 401/14 | (2006.01) | |
| C07D 403/12 | (2006.01) | |
| C07D 403/14 | (2006.01) | |
| C07D 405/12 | (2006.01) | |
| C07D 413/12 | (2006.01) | |
| A61K 31/44 | (2006.01) | |
| A61K 31/4439 | (2006.01) | |
| A61K 31/506 | (2006.01) | |

(52) U.S. Cl.
CPC ......... *C07D 413/12* (2013.01); *C07D 213/84* (2013.01); *C07D 239/42* (2013.01); *C07D 401/12* (2013.01); *C07D 401/14* (2013.01); *C07D 403/12* (2013.01); *C07D 403/14* (2013.01); *C07D 405/12* (2013.01)

(58) Field of Classification Search
None
See application file for complete search history.

(56) References Cited

U.S. PATENT DOCUMENTS

| | | |
|---|---|---|
| 7,951,797 B2 | 5/2011 | Breslin et al. |
| 8,242,121 B2 | 8/2012 | Coleman et al. |
| 8,263,586 B2 | 9/2012 | Cox et al. |
| 8,349,872 B2 | 1/2013 | Coleman et al. |
| 8,357,700 B2 | 1/2013 | Cox et al. |
| 8,357,709 B2 | 1/2013 | Coleman et al. |
| 8,362,009 B2 | 1/2013 | Bergman et al. |
| 8,399,494 B2 | 3/2013 | Bergman et al. |
| 8,466,281 B2 | 6/2013 | Coleman et al. |
| 8,618,102 B2 | 12/2013 | Coleman et al. |
| 8,623,863 B2 | 1/2014 | Coleman et al. |
| 8,669,272 B2 | 3/2014 | Breslin et al. |
| 8,685,961 B2 | 4/2014 | Brashear et al. |
| 8,710,076 B2 | 4/2014 | Breslin et al. |
| 8,940,898 B2 | 1/2015 | Kuduk et al. |
| 9,029,364 B2 | 5/2015 | Kuduk et al. |
| 9,156,819 B2 | 10/2015 | Kuduk et al. |
| 9,546,152 B2 | 1/2017 | Kuduk et al. |
| 9,550,786 B2 | 1/2017 | Cooke et al. |
| 9,556,145 B2 | 1/2017 | Kuduk et al. |
| 9,556,190 B2 | 1/2017 | Kuduk et al. |
| 9,586,934 B2 | 3/2017 | Kuduk et al. |
| 9,586,950 B2 | 3/2017 | Kuduk et al. |
| 9,617,246 B2 | 4/2017 | Kuduk et al. |

(Continued)

FOREIGN PATENT DOCUMENTS

| | | |
|---|---|---|
| WO | WO2008147518 A1 | 12/2008 |
| WO | WO2016069510 | 5/2016 |

(Continued)

OTHER PUBLICATIONS

Zipp et al. Bioorganic & Medicinal Chemistry Letters 24 (Jul. 2014) 3886-3890.*

(Continued)

*Primary Examiner* — Emily Bernhardt
(74) *Attorney, Agent, or Firm* — J. Eric Thies; John C. Todaro

(57) ABSTRACT

The present invention is directed to ethyldiamne compounds which are antagonists of orexin receptors. Such compounds are of the general structural formula I:

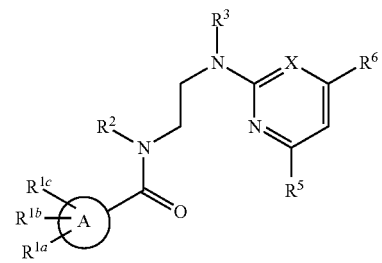

The present invention is also directed to uses of the compounds described herein in the potential treatment or prevention of neurological and psychiatric disorders and diseases in which orexin receptors are involved. The present invention is also directed to pharmaceutical compositions comprising these compounds. The present invention is also directed to uses of these compositions in the potential prevention or treatment of such diseases in which orexin receptors are involved.

10 Claims, No Drawings

(56) References Cited

U.S. PATENT DOCUMENTS

| | | |
|---|---|---|
| 9,624,197 B2 | 4/2017 | Kuduk et al. |
| 2004/0176443 A1 | 9/2004 | Bakthavatchalam et al. |
| 2006/0258672 A1* | 11/2006 | Barbosa ............... C07D 239/42 |
| | | 514/253.01 |
| 2010/0029736 A1 | 2/2010 | Cox et al. |
| 2011/0195957 A1 | 8/2011 | Bergman et al. |
| 2011/0201591 A1 | 8/2011 | Bergman et al. |
| 2011/0201632 A1 | 8/2011 | Breslin et al. |
| 2012/0196901 A1 | 8/2012 | Coleman et al. |
| 2015/0322039 A1 | 11/2015 | Kuduk et al. |
| 2015/0322040 A1 | 11/2015 | Kuduk et al. |
| 2015/0322041 A1 | 11/2015 | Kuduk et al. |
| 2016/0016935 A1 | 1/2016 | Kuduk et al. |
| 2016/0068510 A1 | 3/2016 | Kuduk et al. |
| 2016/0068514 A1 | 3/2016 | Kuduk |
| 2016/0102073 A1 | 4/2016 | Kuduk et al. |
| 2016/0176858 A1 | 6/2016 | Liverton et al. |
| 2016/0185768 A1 | 6/2016 | Liverton et al. |
| 2016/0304490 A1 | 10/2016 | Kuduk et al. |
| 2016/0318900 A1 | 11/2016 | Kuduk et al. |
| 2016/0318923 A1 | 11/2016 | Kuduk et al. |

FOREIGN PATENT DOCUMENTS

| | | |
|---|---|---|
| WO | WO2016069512 | 5/2016 |
| WO | WO2016069515 | 5/2016 |
| WO | WO2016069517 | 5/2016 |
| WO | WO2016069519 | 5/2016 |
| WO | WO2016085783 | 6/2016 |
| WO | WO2016085784 | 6/2016 |
| WO | WO2016089721 | 6/2016 |
| WO | WO2016089722 | 6/2016 |
| WO | WO2016100154 | 6/2016 |
| WO | WO2016100156 | 6/2016 |
| WO | WO2016100157 | 6/2016 |
| WO | WO2016100161 | 6/2016 |
| WO | WO2016100162 | 6/2016 |
| WO | WO2016106105 | 6/2016 |
| WO | WO2016106106 | 6/2016 |

OTHER PUBLICATIONS

Anthony J. Roecker et al, Orexin Receptor Antagonists: New Therapeutic Agents for the Treatment of Insomnia, Journal of Medicinal Chemistry, 2016, 504-530, 59(2).

Jason W. Skudlarek et al, Investigation of orexin-2 selective receptor antagonists: Structural modifications resulting in dual orexin receptor antagonists, Bioorganic & Medicinal Chemistry Letters, 2017, 1364-1370, 27(6).

* cited by examiner

ETHYLDIAMINE OREXIN RECEPTOR ANTAGONISTS

CROSS REFERENCE TO RELATED APPLICATIONS

This application is a U.S. National Phase application under 35 U.S.C. § 371 of PCT Application No. PCT/US2015/065454, filed Dec. 14, 2015, which claims priority under 35 U.S.C. § 119(e) from US Application No. 62/094,616, filed Dec. 19, 2014.

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable of binding OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to ethyldiamine compounds which are antagonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

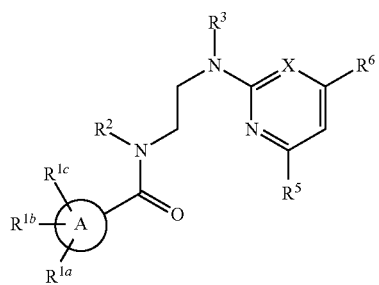

wherein:
A is selected from the group consisting of phenyl, naphthyl and heteroaryl;
X is N or CH;
each of $R^{1a}$, $R^{1b}$ and $R^{1c}$ is independently selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one to three substituents independently selected from $R^4$,
(5) —(C=O)$_m$—O$_n$—C$_{3-6}$cycloalkyl, where the cycloalkyl is unsubstituted or substituted with one to three substituents independently selected from $R^4$,
(6) —(C=O)$_m$—C$_{2-4}$alkenyl, where the alkenyl is unsubstituted or substituted with one to three substituents independently selected from $R^4$,
(7) —(C=O)$_m$—C$_{2-4}$alkynyl, where the alkynyl is unsubstituted or substituted with one to three substituents independently selected from $R^4$,
(8) —(C=O)$_m$—O$_n$-phenyl or —(C=O)$_m$—O$_n$-naphthyl, where the phenyl or naphthyl is unsubstituted or substituted with one to three substituents independently selected from $R^4$,
(9) —(C=O)$_m$—O$_n$-heterocycle, where the heterocycle is unsubstituted or substituted with one to three substituents independently selected from $R^4$,
(10) —(C=O)$_m$—NR$^{10}$R$^{11}$, wherein $R^{10}$ and $R^{11}$ are independently selected from the group consisting of:
(a) hydrogen,
(b) C$_{1-6}$alkyl, which is unsubstituted or substituted with $R^4$,
(c) C$_{3-6}$alkenyl, which is unsubstituted or substituted with $R^4$,
(d) C$_{3-6}$alkynyl, which is unsubstituted or substituted with $R^4$,
(e) C$_{3-6}$cycloalkyl which is unsubstituted or substituted with $R^4$,
(f) phenyl, which is unsubstituted or substituted with $R^4$, and
(g) heterocycle, which is unsubstituted or substituted with $R^4$,
(11) —S(O)$_2$—NR$^{10}$R$^{11}$,
(12) —S(O)$_q$—R$^{12}$, where q is 0, 1 or 2 and where $R^{12}$ is selected from the definitions of $R^{10}$ and $R^{11}$,
(13) —CO$_2$H,
(14) —CN, and
(15) —NO$_2$;
$R^2$ is C$_{1-6}$alkyl, which is which is unsubstituted or substituted with halo, C$_{3-6}$cycloalkyl or phenyl;
$R^3$ is C$_{1-6}$alkyl, which is which is unsubstituted or substituted with halo or hydroxyl;
$R^4$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH$_2$,
(8) —NH—C$_{1-6}$alkyl,
(9) —NO$_2$,
(10) phenyl,
(11) heterocycle,

(12) —CO₂H, and
(13) —CN;
R⁵ is selected from the group consisting of:
(1) hydrogen,
(2) halogen,
(3) —CN,
(4) $C_{1-6}$alkyl, which is unsubstituted or substituted with halogen, hydroxyl or phenyl,
(5) —O—$C_{1-6}$alkyl, which is unsubstituted or substituted with halogen or phenyl,
(6) —O—$C_{3-6}$cycloalkyl, which is unsubstituted or substituted with $C_{1-6}$alkyl, halogen or phenyl, and
(7) —(C=O)—O—$C_{1-6}$alkyl;
R⁶ is selected from the group consisting of:
(1) hydrogen,
(2) halogen,
(3) —CN,
(4) $C_{1-6}$alkyl, which is unsubstituted or substituted with halogen, hydroxyl or phenyl,
(5) —O—$C_{1-6}$alkyl, which is unsubstituted or substituted with halogen or phenyl,
(6) —O—$C_{3-6}$cycloalkyl, which is unsubstituted or substituted with $C_{1-6}$alkyl, halogen or phenyl, and
(7) —(C=O)—O—$C_{1-6}$alkyl;
or a pharmaceutically acceptable salt thereof.

An embodiment of the present invention includes compounds of the formula Ia:

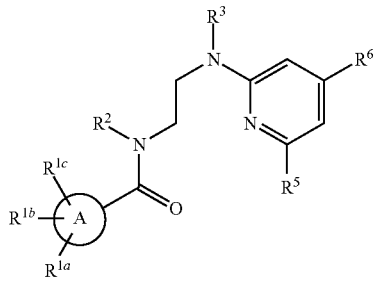

Ia wherein A, $R^{1a}$, $R^{1b}$, $R^{1c}$, $R^2$, $R^3$, $R^5$ and $R^6$ are defined herein; or a pharmaceutically acceptable salt thereof.

An embodiment of the present invention includes compounds of the formula Ia':

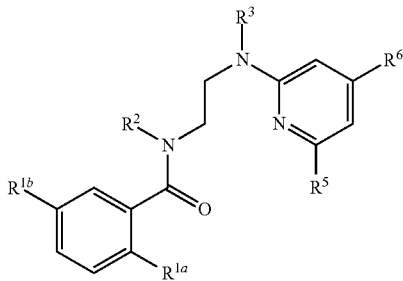

Ia' wherein $R^{1a}$, $R^{1b}$, $R^2$, $R^3$, $R^5$ and $R^6$ are defined herein; or a pharmaceutically acceptable salt thereof.

An embodiment of the present invention includes compounds of the formula Ia":

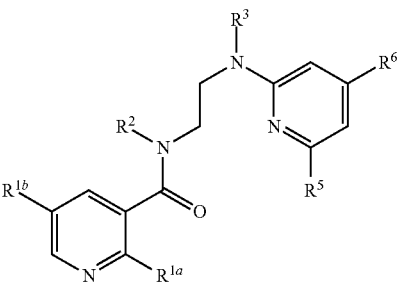

Ia"

wherein $R^{1a}$, $R^{1b}$, $R^2$, $R^3$, $R^5$ and $R^6$ are defined herein; or a pharmaceutically acceptable salt thereof.

An embodiment of the present invention includes compounds of the formula Ib:

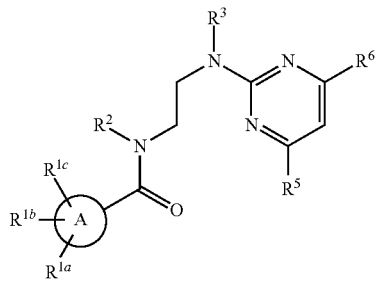

Ib wherein A, $R^{1a}$, $R^{1b}$, $R^{1c}$, $R^2$, $R^3$, $R^5$ and $R^6$ are defined herein; or a pharmaceutically acceptable salt thereof.

An embodiment of the present invention includes compounds of the formula Ib':

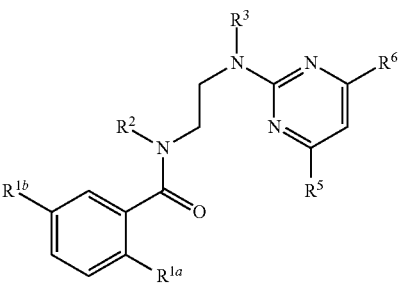

Ib' wherein $R^{1a}$, $R^{1b}$, $R^2$, $R^3$, $R^5$ and $R^6$ are defined herein; or a pharmaceutically acceptable salt thereof.

An embodiment of the present invention includes compounds of the formula Ib":

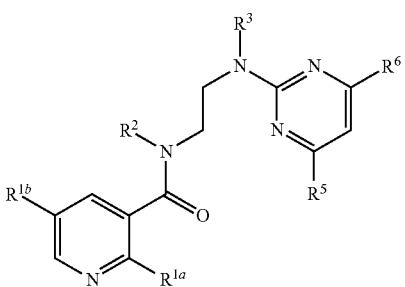

wherein $R^{1a}$, $R^{1b}$, $R^2$, $R^3$, $R^5$ and $R^6$ are defined herein; or a pharmaceutically acceptable salt thereof.

An embodiment of the present invention includes compounds wherein A is selected from phenyl, pyridyl, thiophenyl, thiazolyl, isothiazolyl, and pyrazolyl. An embodiment of the present invention includes compounds wherein A is phenyl. An embodiment of the present invention includes compounds wherein A is pyridyl. An embodiment of the present invention includes compounds wherein A is thiophenyl. An embodiment of the present invention includes compounds wherein A is thiazolyl. An embodiment of the present invention includes compounds wherein A is isothiazolyl. An embodiment of the present invention includes compounds wherein A is pyrazolyl.

An embodiment of the present invention includes compounds wherein X is N. An embodiment of the present invention includes compounds wherein X is CH.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or —$NO_2$,
(7) phenyl, which is unsubstituted or substituted with halogen, hydroxyl, $C_{1-6}$alkyl, —O—$C_{1-6}$alkyl or —$NO_2$,
(8) —O-phenyl, which is unsubstituted or substituted with halogen, hydroxyl, $C_{1-6}$alkyl, —O—$C_{1-6}$alkyl or —$NO_2$,
(9) —CN, and
(10) —NH—$C_{1-6}$alkyl, or —N($C_{1-6}$alkyl)($C_{1-6}$alkyl), which is unsubstituted or substituted with halogen, hydroxyl, $C_{1-6}$alkyl, and —O—$C_{1-6}$alkyl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) —CN, and
(7) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or —$NO_2$.

An embodiment of the present invention includes compounds wherein $R^{1a}$, $R^{1b}$ and $R^{1c}$ are independently selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen,
(5) —CN, and
(6) heteroaryl, wherein heteroaryl is selected from imidazolyl, indolyl, oxazolyl, pyridyl, pyrrolyl, pyrimidinyl, tetrazolyl, and triazolyl.

An embodiment of the present invention includes compounds wherein $R^{1c}$ is hydrogen, and $R^{1a}$ and $R^{1b}$ are independently selected from the group consisting of:
(1) hydrogen,
(2) fluoro,
(3) chloro,
(4) bromo,
(5) methyl,
(6) ethyl,
(7) methoxy,
(8) trifluoromethyl, and
(9) heteroaryl, wherein heteroaryl is selected from imidazolyl, indolyl, oxazolyl, pyridyl, pyrrolyl, pyrimidinyl, tetrazolyl, and triazolyl.

An embodiment of the present invention includes compounds wherein $R^{1c}$ is hydrogen, and $R^{1a}$ and $R^{1b}$ are independently selected from the group consisting of:
(1) hydrogen,
(2) fluoro,
(3) chloro,
(4) methyl,
(5) methoxy,
(6) tetrazolyl, and
(7) triazolyl.

An embodiment of the present invention includes compounds wherein $R^2$ is selected from the group consisting of:
(1) methyl,
(2) ethyl,
(3) n-propyl,
(4) iso-propyl, and
(5) n-butyl.

An embodiment of the present invention includes compounds wherein $R^2$ is ethyl.

An embodiment of the present invention includes compounds wherein $R^3$ is selected from methyl and ethyl. An embodiment of the present invention includes compounds wherein $R^3$ is methyl.

An embodiment of the present invention includes compounds wherein $R^5$ is selected from the group consisting of:
(1) hydrogen,
(2) halogen,
(3) $C_{1-6}$alkyl, which is unsubstituted or substituted with halogen or hydroxyl,
(4) —O—$C_{1-6}$alkyl, which is unsubstituted or substituted with halogen, and
(5) —(C=O)—O—$C_{1-6}$alkyl.

An embodiment of the present invention includes compounds wherein $R^5$ is selected from the group consisting of:

(1) hydrogen,
(2) methyl,
(3) —C(CH$_3$)$_2$OH,
(4) —CH(OH)CF$_3$,
(5) —CH(OH)CH$_3$,
(6) —C(OH)(CF$_3$)CH$_3$, and
(7) —C(=O)OCH$_3$.

An embodiment of the present invention includes compounds wherein R$^5$ is selected from the group consisting of:
(1) hydrogen,
(2) methyl, and
(3) —C(CH$_3$)$_2$OH.

An embodiment of the present invention includes compounds wherein R$^6$ is selected from the group consisting of:
(1) hydrogen,
(2) —CN, and
(3) C$_{1-6}$alkyl.

An embodiment of the present invention includes compounds wherein R$^6$ is selected from the group consisting of: hydrogen, —CN, and methyl.

An embodiment of the present invention includes compounds wherein R$^5$ is hydrogen and R$^6$ is —CN. An embodiment of the present invention includes compounds wherein R$^5$ is methyl and R$^6$ is methyl. An embodiment of the present invention includes compounds wherein R$^5$ is —C(CH$_3$)$_2$OH and R$^6$ is hydrogen or methyl. An embodiment of the present invention includes compounds wherein R$^5$ is —C(CH$_3$)$_2$OH and R$^6$ is hydrogen. An embodiment of the present invention includes compounds wherein R$^5$ is —C(CH$_3$)$_2$OH and R$^6$ is methyl.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, C$_{1-6}$, as in C$_{1-6}$alkyl is defined to identify the group as having 1, 2, 3, 4, 5 or 6 carbons in a linear or branched arrangement, such that C$_{1-6}$alkyl specifically includes methyl, ethyl, n-propyl, iso-propyl, n-butyl, iso-butyl, tert-butyl, pentyl, and hexyl. Substituents (such as R$^{1a}$, R$^{1b}$ and R$^{1c}$) may be absent if the valency of the group to which they are attached does not permit such substitution. A group which is designated as being independently substituted with substituents may be independently substituted with multiple numbers of such substituents. The term "heteroaryl" as used herein includes benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

The present invention is also directed to the use of the compounds disclosed herein as antagonists of orexin receptor activity. The subject compounds and pharmaceutically acceptable salts thereof are useful in a method of antagonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for antagonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to antagonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% CO2) in 60 µl assay buffer containing 1 µM Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 min and finally 25 µl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in antagonizing the human orexin-2 receptor in the aforementioned assays with an IC50 of about 0.1 nM to 1500 nM. All of the final compounds of the following examples had activity in the FLIPR assay with an IC50 of about 5 nM to 500 nM against the orexin-2 receptor. Additional data is provided in the following Examples. Such a result is indicative of the intrinsic activity of the compounds in use as antagonists of orexin-1 receptor and/or the orexin-2 receptor. In general, one of ordinary skill in the art would appreciate that a substance is considered to effectively antagonize the orexin receptor if it has an IC50 of less than about 50 µM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. Generally, dosage levels of between 0.0001 to 10 mg/kg. of body weight daily are administered to the subject, e.g., humans and elderly humans, to obtain effective antagonism of orexin receptors. The dosage range will generally be about 0.5 mg to 1.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, omortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB 1 receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) 03-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)]NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; $GABA_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, such as suvorexant, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-azabenzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; MTBE: methyl tert-butyl ether; $NaHCO_3$: sodium bicarbonate; NaOH: sodium hydroxide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully under-

INTERMEDIATES

Intermediate A

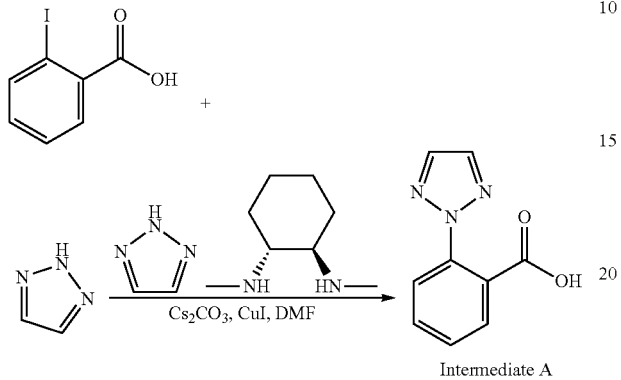

Intermediate A

2-(2H-1,2,3-Triazol-2-yl)benzoyl acid

A solution of 2-iodobenzoic acid (3.0 g, 12.09 mmol) in DMF (1.0 mL) was treated with 1,2,3-triazole (1.5 g, 21.7 mmol), copper(I) iodide (0.25 g, 1.2 mmol), $Cs_2CO_3$ (7.08 g, 21.7 mmol), and trans-N,N'-dimethylcyclohexane-1,2-diamine (0.31 g, 2.17 mmol). The mixture was heated at 120° C. for 12h. The reaction was cooled to rt, diluted with EtOAc, and filtered through Celite. The residue was purified by gradient elution on $SiO_2$ (0 to 10% MeOH in DCM with 0.1% AcOH) to give the title compound. HNMR (500 MHz, DMSO-$d_6$) δ 13.05 (br s, 1H), 8.12 (s, 2H), 7.81-7.52 (m, 4H) ppm. LRMS m/z (M+H) 190.2 found, 190.2.

Intermediate B

4-(Pyrimidin-2-yl)thiophene-3-carboxylic acid

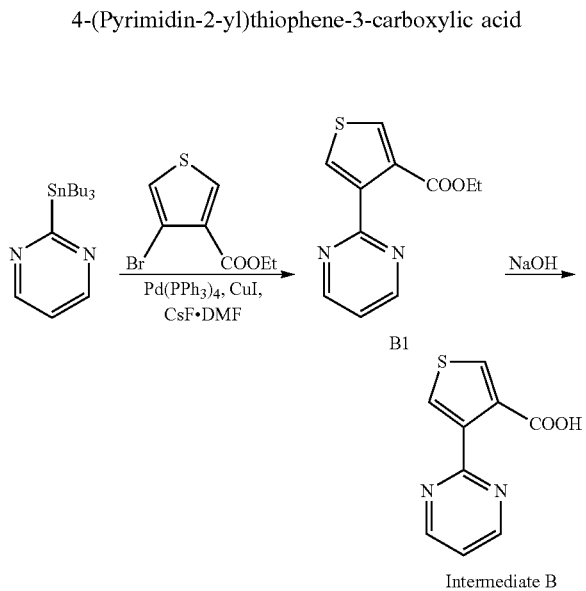

Intermediate B

Step 1: 4-Pyrimidin-2-yl-thiophene-3-carboxylic acid ethyl ester (B1)

To a degassed solution of 4-bromothiophene-3-carboxylic acid ethyl ester (1 g, 4.3 mmol), 2-tributylstannanylpyrimidine (1.587 g, 4.3 mmol) and CsF (1.3 g, 8.6 mmol) in DMF (5 mL) was added $Pd(PPh_3)_4$ (0.5 g, 0.43 mmol) and CuI (0.16 g, 0.86 mmol). The mixture was heated under microwave conditions at 110° C. for 45 minutes, cooled and diluted with saturated $NH_4Cl$ aqueous solution and water. The mixture was extracted with EtOAc (20 mL×5) and the combined organic layers were dried over $Na_2SO_4$, filtered. The filtrate was then concentrated in vacuo. The residue was purified by chromatography on silica gel (petroleum ether:EtOAc=10:1) to provide the title compound. LRMS m/z (M+H) 235.0 found, 235.0 required.

Step 2: 4-Pyrimidin-2-yl-thiophene-3-carboxylic acid (Intermediate B)

The title compound was prepared from the product of step 1 using the procedure described for the synthesis of compound F2. LRMS m/z (M+H) 207.0 found, 207.0 required.

Intermediate C

2-(2H-Tetrazol-2-yl)benzoic acid

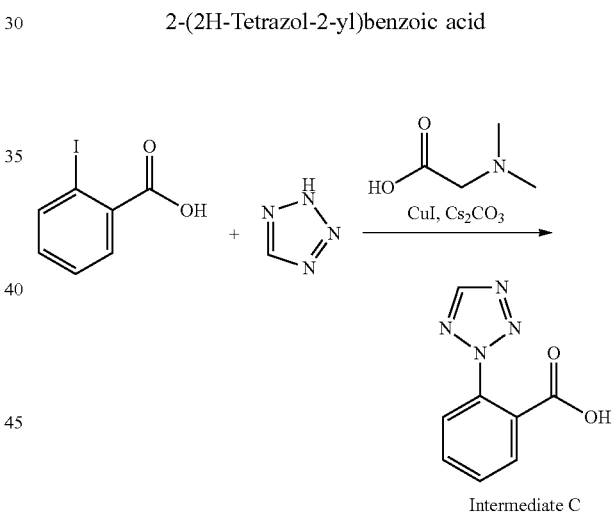

Intermediate C

To a 20 mL microwave tube was charged with 2-iodobenzoic acid (1.85 g, 7.46 mmol), cesium carbonate (4.06 g, 12.5 mmol), copper(I) iodide (0.128 g, 0.671 mmol), and DMA (8.0 mL). N,N'-Dimethylglyine (0.131 g, 1.27 mmol) and tetrazole (1.29 g, 18.4 mmol) were added, and the solution was irradiated in a microwave reactor at 100° C. for 1 hour. The reaction mixture was diluted with water and 1 N aqueous sodium hydroxide solution and extracted with EtOAc. The aqueous layer was acidified with conc. HCl and extracted 2× with EtOAc. The combined organic layers were washed with brine, dried over $MgSO_4$, filtered, and concentrated in vacuo. The residue was purified by silica gel chromatography [0-85% (1% acetic acid in EtOAc) in hexanes], to provide the title compound. $^1$H NMR (400 MHz, $CD_3OD$): δ 7.72-7.84 (m, 3 H), 8.07 (dd, J=7.6, 1.6 Hz, 1 H), 8.90 (s, 1 H) ppm. LRMS m/z (M+H) 191.1 found, 191.2.

Intermediate D

2-(2H)-1,2,3-Triazol-2-yl)thiophene-3-carboxylic acid

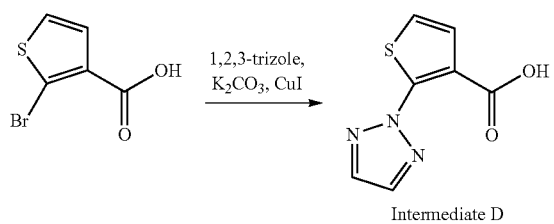 [SMILES: O=C(O)c1ccsc1Br ; O=C(O)c1ccsc1-n1nccn1]

Intermediate D

A solution of 2-bromo-3-thiophene carboxylic acid (1.50 g, 7.24 mmol), 1H-1,2,3-triazole (0.600 g, 8.69 mmol), potassium carbonate (2.00 g, 14.5 mmol), and copper(I) iodide (0.138 g, 0.724 mmol) in DMF (36.2 mL) was sparged with nitrogen and heated to 75° C. for 96 h. The cooled reaction mixture was diluted with water and washed with ether. The aqueous layer was acidified with conc. HCl. The acidic aqueous solution was extracted 3× with EtOAc and the combined organic fractions were washed with brine, dried over MgSO$_4$, filtered, and concentrated in vacuo. The crude material was purified by silica gel chromatography [0-70% (1% acetic acid in EtOAc) in hexanes] to provide the title compound. LRMS m/z (M+H) 196.2 found, 196.1 required.

Intermediate E

Potassium 2-(pyrimidin-2-yl)thiophene-3-carboxylate

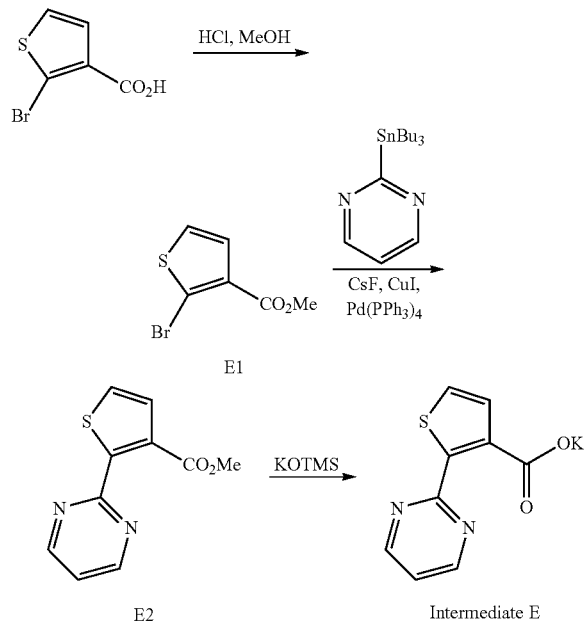

Step 1: Methyl 2-bromothiophene-3-carboxylate (E1)

A solution of 2-bromo-3-thiophene carboxylic acid (3.35 g, 16.2 mmol) in methanol (50 mL) was cooled to 0° C. and saturated with gaseous HCl. The solution was heated to 60° C. overnight, cooled and then concentrated in vacuo. The residue was re-dissolved in EtOAc, washed with saturated aqueous sodium bicarbonate and brine, dried over Na$_2$SO$_4$, filtered, and concentrated in vacuo to provide the title compound. LRMS m/z (M+H) 221.1 found, 221.0 required.

Step 2: Methyl 2-(pyrimidin-2-yl)thiophene-3-carboxylate (E2)

A solution of the product from step 1 (1.74 g, 7.87 mmol), 2-(tributylstannyl)pyrimidine (4.36 g, 11.81 mmol), CsF (4.78 g, 31.5 mmol), and copper(I) iodide (0.450 g, 2.36 mmol) in DMF (16 mL) in a pressure vessel was sparged with nitrogen and treated with Pd(PPh$_3$)$_4$ (0.455 g, 0.394 mmol). The mixture was sealed and heated at 120° C. overnight. The cooled reaction mixture was partitioned between EtOAc and water and filtered through celite. The organic layer was washed with saturated aqueous sodium bicarbonate and brine, dried over MgSO$_4$, filtered, and concentrated in vacuo. The residue was purified by silica gel chromatography (0-30% EtOAc in hexanes) to provide the title compound. LRMS m/z (M+H) 221.2 found, 221.1 required.

Step 3: Potassium 2-(pyrimidin-2-yl)thiophene-3-carboxylate (Intermediate E)

A solution of the product from step 2 (0.695 g, 3.16 mmol) and potassium trimethylsilanolate (0.506 g, 3.94 mmol) in THF (16 mL) was stirred at RT overnight, then diluted with ether and filtered through a glass frit. The solid was washed with ether and the filtrate was concentrated in vacuo to provide the title compound. LRMS m/z (M+H) 207.3 found, 207.1 required.

Intermediate F

4-(2H-1,2,3-Triazol-2-yl)thiophene-3-carboxylic acid

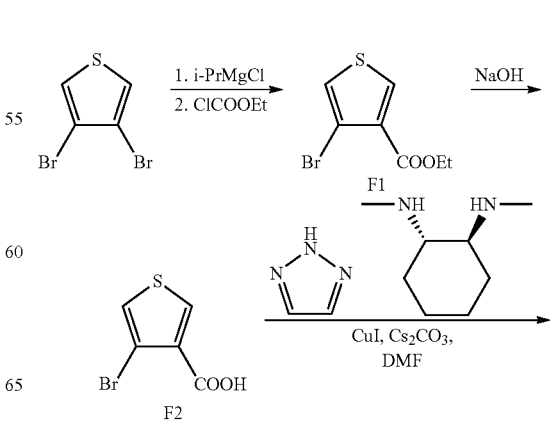

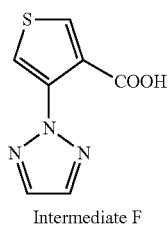

Intermediate F

Step 1: 4-Bromo-thiophene-3-carboxylic acid ethyl ester (F1)

To a solution of 3,4-dibromothiophene (30 g, 0.12 mol) in THF (200 mL) at 0° C. was added i-PrMgCl (2.0 M solution in THF, 77 mL, 0.15 mol) while maintaining the temperature below 5° C. The resulting mixture was stirred at 0-5° C. for 5 h. Then, ethyl chloroformate (14.4 mL, 0.15 mol) was added dropwise at while maintaining the temperature below 10° C. and the resulting mixture was warmed to RT, stirred overnight and quenched with the saturated aqueous $NH_4Cl$ solution. Most of the THF was then removed in vacuo, water was added and the mixture was extracted with EtOAc (80 mL×4). The combined organic layers were dried over $Na_2SO_4$, filtered. The filtrate was concentrated in vacuo and the crude product was purified by chromatography on silica gel (petroleumether:EtOAc=300:1) to provide the title compound.

Step 2: 4-Bromo-thiophene-3-carboxylic acid (F2)

To a solution of the product from step 1 (10 g, 43 mmol) in methanol (60 mL) was added sodium hydroxide (3.4 g, 86 mmol) and water (1 mL) and the mixture was stirred at RT overnight. The mixture was concentrated in vacuo and the residue was diluted with water (30 mL) and extracted with EtOAc (25 mL×4). The pH of aqueous layer was adjusted to ~3 with 1M HCl and extracted with EtOAc (25 mL×4). The combined EtOAc layers were dried over $Na_2SO_4$ and filtered. The filtrate was concentrated in vacuo to provide the title compound. LRMS m/z (M+H) 206.9, 208.9 found, 206.9, 208.9 required.

Step 3: 4-(2H-1,2,3-Triazol-2-yl)thiophene-3-carboxylic acid (Intermediate F)

To a mixture of the product from step 2 (7.9 g, 38 mmol), cesium carbonate (24.8 g, 76 mmol) and CuI (2.88 g, 7.6 mmol) in DMF (200 mL) were added 2H-[1,2,3]triazole (5.24 g, 76 mmol) and N,N'-dimethyl-cyclohexane-1,2-diamine (0.9 g, 6.5 mmol) and the mixture was heated to 110° C. overnight. The cooled reaction mixture was adjusted to ~pH=12 with 1M sodium hydroxide aqueous solution and extracted with EtOAc (50 mL×3). The aqueous layer was adjusted to ~pH=4 with 1M HCl aqueous solution and extracted with EtOAc (50 mL×4). The extracts was dried over $Na_2SO_4$, filtered. The filtrate was concentrated in vacuo and the residue was purified by chromatography on silica (petroleum ether:EtOAc=10:1) to provide the title compound. LRMS m/z (M+H) 196.0 found, 196.0 required.

Intermediate G 5-(2H-1,2,3-Triazol-2-yl)isothiazole-4-carboxylic acid

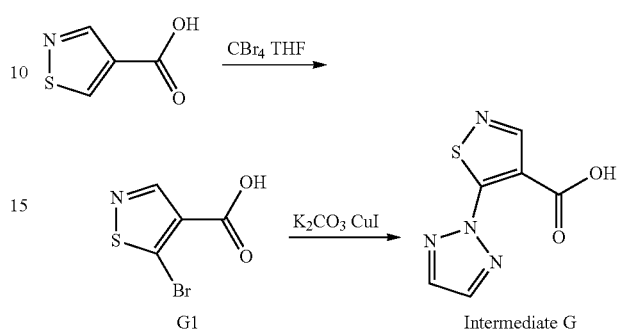

Step 1: 5-Bromo-isothiazole-4-carboxylic acid (G1)

To a solution of isothiazole-4-carboxylic acid (1.70 g, 12.98 mmol) in THF (17 ml) was added t-BuLi (29.95 mL) at −78° C., and then a solution of $CBr_4$ (8.62 g, 25.96 mmol) in THF (10 ml) was added dropwise. The mixture was stirred at −78° C. for 2 h, quenched with addition of saturated aqueous $NH_4Cl$ solution and extracted with EtOAc (50 mL×3). The aqueous layer was adjusted to ~pH=1.5 by addition of HCl and extracted with EtOAc (50 mL×3). The combined organic layers were dried over $MgSO_4$, filtered, and concentrated in vacuo to provide the title compound, which was used without further purification.

Step 2: 5-[1,2,3]Triazol-2-yl-isothiazole-4-carboxylic acid (Intermediate G)

To a solution of the product from step 1 (1.50 g, 7.25 mmol) in DMF (15 mL) were added potassium carbonate (2.00 g, 14.5 mmol), CuI (138 mg, 0.725 mmol) and 2H-1, 2, 3-triazole (0.6 g, 8.70 mmol) and the mixture heated at 110° C. for 16 h. The cooled reaction mixture was filtered and extracted with EtOAc (50 mL×3). The aqueous layer was adjusted to ~pH=1.5 by addition of HCl and extracted with EtOAc (50 mL×3). The combined organic layers were dried over $MgSO_4$, filtered, and concentrated in vacuo. The residue was purified by Prep-HPLC to provide the title compound.

Intermediate H

4-Fluoro-2-(2H-1,2,3-triazol-2-yl)benzoic acid

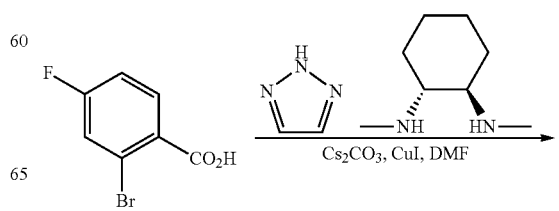

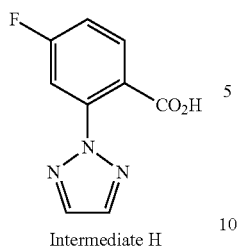

Intermediate H

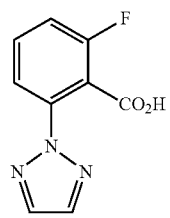

Intermediate I3

To a mixture of 2-bromo-4-fluorobenzoic acid (30 g, 137 mmol), cesium carbonate (89.26 g, 274 mmol) and CuI (5.27 g, 27.4 mmol) in DMF (200 mL) were added N,N'-dimethylcyclohexane-1,2-diamine (3.7 mL, 23.3 mmol) and 1H-1,2,3-triazole (18.92 g, 274 mmol). The resulting mixture was stirred at 110° C. overnight, cooled, concentrated in vacuo and diluted with water (150 mL). The aqueous mixture was extracted with EtOAc (300 mL×3). The aqueous layer was acidified with 2N HCl and extracted with EtOAc (300 mL×4). The combined organic layers were washed with brine (150 mL×3), dried over Na$_2$SO$_4$, filtered and the filtrate was concentrated in vacuo. The residue was purified by chromatography on silica gel (petroleumether: EtOAc=100:1~5:1) to provide the title compound. LRMS m/z (M+H) 208.0 found, 208.0 required.

Intermediates I1, I2, I3

3-Fluoro-2-(2H-1,2,3-triazol-2-yl)benzoic acid

5-Fluoro-2-(2H-1,2,3-triazol-2-yl)benzoic acid

6-Fluoro-2-(2H-1,2,3-triazol-2-yl)benzoic acid

Intermediates I1, I2, I3 were prepared in a similar manner to that described for Intermediate G, replacing 2-bromo-4-fluorobenzoic acid with the appropriate bromo or iodo substituted fluorobenzoic acids.

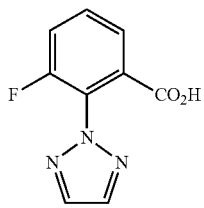

Intermediate I1

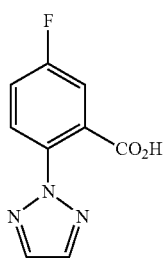

Intermediate I2

Intermediate J

5-Methyl-2-(2H-1,2,3-triazol-2-yl)thiophene-3-carboxylic acid

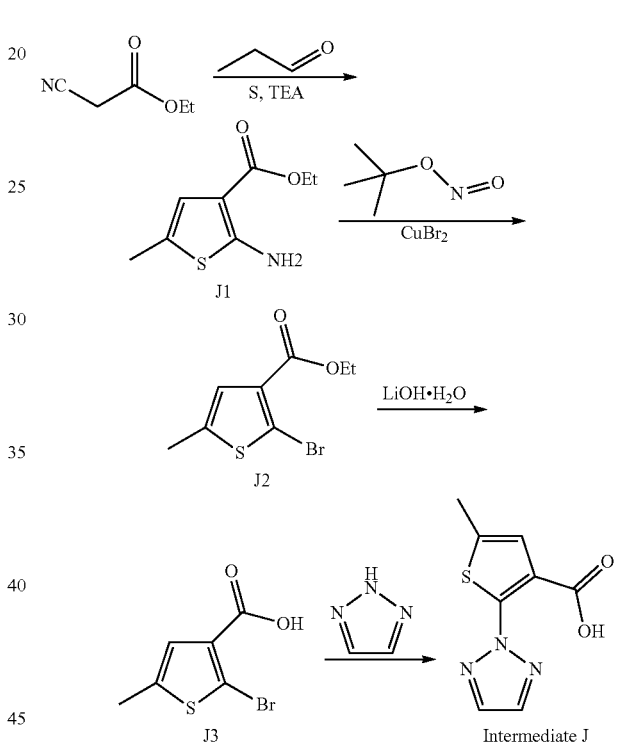

Step 1: Ethyl 2-amino-5-methylthiophene-3-carboxylate (J1)

A mixture of ethyl 2-cyanoacetate (9.7 g, 90 mmol), TEA (5.15 g, 51 mmol) and sublimed sulfur in DMF (30 mL) was stirred at 15° C. for 15 mins. Propionaldehyde (5.0 g, 90 mmol) was added dropwise. The reaction mixture was stirred for 3 hours, diluted with EtOAc (70 mL), and filtered. The filtrate was washed with water, brine, dried over MgSO$_4$, filtered, and concentrated in vacuo. The residue was purified by chromatography on silica (petroleum ether: EtOAc=10:1 to 1:1) to give the title compound. LCMS m/z (M+H) 186.2 found, 186.1 required.

Step 2: Ethyl 2-bromo-5-methylthiophene-3-carboxylate (J2)

A mixture of tert-butyl nitrite (6.67 g, 64.8 mmol) and CuBr$_2$ in acetonitrile (80 mL) was stirred at 0° C. for 30 mins and a solution of the product from step 1 (6.0 g, 32.4 mmol) in acetonitrile (100 mL) was added dropwise. The reaction mixture was stirred for 4 h, diluted with EtOAc (70 mL), washed with water and brine, dried over MgSO₄, filtered, and concentrated in vacuo. The residue was purified by chromatography on silica (petroleumether:EtOAc=100:0 to 90:10) to give the title compound.

Step 3: 2-Bromo-5-methylthiophene-3-carboxylic acid (J3)

A solution of the product from step 2 (3.0 g, 12 mmol) and LiOH.hydrate (1.51 g, 36 mmol) in 15 mL of ethanol and 15 mL of water was stirred at RT overnight. The reaction mixture was adjusted to ~pH=3 with 1N HCl and concentrated in vacuo. The residue was extracted with EtOAc (30 mL×3). The combined organic layers were dried over Na₂SO₄, filtered and the filtrate was concentrated in vacuo to give the title compound.

Step 4: 5-Methyl-2-(2H-1,2,3-triazol-2-yl)thiophene-3-carboxylic acid (Intermediate J)

To a solution of the product from step 3 (1.4 g, 6.33 mmol), cesium carbonate (6.17 g, 19.0 mmol) and CuI (0.12 g, 0.633 mmol) in DMF (30 mL) was added N,N'-dimethylcyclohexane-1,2-diamine (0.1 mL) and 1H-1,2,3-triazole (873 mL, 12.66 mmol). The resulting mixture was stirred at 110° C. overnight and the cooled mixture concentrated in vacuo, diluted with water (50 mL), and extracted with EtOAc (30 mL×3). The aqueous layer was acidified with 2N HCl and extracted with EtOAc (30 mL×4). The combined organic layers were washed with brine (50 mL×3), dried over Na₂SO₄, filtered and the filtrate concentrated in vacuo. The residue was purified by chromatography on silica gel (petroleumether:EtOAc=1:1) to give the title compound. LCMS m/z (M+H) 210.0 found, 210.0 required.

Intermediate K 2-(2,2-Difluoroethoxy)nicotinic acid

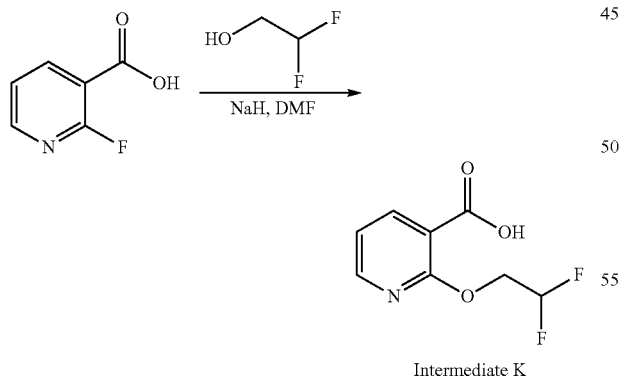

Intermediate K

To a suspension of 2,2-difluoroethanol (492 mg, 6.0 mmol) in DMF (10 mL) at 0° C. was added NaH (180 mg, 4.5 mmol) and the mixture was stirred at 0° C. for 0.5 h. A suspension of 2-fluoronicotinic acid (423 mg, 3.0 mmol) and NaH (180 mg, 4.5 mmol) in DMF (5 mL) was added dropwise at 0° C. and the resulting mixture was stirred at RT overnight. The mixture was diluted with water, acidified to ~pH=3 with 1M HCl and extracted with EtOAc (50 mL×3). The combined organic layers were washed with brine, dried over MgSO₄, filtered, and concentrated in vacuo to give the title. LRMS m/z (M+H) 204.1 found, 204.0 required. The following intermediates were made as described above, replacing 2,2-difluoroethanol with the appropriate alcohol

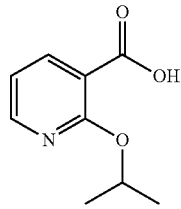

Intermediate K1

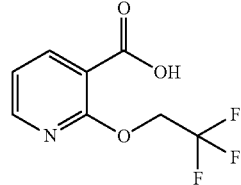

Intermediate K2

Intermediate L 2-(2-Methoxyethyl)benzoic acid

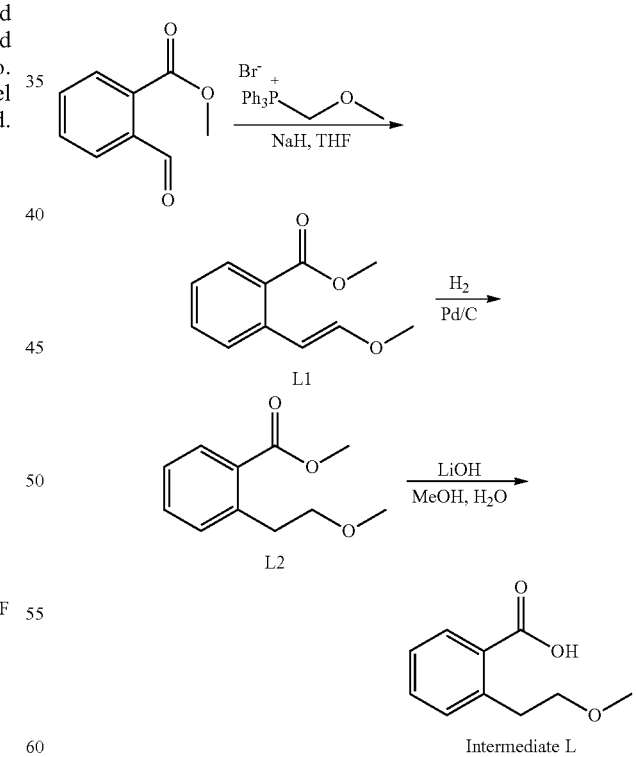

Step 1: (E)-Methyl 2-(2-methoxyvinyl)benzoate (L1)

To a suspension of (methoxymethyl)triphenylphosphonium bromide (9.44 g, 27.4 mmol) in THF (50 mL) was added NaH (1.46 g, 36.6 mmol) at 0° C. portion wise. The mixture was stirred at 0° C. for 0.5 h. Then a solution of methyl 2-formylbenzoate (3.0 g, 18.3 mmol) in THF (15 mL) was added dropwise and the reaction mixture was stirred at RT for 12 h. The mixture was diluted with water and extracted with EtOAc (30 mL×2). The combined organic layers was washed with brine, dried over MgSO$_4$, filtered, and concentrated in vacuo. The residue was purified by chromatography on silica (petroleumether:EtOAc=10:1 to 3:1) to give the title compound.

Step 2: Methyl 2-(2-methoxyethyl)benzoate (L2)

To a solution of the product from step 1 (2.3 g, 11.9 mmol) in EtOAc (30 mL) was added Pd/C (200 mg) at RT and the mixture was stirred at RT overnight under a balloon of H$_2$. The mixture was filtered and the filtrate was concentrated in vacuo to give the title compound, which was used directly in the next step.

Step 3: 2-(2-Methoxyethyl)benzoic acid (Intermediate L)

A mixture of the product from step 2 (2.2 g, 11.3 mmol) and LiOH (1.43 g, 33.9 mmol) in methanol (15 mL) and water (15 mL) was stirred at RT overnight. The mixture was adjusted to ~pH=3 with 1N HCl and concentrated in vacuo. The residue was extracted with EtOAc (30 mL×3), and the combined organic layers were dried over Na$_2$SO$_4$, filtered and the filtrate was concentrated in vacuo to give the title compound, which was used in the next step without further purification.

Intermediate M 2-(2,2-difluorocyclopropyl)benzoic acid

Step 1: methyl 2-vinylbenzoate (M1)

To a solution of methyl 2-bromobenzoate (1.2 g, 5.5 mmol) in dioxane/water (15 mL/0.6 mL) were added 4,4,5,5-tetramethyl-2-vinyl-1,3,2-dioxa borolane (1.7 g, 11.1 mmol), K2CO3 (1.53 g, 11.1 mmol) and Pd(dppf)Cl2 (0.4 g). The resulting mixture was stirred at 100° C. overnight. After cooled to RT, the mixture was diluted with water (20 mL) and extracted with EtOAc (30 mL×3). The combined organic layers were washed with brine, dried over sodium sulfate, filtered and the filtrate was concentrated in vacuo. The residue was purified by Prep-TLC (10% EtOAc in petroleum ether) to give the title compound. LRMS m/z (M+H) 163.1 found, 163.1 required. $^1$H NMR (Methanol-d4, 400 MHz): δ 7.87 (d, J=7.6 Hz, 1H), 7.28-7.57 (m, 4H), 5.61 (d, J=17.6 Hz, 1H), 5.35 (d, J=11.2 Hz, 1H), 3.88 (s, 3H).

Step 2: methyl 2-(2,2-difluorocyclopropyl)benzoate (M2)

A mixture of the product from step 1 (500 mg, 3.09 mmol) and KI (1.15 g, 6.94 mmol) in DME (27.8 mg, 0.31 mmol) and dioxane (461.7 mg, 5.25 mmol) was stirred at 120° C. for 5 minutes. Then TMSCl (666.6 mg, 6.17 mmol) and methyl 2,2-difluoro-2-(fluorosulfonyl)acetate (1.2 g, 6.17 mmol) were added. The resulting mixture was stirred at 120° C. for 24 hs. After cooled to RT, the mixture was quenched with water and extracted with EtOAc (10 mL×3). The combined organic layers were dried over sodium sulfate, filtered and concentrated in vacuo. The residue was purified through Prep-HPLC to afford the title product. LRMS m/z (M+H) 213.2 found, 213.2 required.

Step 3: 2-(2,2-difluorocyclopropyl)benzoic acid (Intermediate M)

A solution of the product from step 2 (170 mg, 0.8 mmol) and LiOH (23 mg, 0.55 mmol) in mixed solvent THF:H2O:MeOH (2:2:1) was stirred at 0° C. overnight. The reaction mixture was diluted by H2O (6 mL), adjusted pH to ~2 with 1 M HCl and extracted with EtOAc (8 mL×3). The combined organic layers were washed with brine (10 mL), dried over sodium sulfate, filtered and concentrated in vacuo. The residue was purified by Prep-HPLC to give the title compound. LRMS m/z (M+H) 199.1 found, 199.1 required. $^1$H NMR (Methanol-d4, 400 MHz): δ 7.95 (d, J=7.2 Hz, 1H), 7.34-7.53 (m, 3H), 3.31-3.36 (m, 1H), 1.81-1.84 (m, 1H), 1.62-1.66 (m, 1H).

Intermediate N 2-(2,2-difluoroethoxy)benzoic acid

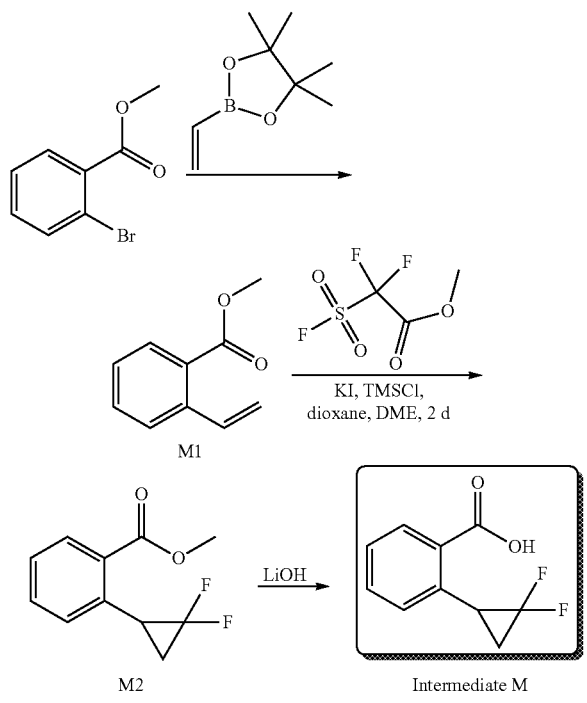

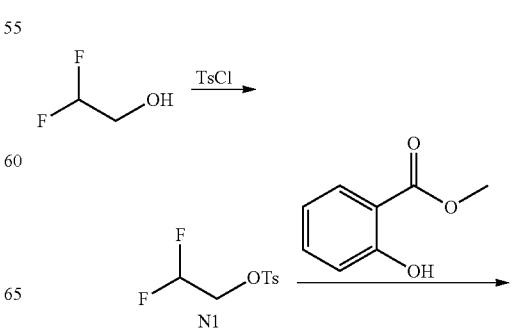

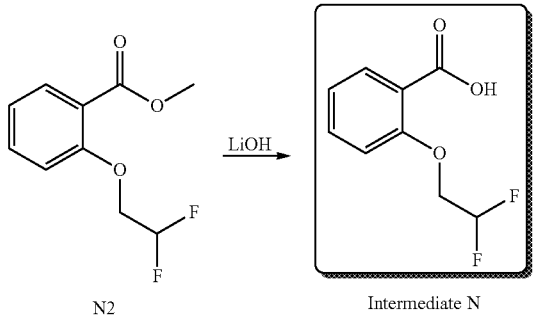

Step 1: 2,2-difluoroethyl 4-methylbenzenesulfonate (N1)

To a solution of compound 2,2-difluoroethanol (8.2 g, 100 mmol) in DCM (200 mL) at 0° C. was added Et3N (15.1 g, 150 mmol) and TsCl (19.0 g, 100 mmol). The resulting mixture was stirred at 0° C. for 0.5 h, then poured into water and extracted with DCM (200 mL×3). The combined organic layers were dried over MgSO4, filtered and concentrated in vacuo to give the title compound. $^1$HNMR (Methanol-d4, 400 MHz): δ 7.74 (d, J=8.2 Hz, 1H), 7.31 (d, J=8.2 Hz, 1H), 5.65-6.07 (m, 1H), 4.10 (td, J=12.6, 4.1 Hz, 2H), 2.40 (s, 3H).

Step 2: methyl 2-(2,2-difluoroethoxy)benzoate (N2)

To a suspension of the product from step 1 (7.6 g, 50.0 mmol) and K2CO3 (13.8 g, 100 mmol) in THF (300 mL) was added methyl 2-hydroxybenzoate (11.8 g, 50.0 mmol). The resulting mixture was stirred at 70° C. overnight. After cooled to RT, the mixture was poured into water and extracted with EtOAc (200 mL×3). The combined organic layer was dried over MgSO4, filtered and concentrated in vacuo. The residue was purified by chromatography on silical gel (3.2% EtOAc in petroleum ether) to give the title compound. $^1$H NMR (CDCl$_3$, 400 MHz): δ 7.73-7.89 (m, 1H), 7.41-7.60 (m, 1H), 7.07 (t, J=7.4 Hz, 1H), 6.96 (d, J=8.2 Hz, 1H), 5.87-6.33 (m, 1H), 4.24 (td, J=12.9, 3.9 Hz, 2H), 3.88 (s, 3H)

Step 3: 2-(2,2-difluoroethoxy)benzoic acid (Intermediate N)

To a solution of the product from step 2 (4.5 g, 20.8 mmol) in methanol/water (100 mL/100 mL) was added LiOH.H$_2$O (4.37 g, 104 mmol). The resulting mixture was stirred at RT overnight. The mixture was diluted with water (100 mL) and extracted with EtOAc (100 mL×3). The aqueous layer was acidified with HCl (2 mol/L) to ~pH=2 and extracted with DCM (100 mL×4). The combined organic layers were washed with brine, dried over sodium sulfate, filtered and the filtrate was concentrated in vacuo to give the title compound. LRMS m/z (M+H) 203.1 found, 203.1 required. $^1$HNMR (Methanol-d4, 400 MHz): δ 7.80 (dd, J=7.5, 1.5 Hz, 1H), 7.44-7.62 (m, 1H), 7.03-7.28 (m, 2H), 5.97-6.45 (m, 1H), 4.31 (td, J=13.4, 4.0 Hz, 2H).

Intermediate O 2-(2,2,2-trifluoroethyl)benzoic acid

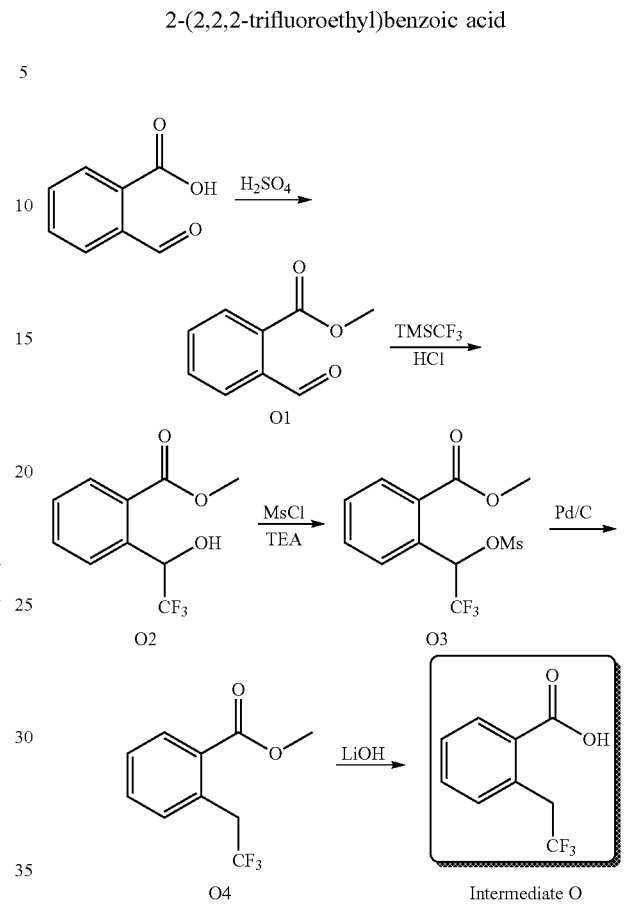

Step 1: methyl 2-formylbenzoate (O1)

To a solution of H2SO4 (2 mL) in MeOH (100 mL) was added 2-formyl benzoic acid (10.0 g, 66.2 mmol). The resulting mixture was stirred at 70° C. overnight. After cooled to RT, the mixture was concentrated in vacuo, adjusted pH to ~8 with aq. NaHCO3 and extracted with EtOAc (10 mL×3). The combined organic layers were dried over anhydrous sodium sulfate, filtered and concentrated in vacuo. The residue was purified by silica gel gradient chromatography (10% EtOAc in petroleum ether) to give the title compound. LRMS m/z (M+H) 165.1 found, 165.1 required. $^1$H NMR (CDCl$_3$, 400 MHz): δ 10.58 (s, 1H), 7.89-7.95 (m, 2H), 7.60-7.63 (m, 2H), 3.95 (s, 3H).

Step 2: methyl 2-(2,2,2-trifluoro-1-hydroxyethyl)benzoate (O2)

To a suspension of the compound from step 1 (3.60 g, 21.9 mmol) and CsF (1.67 g, 10.9 mmol) in dry THF (36 mL) at 0° C. was added TMSCF3 (4.68 g, 32.9 mmol). The mixture was stirred at 0° C. for 1 h. The mixture was adjusted to ~pH=2 with 1N HCl solution, stirred for another 1 h, and extracted with EtOAc (10 mL×3). The combined organic layers were dried over anhydrous sodium sulfate, filtered and concentrated in vacuo and the residue was purified by silica gel gradient chromatography (10% EtOAc in petroleum ether) to give the title compound. LRMS m/z (M+H)

235.1 found, 235.1 required. $^1$H NMR (CDCl$_3$, 400 MHz): δ 7.97 (d, J=8.0 Hz, 1H), 7.69 (d, J=8.0 Hz, 1H), 7.58 (t, J=7.2 Hz, 1H), 7.45 (t, J=7.2 Hz, 1H), 5.92 (br, 1H), 4.51 (br, 1H), 3.92 (s, 3H).

Step 3: methyl 2-(2,2,2-trifluoro-1-((methylsulfonyl)oxy)ethyl)benzoate (O3)

To a solution of the compound from step 2 (1.10 g, 4.70 mmol) and TEA (1.96 mL, 14.1 mmol) in DCM (10 mL) at RT was added MsCl (807 mg, 7.05 mmol) dropwise. The resulting mixture was stirred at RT for 1.5 hr, diluted with DCM and washed with brine (5 mL×2), dried over anhydrous sodium sulfate, filtered and the filtrate was concentrated in vacuo to give the title compound. LRMS m/z (M+H) 313.0 found, 313.0 required. 1H NMR (CDCl3, 400 MHz): δ 8.07 (d, J=7.6 Hz, 1H), 7.79 (d, J=8.4 Hz, 1H), 7.65 (t, J=6.0 Hz, 1H), 7.51-7.55 (m, 2H), 3.93 (s, 3H), 3.05 (s, 3H).

Step 4: methyl 2-(2,2,2-trifluoroethyl)benzoate (O4)

A solution of the product from step 3 (1.00 g, 3.20 mmol) in methanol (40 mL) was stirred in the presence of Pd/C (1.0 g) under 50 psi of H2 atmosphere at 50° C. overnight. LC-MS indicated the reaction was completed and the mixture was filtered through celite pad. The filtrate was concentrated in vacuo to give the title compound. LRMS m/z (M+H) 219.1 found, 219.1 required.

Step 5: 2-(2,2,2-trifluoroethyl)benzoic acid (Intermediate O)

To a solution of the product from step 4 (550 mg, 2.50 mmol) in MeOH/H2O (10 mL/1 mL) was added LiOH (240 mg, 10.0 mmol) at RT. The resulting mixture was stirred at RT for 12 hours. Water (10 mL) was added and the mixture was extrated with EtOAc (10 mL×2). The aqueous layer was adjusted to pH=~3 with conc. HCl and extracted with DCM (20 mL×3). The combined organic layers were washed with brine (20 mL), dried over sodium sulfate, filtered and the filtrate was concentrated in vacuo to give the title compound. LRMS m/z (M+H) 205.0 found, 205.0 required. 1H NMR (Methanol-d4, 400 MHz): δ 7.99 (d, J=7.4 Hz, 1H), 7.49-7.58 (m, 1H), 7.37-7.49 (m, 2H), 4.09 (q, J=11.0 Hz, 2H)

Intermediate P 2-(2,2-difluoroethyl)benzoic acid

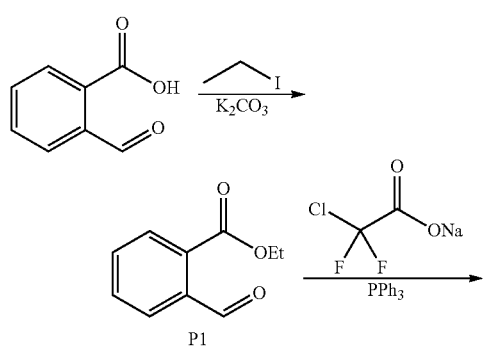

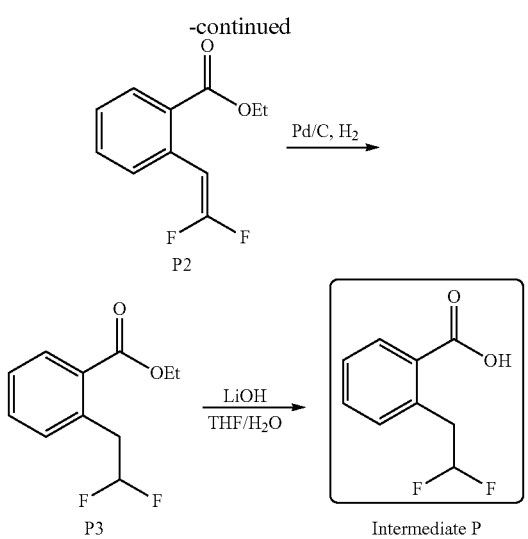

Step 1: ethyl 2-formylbenzoate (P1)

To a suspension of 2-formylbenzoic acid (34.5 g, 0.23 mol) and K2CO3 (65.1 g, 0.47 mol) in acetone (500 mL) was added EtI (72 g, 0.46 mol). The resulting mixture was stirred at 70° C. overnight. After cooled to RT, the mixture was filtered and the filtrate was concentrated in vacuo to give the title compound which was used without further purification. LRMS m/z (M+H) 179.2 found, 179.2 required.

Step 2: ethyl 2-(2,2-difluorovinyl)benzoate (P2)

To a stirred solution of the compound from step 1 (20.0 g, 0.11 mol) in DMF (190 mL) was added F$_2$ClCCO$_2$Na (25.6 g, 0.17 mol) and PPh$_3$ (44.2 g, 0.17 mol). The resulting mixture was stirred at 120° C. overnight. After cooled to RT, the mixture was diluted with water (200 mL) and extracted with EtOAc (300 mL×2). The combined organic layer was washed with brine (300 mL×2), dried over Na2SO4, filtered and concentrated in vacuo. The residue was purified by silica gel gradient chromatography (0%-10% EtOAc in petroleum ether) to give the title product. LRMS m/z (M+H) 213.2 found, 213.2 required.

Step 3: ethyl 2-(2,2-difluoroethyl)benzoate (P3)

To a stirred solution of the product from step 2 (2.7 g, 13 mmol) in EtOH (80 mL) was added Pd/C (0.4 g). The resulting mixture was stirred at 50° C. under hydrogen atmosphere (50 psi) overnight. After cooled to RT, the mixture was filtered and the filtrated was concentrated in vacuo to give the title compound. LRMS m/z (M+H) 215.2 found, 215.2 required.

Step 4: 2-(2,2-difluoroethyl)benzoic acid (Intermediate P)

To a solution of the product from step 3 (2.7 g, 12.6 mmol) in THF/H2O (20 mL/7 mL) was added LiOH.H2O (1.06 g, 25.2 mmol). The resulting mixture was stirred at RT overnight. After the solvent was removed, the residue was diluted with water (20 mL) and extracted with EtOAc (20 mL×3). The aqueous layer was adjusted to pH=~3, the precipitate was collected via filtration to give the title compound. 1HNMR (Methanol-d4, 400 MHz): δ 3.56 (td, J=16.63, 4.64 Hz, 2 H), 5.87-6.30 (m, 1 H), 7.35-7.46 (m, 2 H), 7.49-7.59 (m, 1 H), 8.02 (d, J=7.78 Hz, 1 H).

Intermediate Q 2-(2,2,2-trifluoroethyl)nicotinic acid

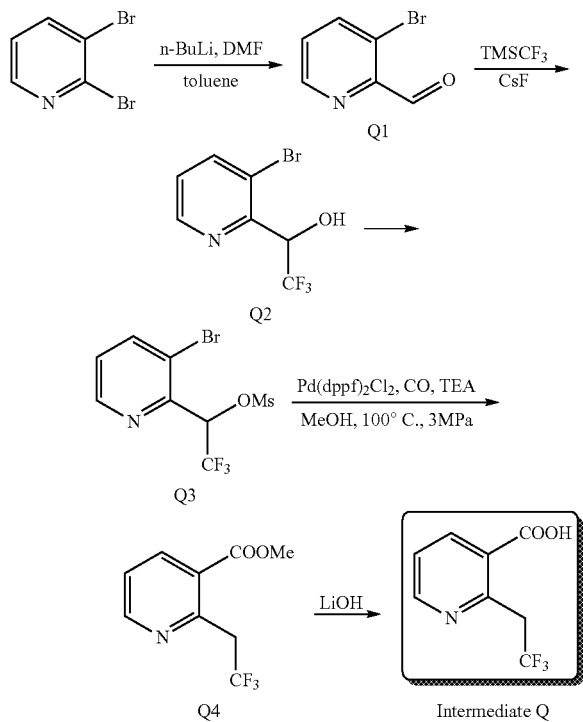

Step 1: 2-(2,2-difluoroethyl)benzoic acid (Q1)

To a solution of 2,3-dibromopyridine (10 g, 42.2 mmol) in toluene (100 mL) was dropwise added t-BuLi (20.26 mL, 50.7 mmol) at −78° C. under N2. After the resulting mixture was stirred at −78° C. for 2h, DMF (3.92 mL, 50.7 mmol) was added dropwise. The mixture was stirred at −78° C. for another 2h. The mixture was then quenched with water at −78° C. and extracted with EtOAc (300 mL×3). The combined organic layers were dried over MgSO4, filtered and concentrated in vacuo. The residue was purified by combiflash (25% EtOAc in petroleum ether) to give the title compound. LRMS m/z (M+H) 186.1 found, 186.1 required.

Step 2: 2-(2,2-difluoroethyl)benzoic acid (Q2)

To a suspension of the product from step 1 (3.5 g, 18.9 mmol) and CsF (4.3 g, 28.4 mmol) in THF (30 mL) at 0° C. was added TMSCF3 (4.0 g, 28.4 mmol) under N2. The resulting mixture was allowed to be stirred at room temperature for 2h. LC-MS indicated the reaction was finished. The mixture was diluted with water and extracted with EtOAc (100 mL×3). The organic layers were combined and dried over MgSO4, filtered and concentrated in vacuo. The residue was purified by combiflash (25% EtOAc in petroleum ether) to give the title compound. LRMS m/z (M+H) 256.1 found, 256.1 required.

Step 3: 2-(2,2-difluoroethyl)benzoic acid (Q3)

To a solution of the product from step 2 (1.8 g, 7 mmol) and DIPEA (1.8 g, 14 mmol) in DCM (10 mL) was dropwise added MsCl (1.1 mL, 14 mmol) at 0° C. under N2. The mixture was stirred at 0° C. for 2h. The mixture was diluted with water, extracted with EtOAc (200 ml×3). The organic layers were combined, dried over MgSO4, filtered and concentrated in vacuo to give the title compound. LRMS m/z (M+H) 334.3 found, 334.3 required.

Step 4: 2-(2,2-difluoroethyl)benzoic acid (Q4)

A mixture of the product from step 3 (1.0 g, 3 mmol), Pd(dppf)Cl2 (100 mg), TEA (909 mg, 9 mmol) in methanol (30 mL) was stirred at 120° C. for 16 hs under CO (3 MPa). LC-MS indicated the reaction was finished. After filtration, the filtrate was concentrated in vacuo. The residue was purified by silica chromatography (25% EtOAc petroleum ether) to give the title compound. LRMS m/z (M+H) 220.1 found, 220.1 required.

Step 5: 2-(2,2-difluoroethyl)benzoic acid (Intermediate Q)

To a solution of the product from step 4 (1.0 g, 4.6 mmol) in the mixture of MeOH (15 ml) and water (15 mL) was added LiOH (0.22 g, 9.1 mmol). The resulting mixture was stirred at room temperature for 2 h. After most of MeOH was removed under reduced pressure, the residue was diluted with water (20 mL) and extracted with EtOAc (100 mL×3). The aqueous layer was adjusted pH=~1 with conc. HCl and then extracted with EtOAc (100 ml×3). The organic layers were combined, dried over MgSO4, filtered and concentrated in vacuo to give the title compound. LRMS m/z (M+H) 206.1 found, 206.1 required. 1H NMR (Methanol-d4, 400 MHz): δ 8.30-8.70 (m, 2H), 7.30-7.60 (m, 1H) 4.00-4.50 (m, 2H).

Intermediate R 2-propylbenzoic acid

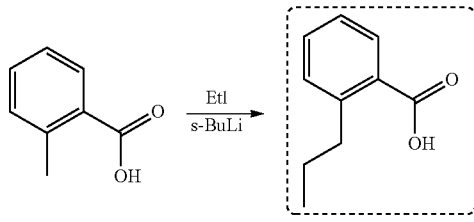

Step 1: 2-propylbenzoic acid (Intermediate R)

To a solution of 2-methylbenzoic acid (20 g, 0.15 mmol) in THF (200 mL) was dropwise added s-BuLi (340 mL, 0.45 mmol) at −78° C. After addition, the mixture was stirred at −78° C. for 0.5 h. Then iodoethane (137 g, 0.88 mmol) was added. The resulting mixture was allowed to warm up to RT, stirred overnight, quenched with water, and extracted with EtOAc (300 mL×3). The combined organic layers were washed with brine, dried over MgSO4, filtered and concentrated in vacuo. The residue was purified by silica chromatography (50% EtOAc in petroleum ether) to give the title compound. LRMS m/z (M+H) 165.1 found, 165.1 required. 1H NMR (DMSO-d6, 400 MHz): δ 12.80 (brs, 1 H), 7.75~7.73 (m, 1 H), 7.39~7.43 (m, 1 H), 7.22~7.36 (m, 2 H), 2.87~2.84 (m, 2 H), 1.49~1.54 (m, 2 H), 0.84~0.87 (m, 3 H).

Intermediate S 2-(1-Cyanocyclopropyl)benzoic acid

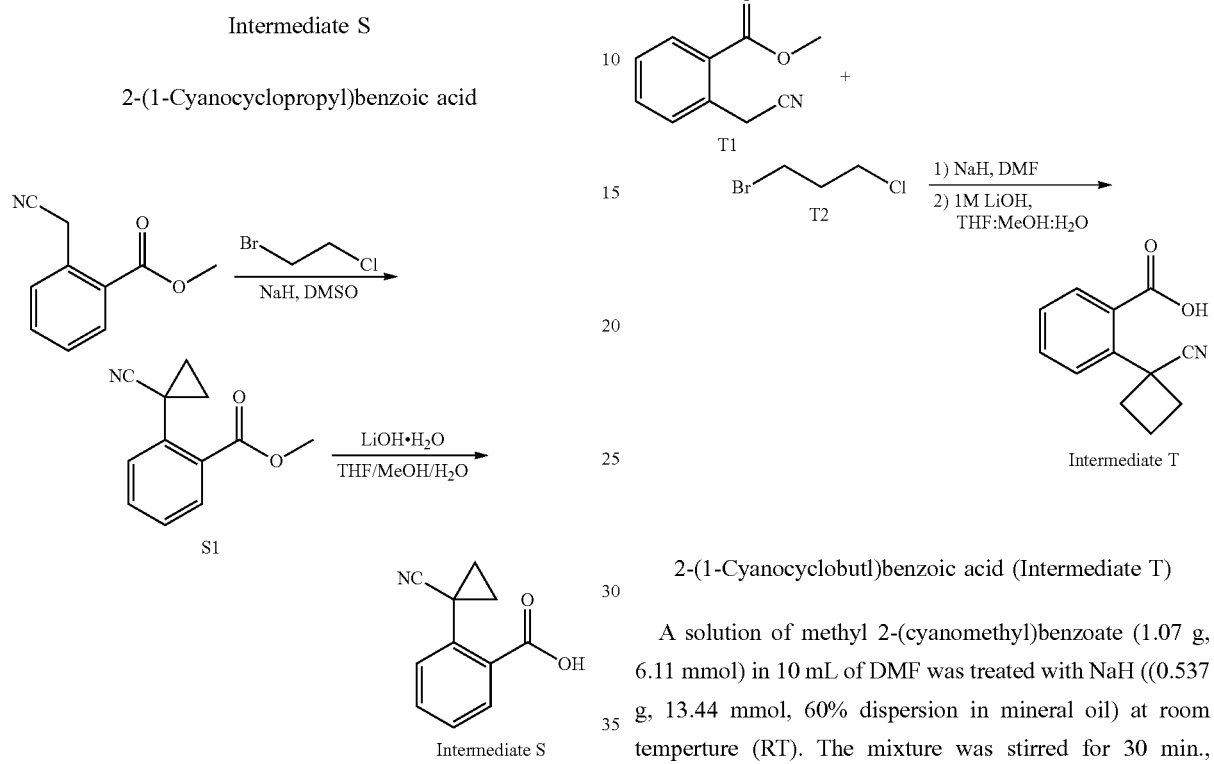

Step 1: Methyl 2-(1-cyanocyclopropyl)benzoate (S2)

To a solution of NaH (1.1 g, 26.2 mmol) in DMSO (20 mL) was added compound methyl 2-(cyanomethyl)benzoate (2 g, 11.4 mmol). After stirring at room temperature under nitrogen for 1 h, 1-bromo-2-chloroethane (1.8 g, 12.6 mmol) was added and the mixture was stirred at room temperature for 2h. The mixture was then quenched with ice water (10 mL) and extracted with EtOAc (10 mL×3). The organic layers were combined, dried and concentrated in vacuo to give the crude compound, which was purified by column chromatography on silica gel eluting with (Petroleum Ether/EtOAc 20:1) to give the title compound. MS (ESI) m/e (M+H+) was detected.

Step 2: 2-(1-Cyanocyclopropyl)benzoic acid

A solution of compound S1 in THF/MeOH/H2O (3:1:1, 16 mL) was treated with lithium hydroxide in water (3 mL). The mixture was stirred overnight at room temperature. The THF and MeOH were removed in vacuo and the resulting solution was acidified to pH ~1 with HCl (1 N) to give a white crystalline precipitate. The crystals were isolated by filtration, washed with water and dried in vacuo to give the title compound. MS (ESI) m/e (M+H+): 187.9.

Intermediate T 2-(1-Cyanocyclobutyl)benzoic acid 2-(1-Cyanocyclobutl)benzoic acid (Intermediate T)

A solution of methyl 2-(cyanomethyl)benzoate (1.07 g, 6.11 mmol) in 10 mL of DMF was treated with NaH ((0.537 g, 13.44 mmol, 60% dispersion in mineral oil) at room temperture (RT). The mixture was stirred for 30 min., 1-bromo-3-chloropropane (1.06 g, 6.72 mmol) added and the reaction mixture stirred at RT. Et20 (10 mL) was added, the mixture cooled to 0° C., quenched with water and extracted with Et20 (75 mL×2). The combined organic fractions were washed with brine (40 mL), dried over Na2SO4, filtered and the solvent was evaporated in vacuo. The crude material was purified by silica gel gradient chromatography (0-20% EtOAc in hexanes), providing methyl 2-(1-cyanocyclobutyl)benzoate. Methyl 2-(1-cyanocyclobutyl)-benzoate (210 mg, 0.976 mmol) was dissolved in THF (2 mL), MeOH (0.7 mL) and H2O (0.7 mL) and treated with aq 2M LiOH (1.0 mL, 2 mmol) and the mixture stirred at RT overnight. Additional 2 M LiOH (0.5 mL) and 0.5 mL of MeOH were added and stirring continued for 8 h, followed by a further addition of 2M LiOH (0.5 mL) and stirring for 16h. MeOH and THF were evaporated, the pH of the resulting aqueous solution was adjusted to ~6 with 1 M HCl and extracted with EA (3×75 mL). The combined organic fractions were washed with brine, dried over Na2SO4, filtered and evaporated in vacuo to give the title compound, which was used directly without further purification. LRMS m/z (M+H) 202.1 found, 202.2 required.

Intermediate U

3-(2H-1,2,3-triazol-2-yl)picolinic acid

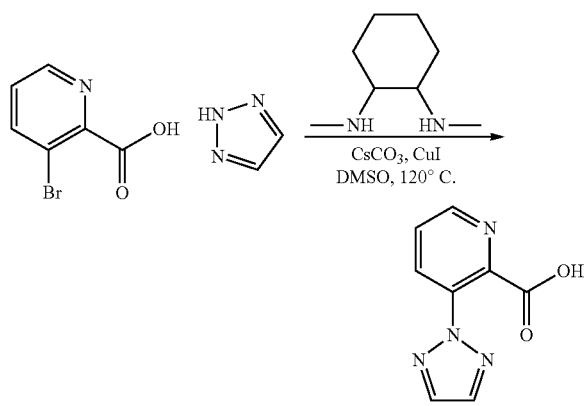

3-(2H-1,2,3-triazol-2-yl)picolinic acid

To a solution of 3-bromonicotinic acid (1.4 g, 6.93 mmol) in DMSO (14 mL) was added 2H-1,2,3-triazole (0.718 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The reaction mixture was sparged with nitrogen and stirred at 120° C. overnight. The cooled reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over NaSO4, filtered, and the solvent was evaporated in vacuo. The crude product was purified by chromatography on silica (0-100% (5% AcOH in EtOAc)/hexanes). The purified fractions were combined and azetroped with toluene (3×100 mL) to give the title compound. LRMS m/z (M+H) 191.05 found, 191.05 required.

Intermediate V

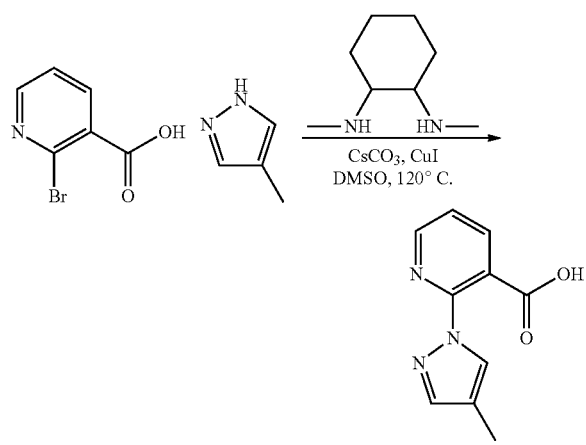

Intermediate M

2-(4-Methyl-1H-pyrazol-1-yl)nicotinic acid

To a solution of 2-bromonicotinic acid (1.4 g, 6.93 mmol) in DMSO (14 mL) was added 4-methyl-1H-pyrazole (0.852 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The reaction was sparged with nitrogen and heated at 120° C. overnight. The cooled reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over NaSO4, filtered, and the solvent was evaporated in vacuo. The crude material was purified by chromatography on silica [0-100% (5% AcOH in EtOAc)/hexanes] the title compound. LRMS m/z (M+H) 204.07 found, 204.07 required.

The following intermediate M1 was made using the procedures described herein.

M1

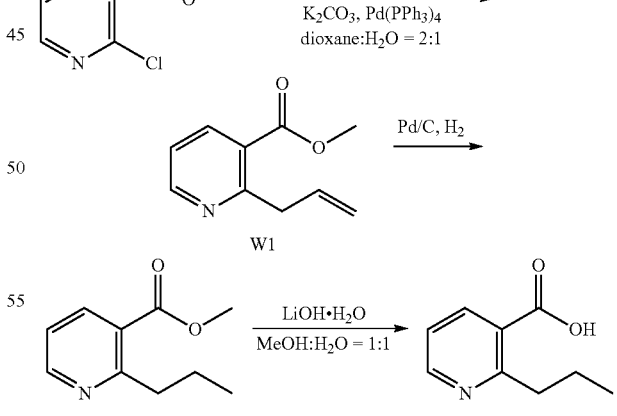

Intermediate W

2-propylnicotinic acid

Step 1: methyl 2-allylnicotinate (W1)

To a solution of methyl 2-chloronicotinate (300 mg, 1.75 mmol) in dioxane/H2O (2 mL/1 mL) were added 2-allyl-4,5-dimethyl-1,3,2-dioxaborolane (354 mg, 2.11 mmol), K2CO3 (605 mg, 4.39 mmol) and Pd(PPh3)4 (203 mg, 0.175 mmol). The resulting mixture was stirred at 100° C. for 3 hours. After cooled to RT, the mixture was diluted with water (10 mL) and extracted with EtOAc (20 mL×3). The combined organic layers were washed with brine, dried over Na2SO4, filtered, and concentrated in vacuo. The residue was purified by Prep-TLC (9% EtOAc in petroleum ether) to give the title compound. LRMS m/z (M+H) 178.2 found, 178.1 required.

Step 2: methyl 2-propylnicotinate (W2)

To a solution of the product from step 1 (4.8 g, 27.1 mmol) in EtOAc (200 mL) was added Pd/C (500 mg, 10 wt %). The resulting mixture was stirred under the steam of H2 at room temperature overnight. The mixture was filtered and concentrated in vacuo to give the title compound which was used directly without further purification. LRMS m/z (M+H) 180.2 found, 180.1 required.

Step 3: 2-propylnicotinic acid (Intermediate W)

To a solution of the product from step 3 (4.7 g, 26.3 mmol) in MeOH/H2O (40 mL/40 mL) was added LiOH.H2O (1.65 g, 39.4 mmol). The resulting mixture was stirred at room temperature overnight. The mixture was diluted with water (50 mL) and extracted with EtOAc (70 mL×4). The aqueous layer was acidified with HCl (2 mol/L) to pH=2 and extracted with EtOAc (200 mL×7). The combined organic layers were dried over Na2SO4, filtered, and concentrated in vacuo. The residue was purified by chromatography (50% EtOAc in petroleum ether) to provide the title compound. LRMS m/z (M+H) 166.1 found, 166.1 required.

Intermediate X 2-(3-Methyl-1,2,4-oxadiazol-5-yl)benzoic acid

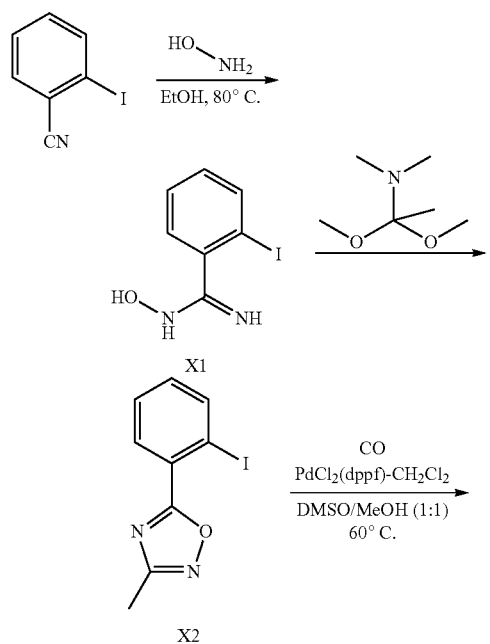

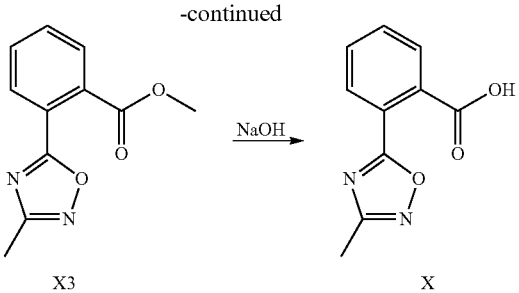

Step 1: N-Hydroxy-2-iodobenzimidamide(X1)

To a solution of 2-iodobenzonitrile (15 g, 65.5 mmol) in EtOH (262 mL) was added hydroxylamine (12.98 g, 196 mmol) and the mixture heated to 80° C. overnight, cooled and concentrated in vacuo. The crude mixture was diluted with EtOAc (300 mL) and washed with water (300 mL) and brine (300 mL). The organic layer was dried over NaSO4, filtered, and concentrated in vacuo to give the title product. LRMS m/z (M+H) 263.0 found, 263.0 required.

Step 2: 5-(2-Iodophenyl)-3-methyl-1,2,4-oxadiazole(X2)

To 1,1-dimethoxy-N,N-dimethylethanamine (26.4 g, 198 mmol) was added the product from step 1 (26 g, 99 mmol) and the mixture was stirred at rt for 1 h. The mixture was diluted with EtOAc (30 mL) and washed with water (30 mL) and brine (30 mL). The organic layer was dried over NaSO4, filtered, and concentrated in vacuo. The crude material was purified by chromatography on silica (0-20% EtOAc in hexanes) to provide the title compound. LRMS m/z (M+H) 287.0 found, 287.0 required.

Step 3: Methyl 2-(3-methyl-1,2,4-oxadiazol-5-yl)benzoate(X3)

To a solution of the product from step 2 (19 g, 66.4 mmol) in MeOH (133 mL) and DMSO (133 mL) was added triethylamine (23.1 mL, 166 mmol) and the mixture was sparged with nitrogen. PdCl2(dppf)-CH2Cl2 (2.71 g, 3.32 mmol) was added, the mixture was evacuated and placed under one atmosphere of carbon monoxide and stirred overnight at 60° C. The cooled reaction mixture was concentrated in vacuo and diluted with EtOAc (150 mL) and saturated aqueous NaHCO3. The mixture was filtered over a pad of celite. The filtrate was extracted with EtOAc (3×100 mL). The combined organic layers were washed with brine (200 mL), dried over NaSO4 and concentrated in vacuo. The crude material was purified by chromatography on silica (0-60% EtOAc in hexanes) to provide the title compound. LRMS m/z (M+H) 219.1 found, 219.1 required.

Step 4: 2-(3-Methyl-1,2,4-oxadiazol-5-yl)benzoic acid (X)

To a solution of the product from step 3 (10.2 g, 46.8 mmol) in MeOH (187 mL) was added 1 M NaOH (140 mL, 140 mmol) and the mixture was stirred at 50° C. overnight. The solution was cooled to rt and acidified with 12 N HCl to pH=~3 and concentrated to remove MeOH. The mixture was re-dissolved in EtOAc 200 mL) and washed with water (100 mL) and brine (100 mL). The organic layer was dried over NaSO4, filtered, and concentrated in vacuo to provide the title compound. LRMS m/z (M+H) 205.1 found, 205.1 required.

Intermediate Y 3-(Pyridin-2-yl)pyrazine-2-carboxylic acid

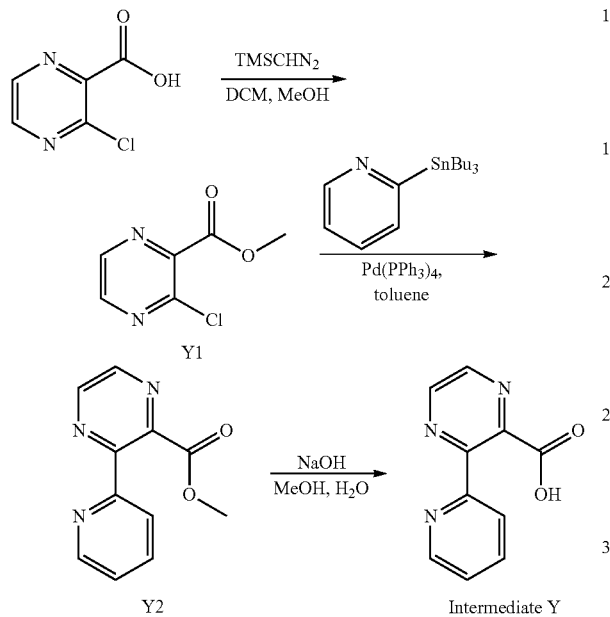

Step 1: methyl 3-chloropyrazine-2-carboxylate (Y1)

To a solution of 3-chloropyrazine-2-carboxylic acid (100 mg, 0.63 mmol) in DCM/MeOH (2 mL:0.2 mL) was added TMSCHN2 (0.47 mL, 0.95 mmol) at RT and the resulting mixture was stirred at RT for 2 h. Acetic acid (0.2 mL) was added and the mixture was diluted with water (2 mL) and extracted with DCM (4 mL×3). The combined organic layers were washed with brine, dried over Na2SO4, filtered, and concentrated in vacuo to give the title compound. LRMS m/z (M+H) 173.0 found, 173.0 required.

Step 2: Methyl 3-(pyridin-2-yl)pyrazine-2-carboxylate (Y2)

To a solution of the product from step 1 (100 mg, 0.58 mmol) in toluene (2 mL) was added Pd(PPh3)4 (134 mg, 0.12 mmol) and 2-(tributylstannyl)pyridine (213 mg, 0.58 mmol) at room temperature and the resulting mixture was heated to 100° C. overnight. After cooled to RT, the mixture was filtered and 5 mL of aq. KF solution was added to the filtrate. The resulting mixture was stirred for 30 mins and extracted with EtOAc (5 mL×3). The combined organic layers were washed with brine, dried over Na2SO4, filtered and concentrated in vacuo. The residue was purified by chromatography (30% EtOAc in petroleum ether) to provide the title compound. LRMS m/z (M+H) 216.1 found, 216.1 required.

Step 3: 3-(Pyridin-2-yl)pyrazine-2-carboxylic acid (Intermediate Y)

A solution of the product from step 2 (50 mg, 0.23 mmol) and NaOH (27.8 mg, 0.69 mmol) in 2 mL of methanol and 0.1 mL of water was stirred at RT overnight. After adjusting to pH=5 with 1N HCl, the mixture was concentrated in vacuo. The residue was dissolved in EtOAc (8 mL), stirred for 10 mins, and filtered. The filtrate was concentrated in vacuum to give the title compound. LRMS m/z (M+H) 202.1 found, 202.1 required.

Intermediate Z 3-(1H-Pyrazol-1-yl)pyrazine-2-carboxylic acid

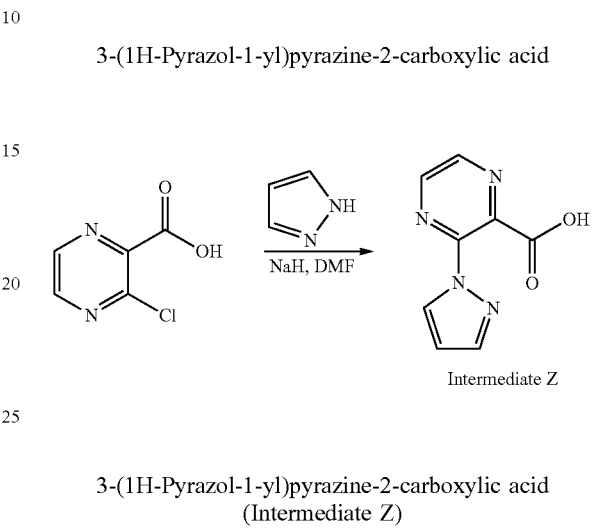

Intermediate Z 3-(1H-Pyrazol-1-yl)pyrazine-2-carboxylic acid (Intermediate Z)

To a suspension of sodium hydride (278 mg, 6.95 mmol, 60% in oil) in DMF (10 mL) was added 1H-pyrazole (279 mg, 4.11 mmol) at RT and the resulting mixture was stirred at room temperature for 30 mins. 3-Chloropyrazine-2-carboxylic acid (500 mg, 3.16 mmol) was added and the mixture heated to 60° C. for 2 h. After cooled to RT, water (20 mL) was added and the mixture extracted with 4.7% MeOH in DCM (20 mL×3). The combined organic layers were washed with brine, dried over Na2SO4, filtered, and concentrated in vacuo to give the title compound. LRMS m/z (M+H) 191.0 found, 191.0 required.

Example A

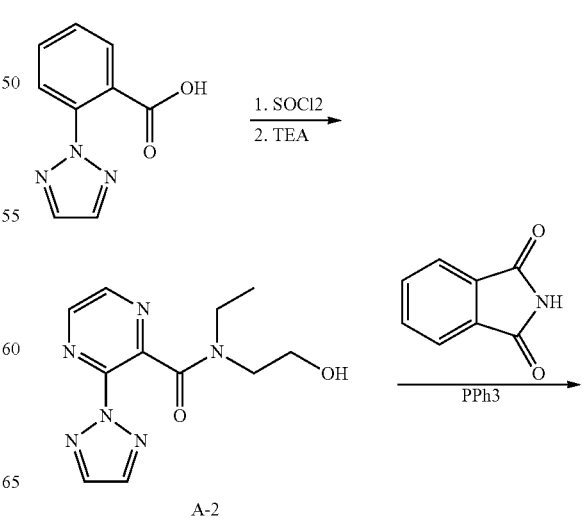

A-2

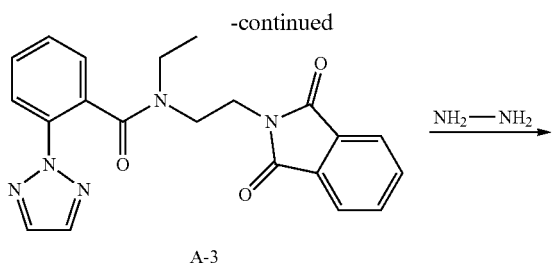

A-3

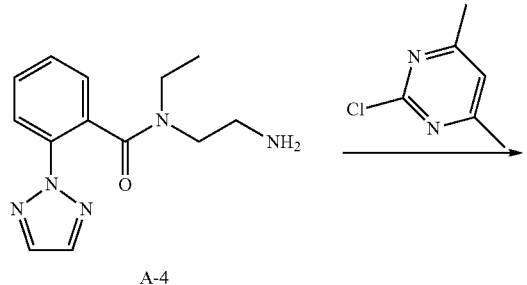

A-4

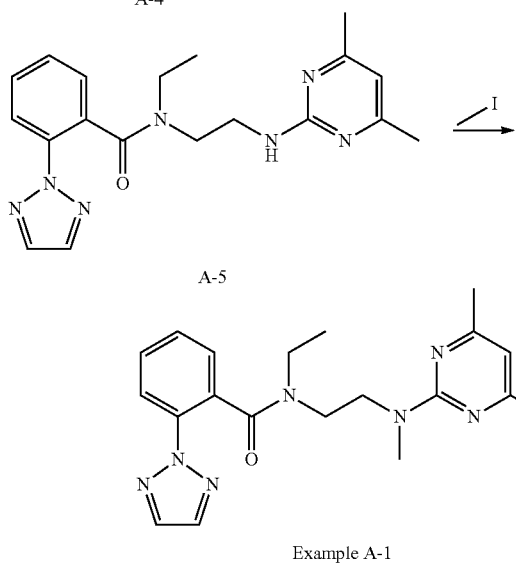

A-5

N-(2-((4,6-dimethylpyrimidin-2-yl)(methyl)amino)ethyl)-N-ethyl-2-(2H-1,2,3-triazol-2-yl)benzamide Step 1: N-ethyl-N-(2-hydroxyethyl)-2-(2H-1,2,3-triazol-2-yl)benzamide (A-2)

A solution of 2-(2H-1,2,3-triazol-2-yl)benzoic acid (2.10 g, 11.2 mmol) in SOCl2 (30 mL) was stirred at 80° C. for 2h. After cooled to RT, the mixture was concentrated in vacuo. To a solution of 2-(ethylamino)ethanol (997 mg, 11.2 mmol) and DIEA (4.30 g, 336. mmol) in DCM (15 mL) was added dropwise a solution of the above residue in DCM at 0° C. The resulting mixture was stirred at RT for 3 h, then quenched with water (50 mL) and extracted with EtOAc (80 mL×3). The organic layers were combined, dried over MgSO4, filtered, and concentrated in vacuo. The residue was purified by silica chromatography (50% EtOAc in petroleum ether) to give the title compound. LRMS m/z (M+H) 261.3 found, 261.1 required.

Step 2: N-(2-(1,3-dioxoisoindolin-2-yl)ethyl)-N-ethyl-2-(2H-1,2,3-triazol-2-yl)benzamide (A-3)

To a solution of the product from step 1 (200 mg, 0.768 mmol) in dry DCM (3 mL) was added isoindoline-1,3-dione (136 mg, 0.92 mmol), PPh3 (240 mg, 0.92 mmol) at 25° C. The resulting mixture was stirred for 10 min, then (Z)-di-tert-butyl diazene-1,2-dicarboxylate (230 mg, 1.0 mmol) was added. The mixture was stirred at room temperature for 12 h, then poured into water, and extracted with EtOAc (50 mL×3). The combined organic layers were washed with brine, dried over MgSO4, filtered, and concentrated in vacuo. The residue was purified by silica gel column (50% EtOAc in petroleum ether) to give the title compound. LRMS m/z (M+H) 390.1 found, 390.2 required.

Step 3: N-(2-aminoethyl)-N-ethyl-2-(2H-1,2,3-triazol-2-yl)benzamide (A-4)

A solution of the product from step 2 (260 mg, 0.668 mmol), NH2NH2H2O (43.5 mg, 0.868 mmol) in EtOH (3 mL) was stirred at 80° C. for 16 h. After cooled to RT, the mixture was concentrated in vacuo to give the title product. LRMS m/z (M+H) 260.1 found, 260.1 required.

Step 4: N-(2-((4,6-dimethylpyrimidin-2-yl)amino)ethyl)-N-ethyl-2-(2H-1,2,3-triazol-2-yl)benzamide (A-5)

To a solution of the product from step 3 (100 mg, 0.39 mmol) in 1,4-dioxane (2 mL) were added 2-chloro-4,6-dimethylpyrimidine (66 mg, 0.46 mmol) and Cs2CO3 (500 mg, 1.54 mmol). The resulting mixture was stirred at 80° C. for 12 h. After cooled to RT, the mixture was poured into water and extracted with EtOAc (50 mL×3). The combined organic layers were washed with brine, dried over MgSO4, filtered and concentrated in vacuo. The residue was purified by Prep-TLC (50% EtOAc in petroleum ether) to give the title compound. LRMS m/z (M+H) 366.1 found, 366.2 required.

Step 5: N-(2-((4,6-dimethylpyrimidin-2-yl)(methyl)amino)ethyl)-N-ethyl-2-(2H-1,2,3-triazol-2-yl)benzamide (Example A-1)

To a solution of the product from step 4 (50 mg, 0.137 mmol) in THF (2 mL) was added NaH (10.9 mg, 0.274 mmol) at 0° C. The mixture was stirred for 10 mins and MeI (38.8 mg, 0.27 mmol) was added. The resulting mixture was stirred at RT for 1h. Then the mixture was poured into water and extracted with EtOAc (100 mL×3). The combined organic layers were washed with brine, dried over MgSO4, filtered and concentrated in vacuo. The residue was purified by Prep-HPLC to give the title compound. LRMS m/z (M+H) 380.2 found, 380.2 required.

Example B

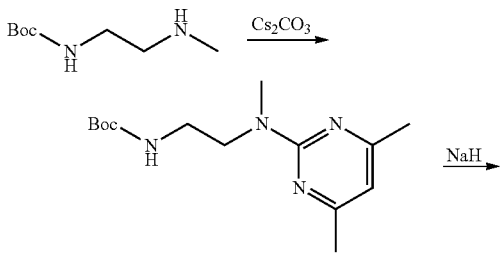

B-2

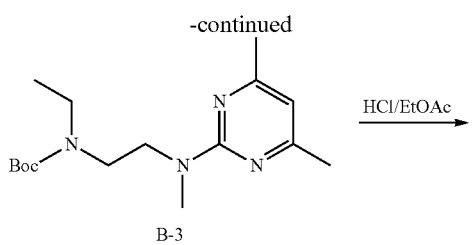

B-3

B-4

Example B-1

2-cyclopropyl-N-(2-((4,6-dimethylpyrimidin-2-yl)(methyl)amino)ethyl)-N-ethylbenzamide Step 1: tert-butyl (2-((4,6-dimethylpyrimidin-2-yl)(methyl)amino)ethyl)carbamate (B-2)

To a solution of tert-butyl (2-(methylamino)ethyl)carbamate (2.0 g, 11.48 mmol) in 1,4-dioxane (20 mL) were added 2-chloro-4,6-dimethylpyrimidine (1.96 g, 13.77 mmol) and K2CO3 (1.59 g, 11.48 mmol). The resulting mixture was stirred at 70° C. for 12 h. After cooled to RT, the mixture was poured into water and extracted with EtOAc (100 mL×3). The combined organic layers were washed with brine, dried over MgSO4, filtered and concentrated in vacuo to give the title compound. LRMS m/z (M+H) 281.2 found, 281.2 required.

Step 2: tert-butyl (2-((4,6-dimethylpyrimidin-2-yl)(methyl)amino)ethyl)(ethyl)carbamate (B-3)

To a solution of the product from step 1 (3.0 g, 10.7 mmol) in THF (30 mL) was added NaH (0.86 g, 21.4 mmol) at 0° C. The mixture was stirred for 10 min, then EtI (5.01 g, 32.1 mmol) was added. The resulting mixture was stirred at RT under N2 for 5 h, then quenched with water and extracted with EtOAc (100 mL×3). The combined organic layers were washed with brine, dried over MgSO4, filtered and concentrated in vacuo. The residue was purified by silica gel gradient chromatography (9.1% EtOAc in petroleum ether) to give the title compound. LRMS m/z (M+H) 309.2 found, 309.2 required.

Step 3: N1-(4,6-dimethylpyrimidin-2-yl)-N2-ethyl-N1-methylethane-1,2-diamine dihydrochloride (B-4)

To a solution of the product from step 2 (2.7 g, 8.75 mmol) in EtOAc (10 mL) was added HCl/EtOAc (15 ml, 43.8 mmol). The resulting mixture was stirred at RT for 1h, then concentrated in vacuo to give the title compound. LRMS m/z (M+H) 209.1 found, 209.2 required.

Step 4: 2-cyclopropyl-N-(2-((4,6-dimethylpyrimidin-2-yl)(methyl)amino)ethyl)-N-ethylbenzamide (Example B-1)

To a solution of 2-cyclopropylbenzoic acid (46.7 mg, 0.29 mmol) in DMF (2 mL) were added HATU (110 mg, 0.29 mmol), DIEA (0.17 ml, 0.96 mmol) and the product from step 3 (50 mg, 0.18 mmol). The mixture was stirred overnight at RT and then purified by Prep-HPLC to give the title compound. LRMS m/z (M+H) 353.2 found, 353.2 required.

TABLE 1

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-5 | (structure shown) | N-(2-((4,6-dimethylpyrimidin-2-yl)(methyl)amino)ethyl)-N-ethyl-2-isopropoxynicotinamide | Calc'd 372.2, found 372.2 |

TABLE 1-continued

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-6 | 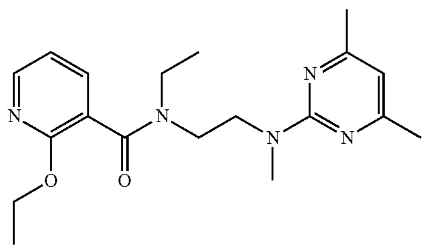 [SMILES: CCOc1ncccc1C(=O)N(CC)CCN(C)c1nc(C)cc(C)n1] | N-(2-((4,6-dimethylpyrimidin-2-yl)(methyl)amino)ethyl)-2-ethoxy-N-ethylnicotinamide | Calc'd 358.2 found 358.2 |
| B-7 | 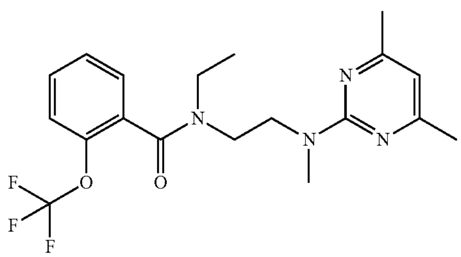 [SMILES: CCN(CCN(C)c1nc(C)cc(C)n1)C(=O)c1ccccc1OC(F)(F)F] | N-(2-((4,6-dimethylpyrimidin-2-yl)(methyl)amino)ethyl)-N-ethyl-2-(trifluoromethoxy)benzamide | Calc'd 397.2 found 397.1 |
| B-8 | 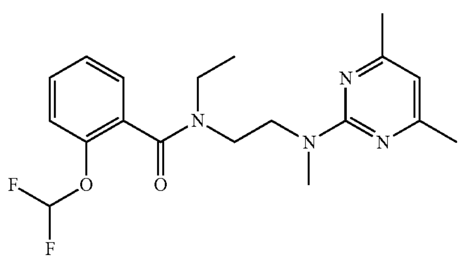 [SMILES: CCN(CCN(C)c1nc(C)cc(C)n1)C(=O)c1ccccc1OC(F)F] | 2-(difluoromethoxy)-N-(2-((4,6-dimethylpyrimidin-2-yl)(methyl)amino)ethyl)-N-ethylbenzamide | Calc'd 379.2 found 379.1 |
| B-9 | 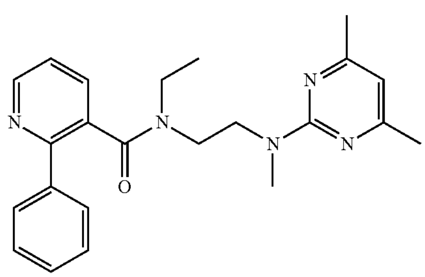 [SMILES: CCN(CCN(C)c1nc(C)cc(C)n1)C(=O)c1cccnc1-c1ccccc1] | N-(2-((4,6-dimethylpyrimidin-2-yl)(methyl)amino)ethyl)-N-ethyl-2-phenylnicotinamide | Calc'd 390.2 found 390.2 |
| B-10 | 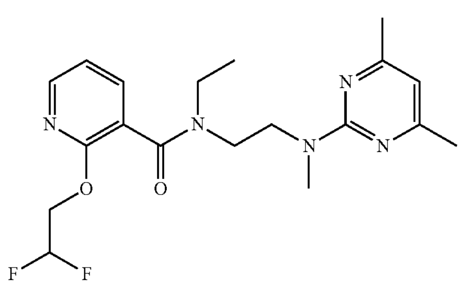 [SMILES: CCN(CCN(C)c1nc(C)cc(C)n1)C(=O)c1cccnc1OCC(F)F] | 2-(2,2-difluoroethoxy)-N-(2-((4,6-dimethylpyrimidin-2-yl)(methyl)amino)ethyl)-N-ethylnicotinamide | Calc'd 394.2 found 394.2 |

TABLE 1-continued

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-11 | 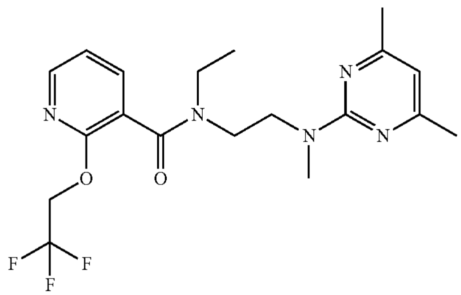 [SMILES: CCN(CCN(C)c1nc(C)cc(C)n1)C(=O)c1cccnc1OCC(F)(F)F] | N-(2-((4,6-dimethylpyrimidin-2-yl)(methyl)amino)ethyl)-N-ethyl-2-(2,2,2-trifluoroethoxy)nicotinamide | Calc'd 412.2 found 412.2 |
| B-12 | 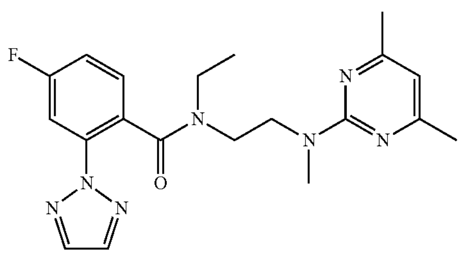 [SMILES: CCN(CCN(C)c1nc(C)cc(C)n1)C(=O)c1ccc(F)cc1-n1nccn1] | N-(2-((4,6-dimethylpyrimidin-2-yl)(methyl)amino)ethyl)-N-ethyl-4-fluoro-2-(2H-1,2,3-triazol-2-yl)benzamide | Calc'd 398.2, found 398.2 |
| B-13 | 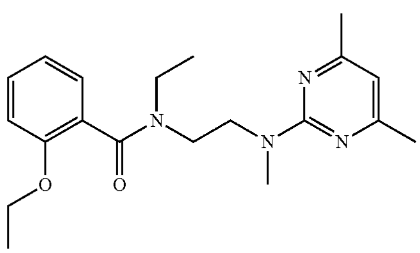 [SMILES: CCOc1ccccc1C(=O)N(CC)CCN(C)c1nc(C)cc(C)n1] | N-(2-((4,6-dimethylpyrimidin-2-yl)(methyl)amino)ethyl)-2-ethoxy-N-ethylbenzamide | Calc'd 357.2, found 357.2 |
| B-14 | 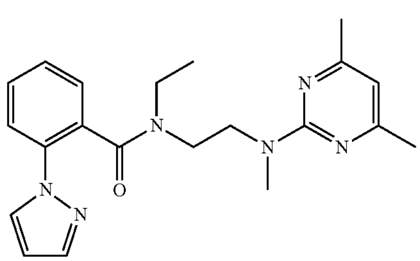 [SMILES: CCN(CCN(C)c1nc(C)cc(C)n1)C(=O)c1ccccc1-n1cccn1] | N-(2-((4,6-dimethylpyrimidin-2-yl)(methyl)amino)ethyl)-N-ethyl-2-(1H-pyrazol-1-yl)benzamide | Calc'd 379.2 found 379.2 |
| B-15 | 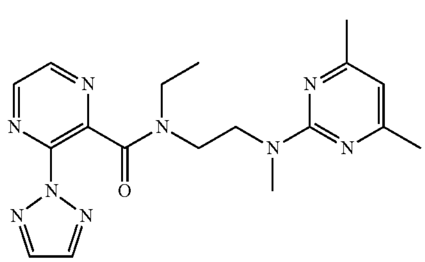 [SMILES: CCN(CCN(C)c1nc(C)cc(C)n1)C(=O)c1nccnc1-n1nccn1] | N-(2-((4,6-dimethylpyrimidin-2-yl)(methyl)amino)ethyl)-N-ethyl-3-(2H-1,2,3-triazol-2-yl)pyrazine-2-carboxamide | Calc'd 382.2, found 382.2 |

TABLE 1-continued

The following compounds were prepared according to the general procedure
provided in Example B and procedures herein, as described in the foregoing Reaction Schemes
and Examples. The requisite starting materials are either prepared as described in the
intermediates section, commercially available, or may be prepared from commercially available
reagents using conventional reactions well known in the art without undue experimentation.

| Ex. | Structure | Name | Mass [M + H] |
|---|---|---|---|
| B-16 | 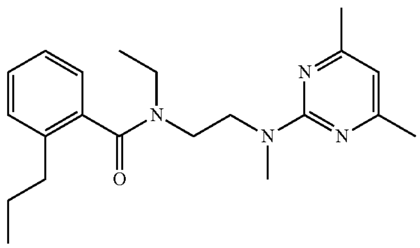 [SMILES: CCCc1ccccc1C(=O)N(CC)CCN(C)c1nc(C)cc(C)n1] | N-{2-[(4,6-dimethylpyrimidin-2-yl)(methyl)amino]ethyl}-N-ethyl-2-propylbenzamide | Calc'd 355.2, found 355.2 |
| B-17 | 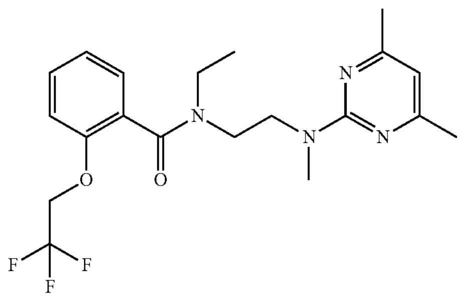 [SMILES: CCN(CCN(C)c1nc(C)cc(C)n1)C(=O)c1ccccc1OCC(F)(F)F] | N-{2-[(4, 6-dimethylpyrimidin-2-yl)(methyl)amino]ethyl}-N-ethyl-2-(2,2,2-trifluoroethoxy)-benzamide | Calc'd 411.2, found 411.2 |
| B-18 | 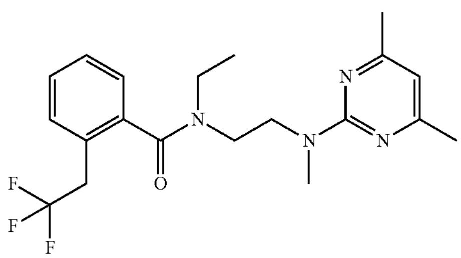 [SMILES: CCN(CCN(C)c1nc(C)cc(C)n1)C(=O)c1ccccc1CC(F)(F)F] | N-{2-[(4,6-dimethylpyrimidin-2-yl)(methyl)amino]ethyl}-N-ethyl-2-(2,2,2-trifluoroethyl)benzamide | Calc'd 395.2, found 395.2 |
| B-19 | 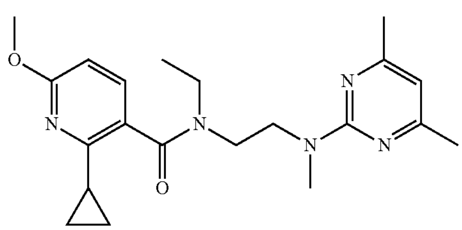 [SMILES: CCN(CCN(C)c1nc(C)cc(C)n1)C(=O)c1ccc(OC)nc1C1CC1] | 2-cyclopropyl-N-{2-[(4,6-dimethylpyrimidin-2-yl)(methyl)amino]ethyl}-N-ethyl-6-methoxypyridine-3-carboxamide | Calc'd 384.2, found 384.2 |
| B-20 | 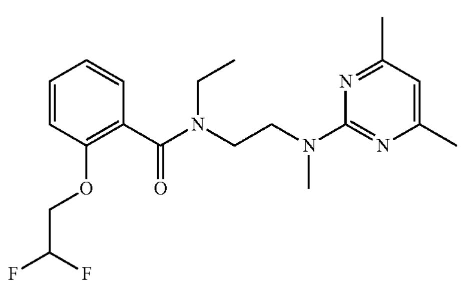 [SMILES: CCN(CCN(C)c1nc(C)cc(C)n1)C(=O)c1ccccc1OCC(F)F] | 2-(2,2-difluoroethoxy)-N-{2-[(4,6-dimethylpyrimidin-2-yl)(methyl)amino]ethyl}-N-ethylbenzamide | Calc'd 393.2, found 393.2 |

TABLE 1-continued

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-21 | 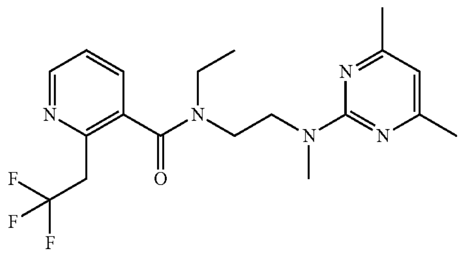 [SMILES: CCN(CCN(C)c1nc(C)cc(C)n1)C(=O)c1cccnc1CC(F)(F)F] | N-{2-[(4,6-dimethylpyrimidin-2-yl)(methyl)amino]ethyl}-N-ethyl-2-(2,2,2-trifluoroethyl)pyridine-3-carboxamide | Calc'd 396.2, found 396.2 |
| B-22 | 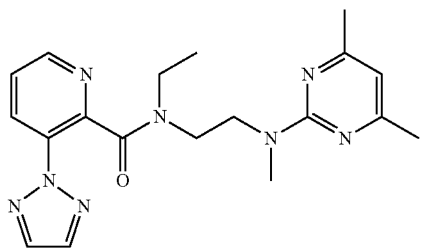 [SMILES: CCN(CCN(C)c1nc(C)cc(C)n1)C(=O)c1ncccc1-n1nccn1] | N-{2-[(4,6-dimethylpyrimidin-2-yl)(methyl)amino]ethyl}-N-ethyl-3-(2H-1,2,3-triazol-2-yl)pyridine-2-carboxamide | Calc'd 381.2, found 381.2 |
| B-23 | 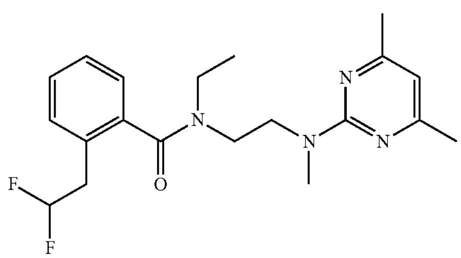 | 2-(2,2-difluoroethyl)-N-{2-[(4,6-dimethylpyrimidin-2-yl)(methyl)amino]ethyl}-N-ethylbenzamide | Calc'd 377.2, found 377.2 |
| B-24 | 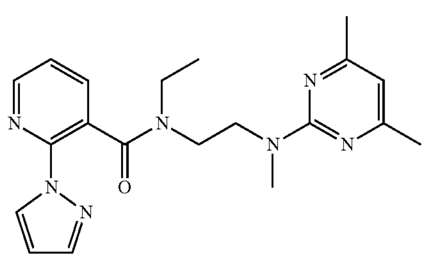 [SMILES: CCN(CCN(C)c1nc(C)cc(C)n1)C(=O)c1cccnc1-n1cccn1] | N-{2-[(4,6-dimethylpyrimidin-2-yl)(methyl)amino]ethyl}-N-ethyl-2-(1H-pyrazol-1-yl)pyridine-3-carboxamide | Calc'd 380.2, found 380.2 |
| B-25 | 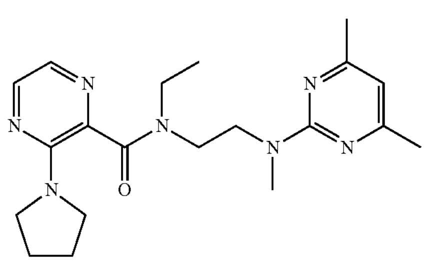 [SMILES: CCN(CCN(C)c1nc(C)cc(C)n1)C(=O)c1nccnc1N1CCCC1] | N-{2-[(4,6-dimethylpyrimidin-2-yl)(methyl)amino]ethyl}-N-ethyl-3-pyrrolidin-1-ylpyrazine-2-carboxamide | Calc'd 384.3, found 384.2 |

TABLE 1-continued

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-26 | 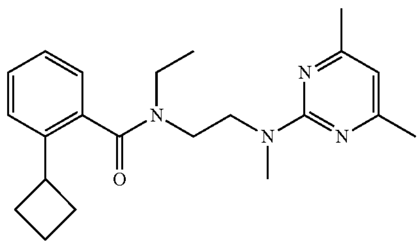 [SMILES: CCN(CCN(C)c1nc(C)cc(C)n1)C(=O)c1ccccc1C1CCC1] | 2-cyclobutyl-N-{2-[(4,6-dimethylpyrimidin-2-yl)(methyl)amino]ethyl}-N-ethylbenzamide | Calc'd 367.2, found 367.2 |
| B-27 | 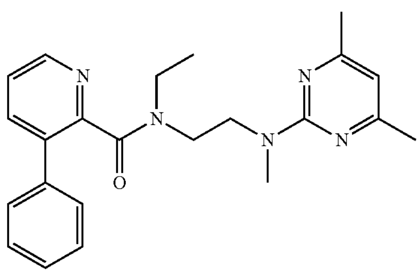 [SMILES: CCN(CCN(C)c1nc(C)cc(C)n1)C(=O)c1ncccc1-c1ccccc1] | N-{2-[(4,6-dimethylpyrimidin-2-yl)(methyl)amino]ethyl}-N-ethyl-3-phenylpyridine-2-carboxamide | Calc'd 390.2, found 390.2 |
| B-28 | 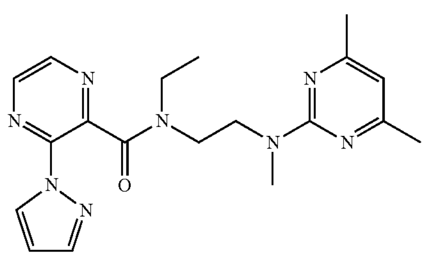 [SMILES: CCN(CCN(C)c1nc(C)cc(C)n1)C(=O)c1nccnc1-n1cccn1] | N-{2-[(4,6-dimethylpyrimidin-2-yl)(methyl)amino]ethyl}-N-ethyl-3-(1H-pyrazol-1-yl)pyrazine-2-carboxamide | Calc'd 381.2, found 381.2 |
| B-29 | 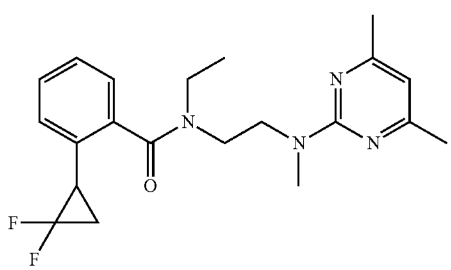 [SMILES: CCN(CCN(C)c1nc(C)cc(C)n1)C(=O)c1ccccc1C1CC1(F)F] | 2-(2,2-difluorocyclopropyl)-N-{2-[(4,6-dimethylpyrimidin-2-yl)(methyl)amino]ethyl}-N-ethylbenzamide | Calc'd 389.2, found 389.2 |
| B-30 | 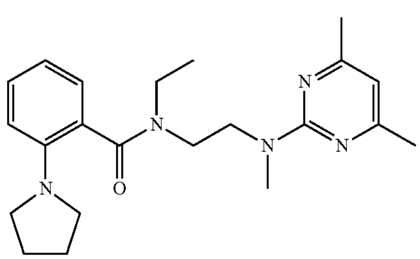 [SMILES: CCN(CCN(C)c1nc(C)cc(C)n1)C(=O)c1ccccc1N1CCCC1] | N-{2-[(4,6-dimethylpyrimidin-2-yl)(methyl)amino]ethyl}-N-ethyl-2-pyrrolidin-1-ylbenzamide | Calc'd 382.3, found 382.3 |

TABLE 1-continued

The following compounds were prepared according to the general procedure provided in Example B and procedures herein, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| B-31 | 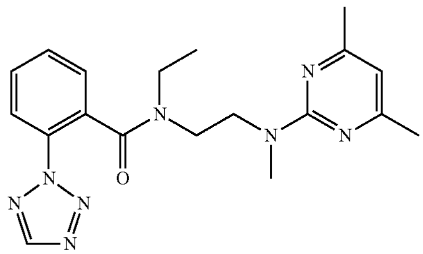 [SMILES: CCN(CCN(C)c1nc(C)cc(C)n1)C(=O)c1ccccc1-n1ncnn1] | N-{2-[(4,6-dimethylpyrimidin-2-yl)(methyl)amino]ethyl}-N-ethyl-2-(2H-tetrazol-2-yl)benzamide | Calc'd 381.2, found 381.2 |
| B-32 | 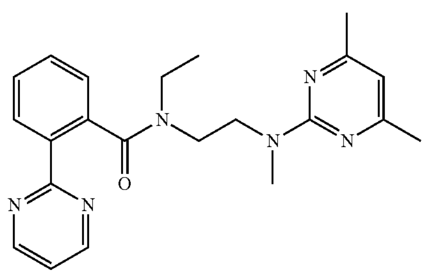 | N-{2-[(4,6-dimethylpyrimidin-2-yl)(methyl)amino]ethyl}-N-ethyl-2-pyrimidin-2-ylbenzamide | Calc'd 391.2, found 391.2 |
| B-33 | 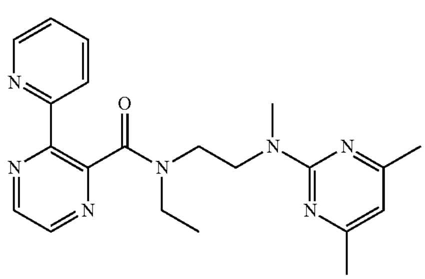 [SMILES: CCN(CCN(C)c1nc(C)cc(C)n1)C(=O)c1nccnc1-c1ccccn1] | N-{2-[(4,6-dimethylpyrimidin-2-yl)(methyl)amino]ethyl}-N-ethyl-3-pyridin-2-ylpyrazine-2-carboxamide | Calc'd 392.2, found 392.2 |

Example C

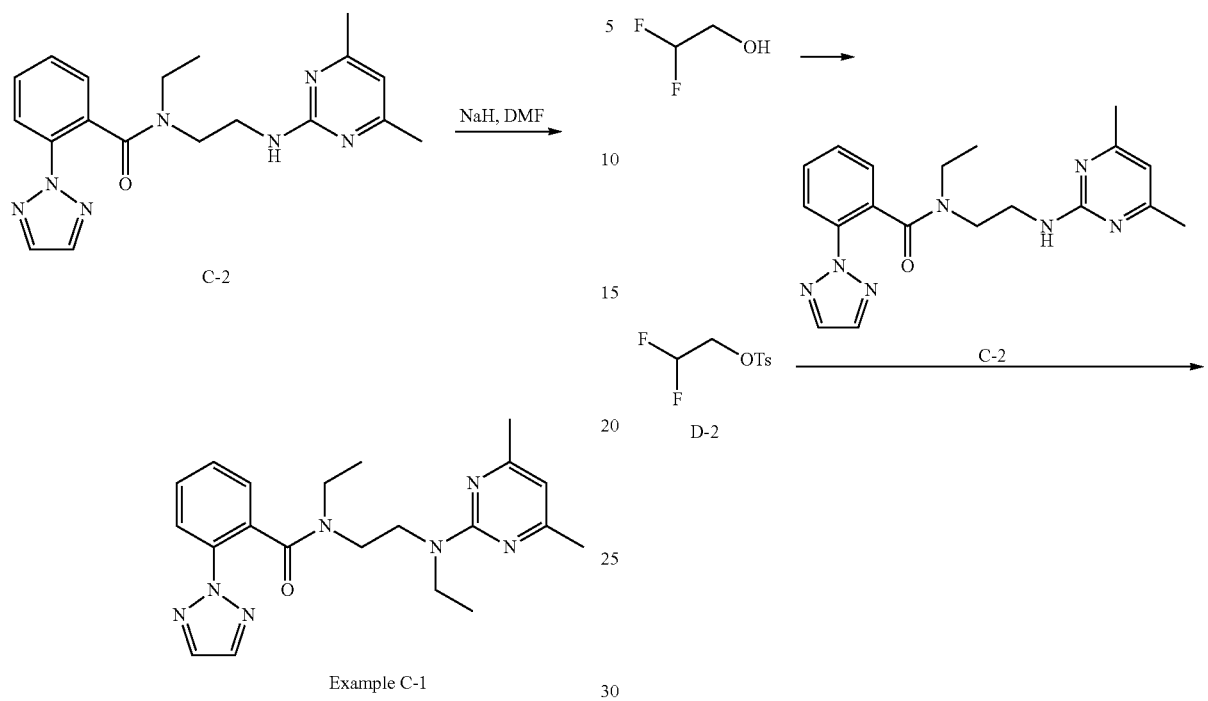

N-(2-((4,6-dimethylpyrimidin-2-yl)(ethyl)amino)ethyl)-N-ethyl-2-(2H-H-1,2,3-triazol-2-yl)benzamide (Example C-1)

To a solution of N-(2-((4,6-dimethylpyrimidin-2-yl)amino)ethyl)-N-ethyl-2-(2H-1,2,3-triazol-2-yl)benzamide (30 mg, 0.082 mmol, Example 1, step 4) in DMF (2 mL) was added NaH (6.57 mg, 0.164 mmol, 60% in oil) at 0° C. The mixture was stirred at 0° C. for 20 min and EtI (26 mg, 0.164 mmol) was added. The resulting mixture was stirred at 0° C. for 40 min, then quenched with water and filtered. The filtrate was purified by prep-HPLC to give the title compound. LRMS m/z (M+H) 394.1 found, 394.2 required.

Example D

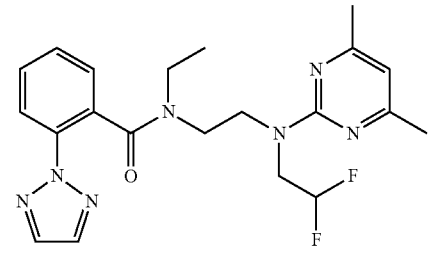

TABLE 2

The following compound was prepared according to the general procedure provided in Example C and procedures herein. The starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| C-3 | 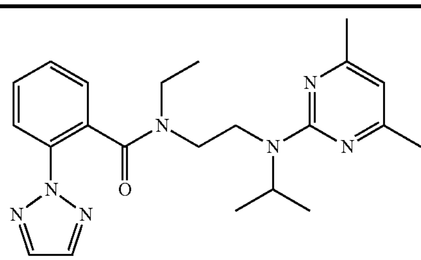 | N-(2-((4,6-dimethylpyrimidin-2-yl)(isopropyl)amino)ethyl)-N-ethyl-2-(2H-1,2,3-triazol-2-yl)benzamide | Calc'd 408.2, found 408.2 |

N-(2-((2,2-difluoroethyl)(4,6-dimethylpyrimidin-2-yl)amino)ethyl)-N-ethyl-2-(2H-1,2,3-triazol-2-yl)benzamide

Step 1: 2,2-difluoroethyl 4-methylbenzenesulfonate (D-2)

To a solution of 2,2-difluoroethanol (2 g, 24.2 mmol) in DCM (12 mL) was added TEA (10.2 mL, 73.2 mmol) at 0° C. The resulting mixture was stirred at 0° C. for 15 min and a solution of TsCl (5.58 g, 29.3 mmol) in DCM (15 mL) was added dropwise. The resulting mixture was stirred at RT for 2 h, then quenched with water (20 mL) and extracted with DCM (30 mL×3). The combined organic layers were washed with brine, dried over Na2SO4, filtered and the filtrate was concentrated in vacuo to give the title compound. LRMS m/z (M+H) 237.0 found, 237.0 required.

Step 2: N-(2-((2,2-difluoroethyl)(4,6-dimethylpyrimidin-2-yl)amino)ethyl)-N-ethyl-2-(2H-1,2,3-triazol-2-yl)benzamide (Example D-1)

To a solution of N-(2-((4,6-dimethylpyrimidin-2-yl)amino)ethyl)-N-ethyl-2-(2H-1,2,3-triazol-2-yl)benzamide (30 mg, 0.082 mmol, Example 1, step 4) in DMF (2 mL) was added NaH (6.57 mg, 0.16 mmol, 60% in oil) at 0° C. The mixture was stirred at 0° C. for 20 min and the product from step 1 (50 mg, 0.212 mmol) was added. The resulting mixture was stirred at 0° C. for 40 min, quenched with water and filtered. The filtrate was purified by prep-HPLC to give the title compound. LRMS m/z (M+H) 430.2 found, 430.2 required.

Example E

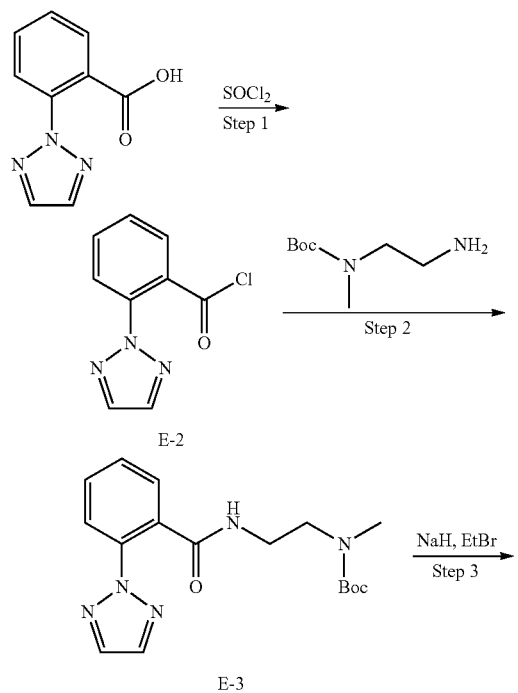

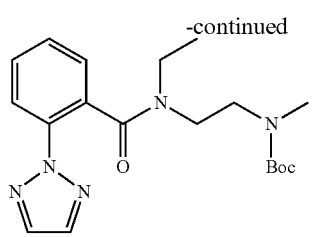

E-4

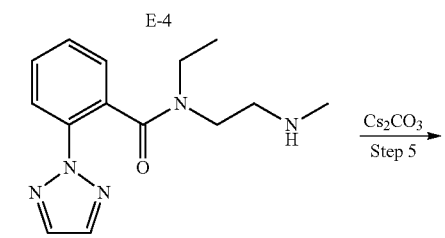

E-5

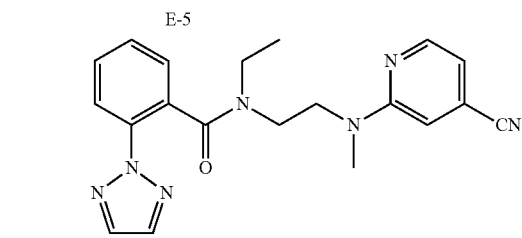

Example E-1

N-(2-((4-cyanopyridin-2-yl)(methyl)amino)ethyl)-N-ethyl-2-(2H-1,23-triazol-2-yl)benzamide

Step 1: 2-(2H-1,2,3-triazol-2-yl)benzoyl chloride (E-2)

Thionyl chloride (1.5 ml, 20.55 mmol) was added to a solution of 2-(2H-1,2,3-triazol-2-yl)benzoic acid (0.870 g, 4.6 mmol) in DCM at RT. The mixture was stirred for 10 minutes and concentrated to afford the title product without further purification.

Step 2: tert-butyl (2-(2-(2H-1,23-triazol-2-yl)benzamido)ethyl)(methyl)carbamate (E-3)

Tert-butyl (2-aminoethyl)(methyl)carbamate (800 mg, 4.59 mmol) was added to a 0° C. solution of Intermediate E-2 (955 mg, 4.60 mmol) and TEA (0.962 ml, 6.90 mmol) in THF. The mixture was then stirred at RT for 25 minutes, diluted with water, and extracted with EtOAc (3×50 mL). The combined organic layers were washed with brine, dried over MgSO4, filtered, and concentrated to afford the title compound without further purification.

Step 3: tert-butyl (2-(N-ethyl-2-(2H-1,2,3-triazol-2-yl)benzamido)ethyl)(methyl)carbamate (E-4)

NaH (0.45 g, 11.25 mmol) was added to a solution of Intermediate B (1.589 g, 4.60 mmol) in THF at 0° C. and stirred for 10 minutes. Bromoethane (1.1 ml, 14.74 mmol) was added and then the reaction was stirred at rt for 2 hours. LCMS showed only a little product with mainly SM. Additional DMF (10 ml) was added and the mixture was heated to 40° C. for 1 hour. The mixture was then diluted with water and extracted with EtOAc (3×50 mL). The combined organic layers were washed with water, brine, and dried over MgSO4. The mixture was then filtered, concentrated, and purified on RediSep 24 g eluting with 10-70% EtOAc/hexanes to afford the title compound.

Step 4: N-ethyl-N-(2-(methylamino)ethyl)-2-(2H-1,2,3-triazol-2-yl)benzamide (E-5)

HCl (3.0 ml, 12.00 mmol) was added to a solution of Intermediate E-4 (1.314 g, 3.52 mmol) in dioxane/water. The mixture was stirred at 40° C. for 24 hours and concentrated. The residue was dissolved in water and washed with ether twice. The aqueous solution was then lyophilized to afford the title compound.

Step 5: N-(2-((4-cyanopyridin-2-yl)(methyl)amino)ethyl)-N-ethyl-2-(2H-1,2,3-triazol-2-yl)benzamide (Example E-1)

Cesium carbonate (0.048 g, 0.146 mmol) was added to a mixture of N-ethyl-N-(2-(methylamino)ethyl)-2-(2H-1,2,3-triazol-2-yl)benzamide (0.020 g, 0.073 mmol) and intermediate E-5 in DMF (5 ml). The mixture was stirred at 100° C. for 1h in microwave. Residue was purified by preparative HPLC Reverse phase (C-18), eluting with Acetonitrile/Water+0.1% TFA, to give the title compound. LRMS m/z (M+H) 376.2 found, 376.2 required.

TABLE 3

The following compounds were prepared according to the general procedure provided in Example E-1 and procedures herein, but substituting the appropriate aryl fluoride or aryl chloride, as described in the foregoing Reaction Schemes and Examples. The starting materials are either prepared as described in the intermediates section, commercially available, or may be prepared from commercially available reagents using conventional reactions well known in the art without undue experimentation.

| Ex. | Structure | Name | Mass [M + H] | Method |
|---|---|---|---|---|
| E-7 | 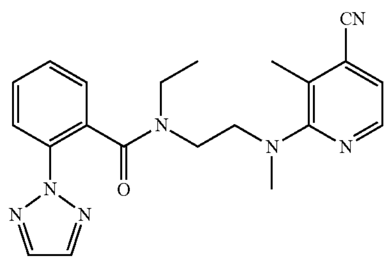 [SMILES: CCN(CCN(C)c1nccc(C#N)c1C)C(=O)c1ccccc1-n1nccn1] | N-(2-((4-cyano-3-methylpyridin-2-yl)(methyl)amino)ethyl)-N-ethyl-2-(2H-1,2,3-triazol-2-yl)benzamide | Calc'd 390.3, found 390.3 | A |
| E-8 | 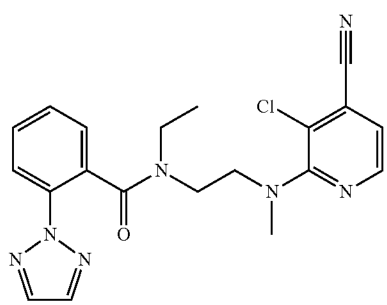 [SMILES: CCN(CCN(C)c1nccc(C#N)c1Cl)C(=O)c1ccccc1-n1nccn1] | N-{2-[(3-chloro-4-cyanopyridin-2-yl)(methyl)amino]ethyl}-N-ethyl-2-(2H-1,2,3-triazol-2-yl)benzamide | Calc'd 410.1, found 410.1 | A |
| E-9 | 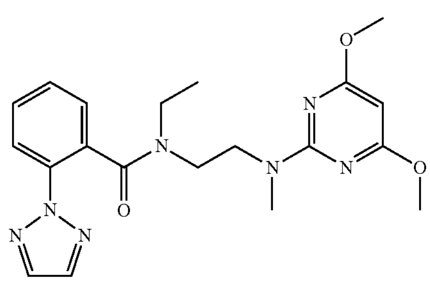 [SMILES: CCN(CCN(C)c1nc(OC)cc(OC)n1)C(=O)c1ccccc1-n1nccn1] | N-{2-[(4,6-dimethoxypyrimidin-2-yl)(methyl)amino]ethyl}-N-ethyl-2-(2H-1,2,3-triazol-2-yl)benzamide | Calc'd 412.2, found 412.2 | A |

TABLE 3-continued

The following compounds were prepared according to the general procedure provided in Example E-1 and procedures herein, but substituting the appropriate aryl fluoride or aryl chloride, as described in the foregoing Reaction Schemes and Examples. The starting materials are either prepared as described in the intermediates section, commercially available, or may be prepared from commercially available reagents using conventional reactions well known in the art without undue experimentation.

| Ex. | Structure | Name | Mass [M + H] | Method |
|---|---|---|---|---|
| E-10 | 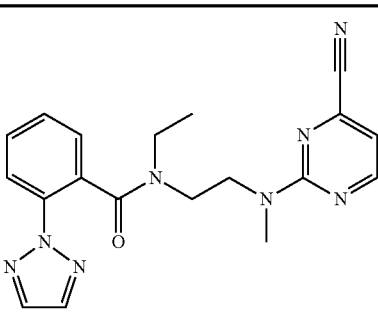 | N-{2-[(4-cyanopyrimidin-2-yl)(methyl)amino]ethyl}-N-ethyl-2-(2H-1,2,3-triazol-2-yl)benzamide | Calc'd 377.2, found 377.2 | A |
| E-11 | 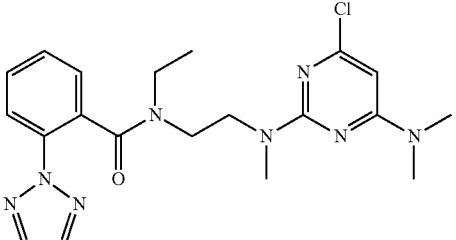 | N-(2-{[4-chloro-6-(dimethylamino)pyrimidin-2-yl](methyl)amino}ethyl)-N-ethyl-2-(2H-1,2,3-triazol-2-yl)benzamide | Calc'd 429.2, found 429.2 | A |
| E-14 | 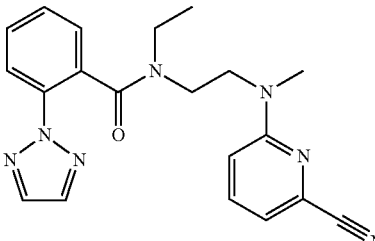 | N-{2-[(6-cyanopyridin-2-yl)(methyl)amino]ethyl}-N-ethyl-2-(2H-1,2,3-triazol-2-yl)benzamide | Calc'd 376.2, found 376.2 | B |
| E-16 | 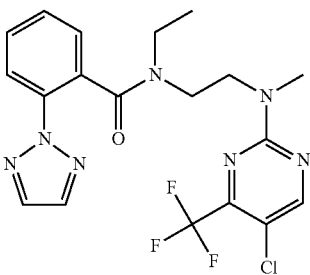 [SMILES: CCN(CCN(C)c1ncc(Cl)c(C(F)(F)F)n1)C(=O)c1ccccc1-n1nccn1] | N-(2-{[5-chloro-4-(trifluoromethyl)pyrimidin-2-yl](methyl)amino}ethyl)-N-ethyl-2-(2H-1,2,3-triazol-2-yl)benzamide | Calc'd 454.1, found 454.1 | B |
| E-22 | 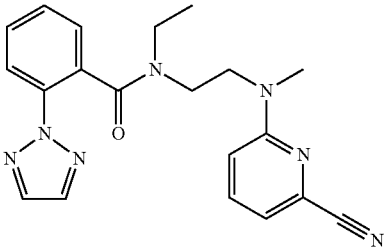 [SMILES: CCN(CCN(C)c1cccc(C#N)n1)C(=O)c1ccccc1-n1nccn1] | N-{2-[(6-cyanopyridin-2-yl)(methyl)amino]ethyl}-N-ethyl-2-(2H-1,2,3-triazol-2-yl)benzamide | Calc'd 376.2, found 376.2 | B |

Example F

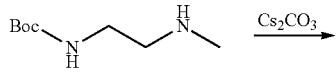

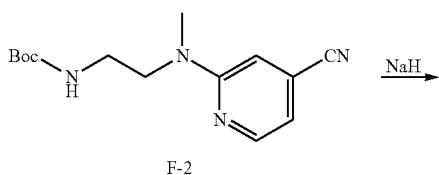

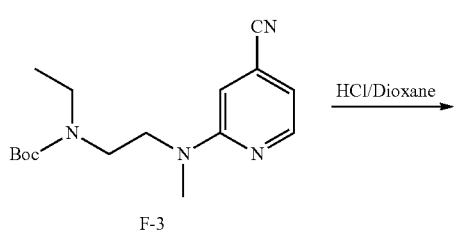

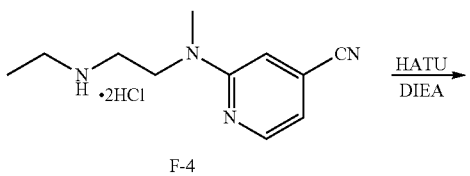

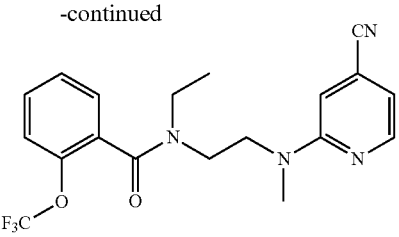

Example F-1

{2-[(4-cyanopyridin-2-yl)(methyl)amino]ethyl}-N-ethyl-2-(trifluoromethoxy)benzamide

Step 1: tert-butyl (2-((4-cyanopyridin-2-yl)(methyl)amino)ethyl)carbamate (F-2)

To a solution of tert-butyl (2-(methylamino)ethyl)carbamate hydrochloride (1.55 g, 7.36 mmol) and 2-fluoroisonicotinonitrile (1.80 g, 14.71 mmol) in 40 mL of DMF at room temperature was added $Cs_2CO_3$ (7.19 g, 22.07 mmol). The mixture was stirred at 110° C. overnight, cooled to room temperature, and filtered. The filtrate was concentrated under vacuum and the resulting residue was purified by silica gel chromatography using a 0% to 50% EtOAc in hexanes gradient to give the title product.

Step 2: tert-butyl (2-((4-cyanopyridin-2-yl)(methyl)amino)ethyl)(ethyl)carbamate (F-3)

To a suspension of NaH (0.598 g, 14.95 mmol) in DMF (40 mL) at 0° C. was added dropwise a solution of the intermediate from Step A (2.95 g, 0.484 mmol) in DMF (20 mL). The reaction mixture was stirred at room temperature for 10 minutes and EtI (3.00 g, 19.22 mmol) was added. The resulting mixture was stirred at room temperature overnight and quenched with saturated aqueous $NH_4Cl$ solution (30 mL). The mixture was extrated with EtOAc (40 mL×2). The organic layers were combined, washed with brine, dried with $MgSO_4$, filtered, and concentrated in vacuo. The crude product was purified by silica gel chromatography using a 0% to 30% EtOAc in hexanes gradient to give the title compound.

Step 3: 2-((2-(ethylamino)ethyl)(methyl)amino)isonicotinonitrile hydrochloride (F-4)

To the intermediate from Step B (2.62 g, 8.61 mmol) in 1,4-dioxane (30 mL) was added concentrated aqueous HCl solution dropwise. The mixture was stirred at room temperature for 1.5 hours and concentrated vacuum to give the title compound. m/z=205 (M+1).

Step 4: -{2-[(4-cyanopyridin-2-yl)(methyl)amino]ethyl}-N-ethyl-2-(trifluoromethoxy)benzamide (F-1)

To a solution of compound F-4 (0.1 g, 0.42 mmol) and 2-trifluoromethoxybenzoic acid (0.084 g, 0.42 mmol) in DCM (5 mL) was added HATU (0.17 g, 4.50 mmol), DIPEA (0.060 g, 0.43 mmol) successively. The solution was stirred at RT for 9 h under $N_2$, then poured into water (30 mL), and extracted with DCM (20 mL×3). The combined organic layers were washed with brine (30 mL), dried over $Na_2SO_4$, filtered, and concentrated in vacuo. The residue was purified by column chromatography (petroleumether:EtOAc=7:1 to 2:1) to give the title compound F-1 (0.15 g). LCMS m/z (M+H) 393.2 found, 393.2 required.

TABLE 4

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-5 | 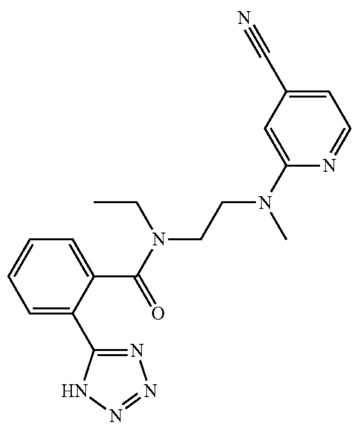 [SMILES: CCN(CCN(C)c1cc(C#N)ccn1)C(=O)c1ccccc1-c1nnn[nH]1] | N-{2-[(4-cyanopyridin-2-yl)(methyl)amino]ethyl}-N-ethyl-2-(1H-tetrazol-5-yl)benzamide | Calc'd 377.2, found 377.2 |
| F-6 | 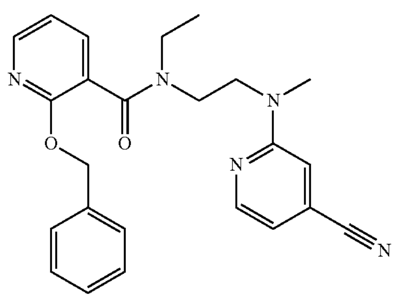 [SMILES: CCN(CCN(C)c1cc(C#N)ccn1)C(=O)c1cccnc1OCc1ccccc1] | 2-(benzyloxy)-N-{2-[(4-cyanopyridin-2-yl)(methyl)amino]ethyl}-N-ethylpyridine-3-carboxamide | Calc'd 416.2, found 416.2 |
| F-7 | 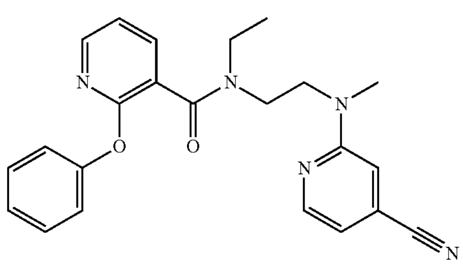 [SMILES: CCN(CCN(C)c1cc(C#N)ccn1)C(=O)c1cccnc1Oc1ccccc1] | N-{2-[(4-cyanopyridin-2-yl)(methyl)amino]ethyl}-N-ethyl-2-phenoxypyridine-3-carboxamide | Calc'd 402.2, found 402.2 |
| F-8 | 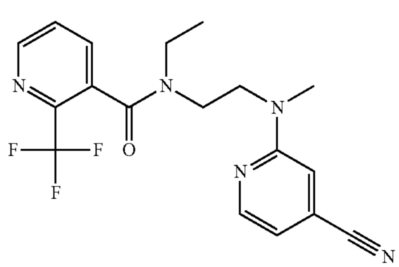 [SMILES: CCN(CCN(C)c1cc(C#N)ccn1)C(=O)c1cccnc1C(F)(F)F] | N-{2-[(4-cyanopyridin-2-yl)(methyl)amino]ethyl}-N-ethyl-2-(trifluoromethyl)pyridine-3-carboxamide | Calc'd 378.2, found 378.2 |

TABLE 4-continued

The following compounds were prepared according to the general procedure
provided in Example F-1 and procedures herein, but substituting the appropriate aryl amide, as
described in the foregoing Reaction Schemes and Examples. The requisite starting materials are
either prepared as described in the intermediates section, commercially available, or may be
prepared from commercially available reagents using conventional reactions well known in the
art without undue experimentation.

| Ex. | Structure | Name | Mass [M + H] |
|---|---|---|---|
| F-9 | 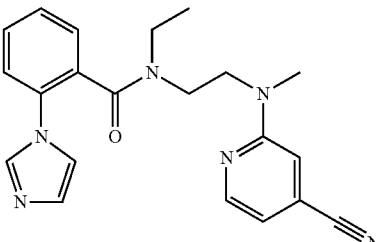 | N-{2-[(4-cyanopyridin-2-yl)(methyl)amino]ethyl}-N-ethyl-2-(1H-imidazol-1-yl)benzamide | Calc'd 375.2, found 375.2 |
| F-10 | 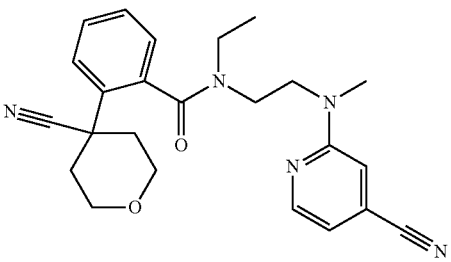 [SMILES: CCN(CCN(C)c1cc(C#N)ccn1)C(=O)c1ccccc1C1(C#N)CCOCC1] | N-{2-[(4-cyanopyridin-2-yl)(methyl)amino]ethyl}-2-(4-cyanotetrahydro-2H-pyran-4-yl)-N-ethylbenzamide | Calc'd 418.2, found 418.2 |
| F-11 | 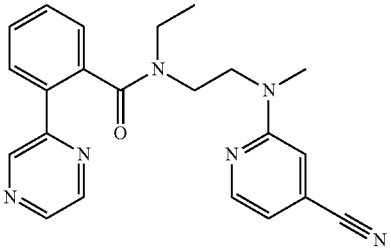 [SMILES: CCN(CCN(C)c1cc(C#N)ccn1)C(=O)c1ccccc1-c1cnccn1] | N-{2-[(4-cyanopyridin-2-yl)(methyl)amino]ethyl}-N-ethyl-2-pyrazin-2-ylbenzamide | Calc'd 387.2, found 387.2 |
| F-12 | 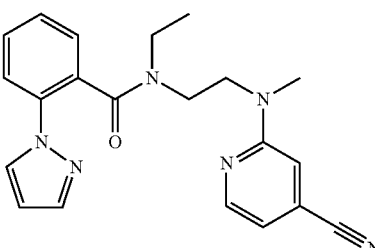 | N-{2-[(4-cyanopyridin-2-yl)(methyl)amino]ethyl}-N-ethyl-2-(1H-pyrazol-1-yl)benzamide | Calc'd 375.2, found 375.2 |
| F-13 | 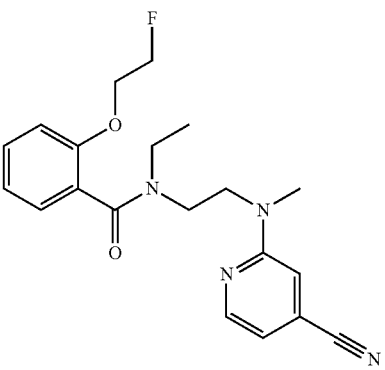 [SMILES: CCN(CCN(C)c1cc(C#N)ccn1)C(=O)c1ccccc1OCCF] | N-{2-[(4-cyanopyridin-2-yl)(methyl)amino]ethyl}-N-ethyl-2-(2-fluoroethoxy)benzamide | Calc'd 371.2, found 371.2 |

TABLE 4-continued

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-14 | 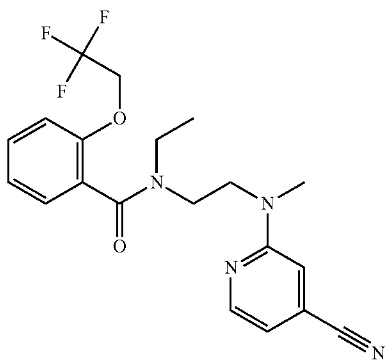 [SMILES: CCN(CCN(C)c1cc(C#N)ccn1)C(=O)c1ccccc1OCC(F)(F)F] | N-{2-[(4-cyanopyridin-2-yl)(methyl)amino]ethyl}-N-ethyl-2-(2,2,2-trifluoroethoxy)benzamide | Calc'd 407.2, found 407.2 |
| F-15 | 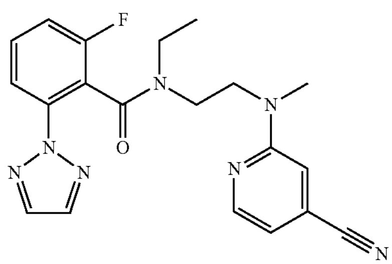 [SMILES: CCN(CCN(C)c1cc(C#N)ccn1)C(=O)c1c(F)cccc1-n1nccn1] | N-{2-[(4-cyanopyridin-2-yl)(methyl)amino]ethyl}-N-ethyl-2-fluoro-6-(2H-1,2,3-triazol-2-yl)benzamide | Calc'd 394.2, found 394.2 |
| F-16 | 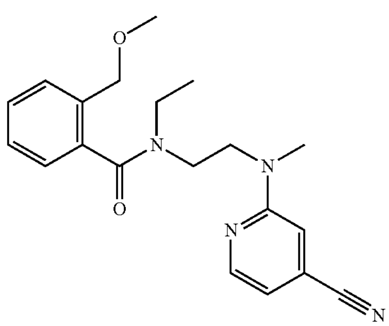 [SMILES: CCN(CCN(C)c1cc(C#N)ccn1)C(=O)c1ccccc1COC] | N-{2-[(4-cyanopyridin-2-yl)(methyl)amino]ethyl}-N-ethyl-2-(methoxymethyl)benzamide | Calc'd 353.2, found 353.2 |
| F-17 | 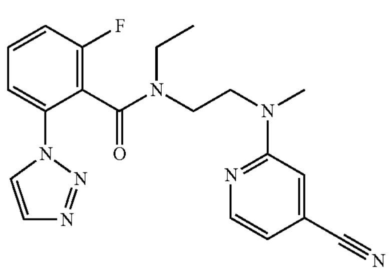 [SMILES: CCN(CCN(C)c1cc(C#N)ccn1)C(=O)c1c(F)cccc1-n1ccnn1] | N-{2-[(4-cyanopyridin-2-yl)(methyl)amino]ethyl}-N-ethyl-2-fluoro-6-(1H-1,2,3-triazol-1-yl)benzamide | Calc'd 394.2, found 394.2 |

TABLE 4-continued

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-18 | 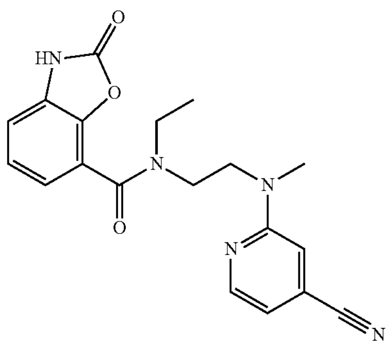 [SMILES: CCN(CCN(C)c1cc(C#N)ccn1)C(=O)c1cccc2[nH]c(=O)oc12] | N-{2-[(4-cyanopyridin-2-yl)(methyl)amino]ethyl}-N-ethyl-2-oxo-2,3-dihydro-1,3-benzoxazole-7-carboxamide | Calc'd 366.2, found 366.2 |
| F-19 | 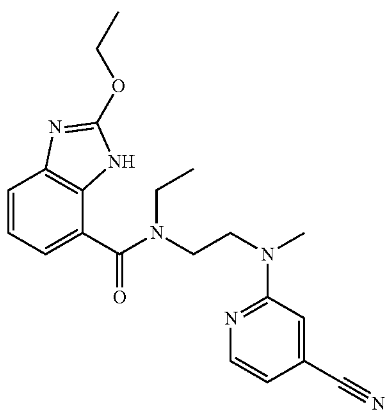 [SMILES: CCOc1nc2cccc(C(=O)N(CC)CCN(C)c3cc(C#N)ccn3)c2[nH]1] | N-{2-[(4-cyanopyridin-2-yl)(methyl)amino]ethyl}-2-ethoxy-N-ethyl-1H-benzimidazole-7-carboxamide | Calc'd 393.2, found 393.2 |
| F-20 | 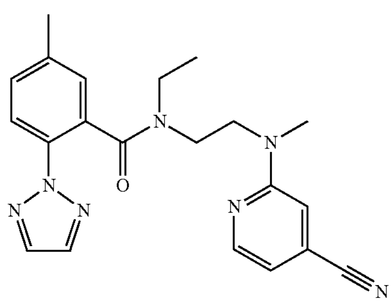 [SMILES: CCN(CCN(C)c1cc(C#N)ccn1)C(=O)c1cc(C)ccc1-n1nccn1] | N-{2-[(4-cyanopyridin-2-yl)(methyl)amino]ethyl}-N-ethyl-5-methyl-2-(2H-1,2,3-triazol-2-yl)benzamide | Calc'd 390.2, found 390.2 |
| F-21 | 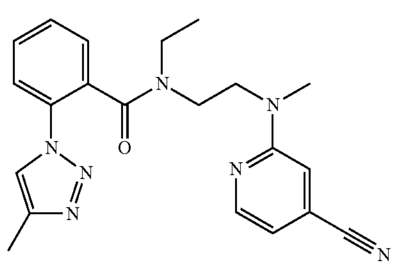 [SMILES: CCN(CCN(C)c1cc(C#N)ccn1)C(=O)c1ccccc1-n1cc(C)nn1] | N-{2-[(4-cyanopyridin-2-yl)(methyl)amino]ethyl}-N-ethyl-2-(4-methyl-1H-1,2,3-triazol-1-yl)benzamide | Calc'd 390.2, found 390.2 |

TABLE 4-continued

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-22 | 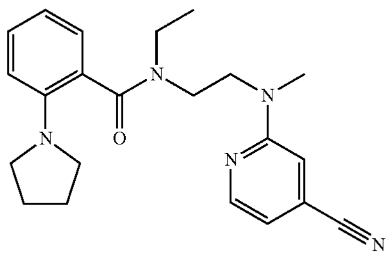 [SMILES: CCN(CCN(C)c1cc(C#N)ccn1)C(=O)c1ccccc1N1CCCC1] | N-{2-[(4-cyanopyridin-2-yl)(methyl)amino]ethyl}-N-ethyl-2-pyrrolidin-1-ylbenzamide | Calc'd 378.2, found 378.2 |
| F-23 | 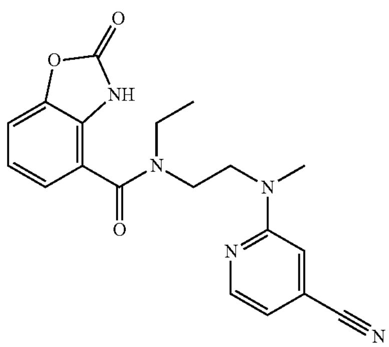 [SMILES: CCN(CCN(C)c1cc(C#N)ccn1)C(=O)c1cccc2oc(=O)[nH]c12] | N-{2-[(4-cyanopyridin-2-yl)(methyl)amino]ethyl}-N-ethyl-2-oxo-2,3-dihydro-1,3-benzoxazole-4-carboxamide | Calc'd 366.2, found 366.2 |
| F-24 | 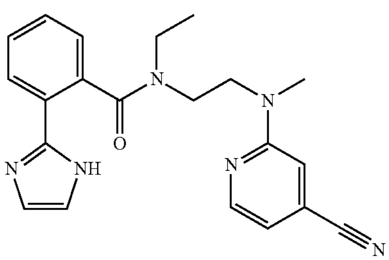 [SMILES: CCN(CCN(C)c1cc(C#N)ccn1)C(=O)c1ccccc1-c1ncc[nH]1] | N-{2-[(4-cyanopyridin-2-yl)(methyl)amino]ethyl}-N-ethyl-2-(1H-imidazol-2-yl)benzamide | Calc'd 375.2, found 375.2 |
| F-25 | 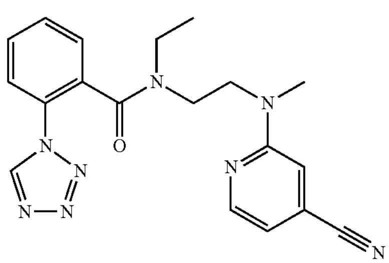 [SMILES: CCN(CCN(C)c1cc(C#N)ccn1)C(=O)c1ccccc1-n1cnnn1] | N-{2-[(4-cyanopyridin-2-yl)(methyl)amino]ethyl}-N-ethyl-2-(1H-tetrazol-1-yl)benzamide | Calc'd 377.2, found 377.2 |
| F-26 | 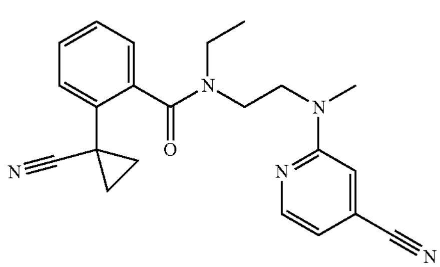 [SMILES: CCN(CCN(C)c1cc(C#N)ccn1)C(=O)c1ccccc1C1(C#N)CC1] | 2-(1-cyanocyclopropyl)-N-{2-[(4-cyanopyridin-2-yl)(methyl)amino]ethyl}-N-ethylbenzamide | Calc'd 374.2, found 374.2 |

TABLE 4-continued

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-27 | 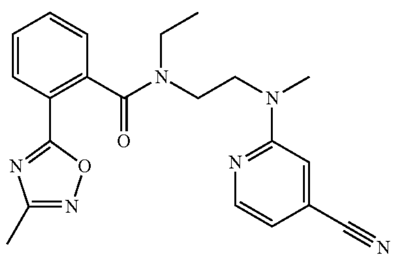 [SMILES: CCN(CCN(C)c1cc(C#N)ccn1)C(=O)c1ccccc1-c1nc(C)no1] | N-{2-[(4-cyanopyridin-2-yl)(methyl)amino]ethyl}-N-ethyl-2-(3-methyl-1,2,4-oxadiazol-5-yl)benzamide | Calc'd 391.2, found 391.2 |
| F-28 | 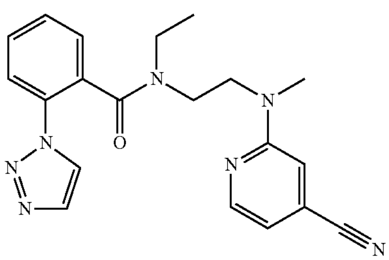 [SMILES: CCN(CCN(C)c1cc(C#N)ccn1)C(=O)c1ccccc1-n1ccnn1] | N-{2-[(4-cyanopyridin-2-yl)(methyl)amino]ethyl}-N-ethyl-2-(1H-1,2,3-triazol-1-yl)benzamide | Calc'd 376.2, found 376.2 |
| F-29 | 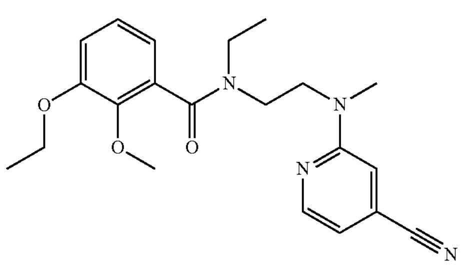 [SMILES: CCOc1cccc(C(=O)N(CC)CCN(C)c2cc(C#N)ccn2)c1OC] | N-{2-[(4-cyanopyridin-2-yl)(methyl)amino]ethyl}-3-ethoxy-N-ethyl-2-methoxybenzamide | Calc'd 383.2, found 383.2 |
| F-30 | 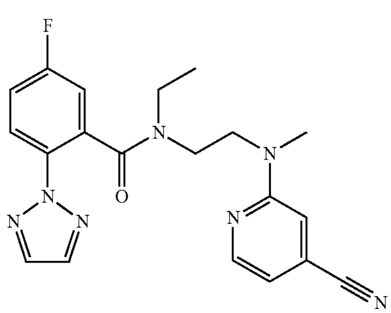 [SMILES: CCN(CCN(C)c1cc(C#N)ccn1)C(=O)c1cc(F)ccc1-n1nccn1] | N-{2-[(4-cyanopyridin-2-yl)(methyl)amino]ethyl}-N-ethyl-5-fluoro-2-(2H-1,2,3-triazol-2-yl)benzamide | Calc'd 394.2, found 394.2 |

TABLE 4-continued

The following compounds were prepared according to the general procedure provided in Example F-1 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| F-31 | 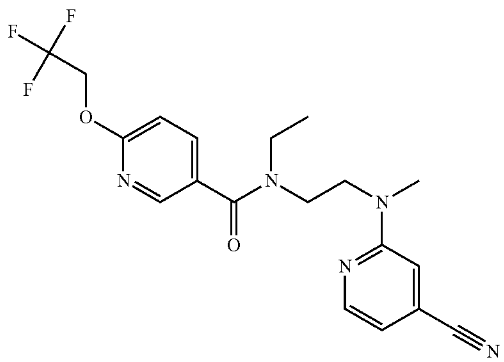 [SMILES: CCN(CCN(C)c1cc(C#N)ccn1)C(=O)c1ccc(OCC(F)(F)F)nc1] | N-{2-[(4-cyanopyridin-2-yl)(methyl)amino]ethyl}-N-ethyl-6-(2,2,2-trifluoroethoxy)pyridine-3-carboxamide | Calc'd 408.2, found 408.2 |

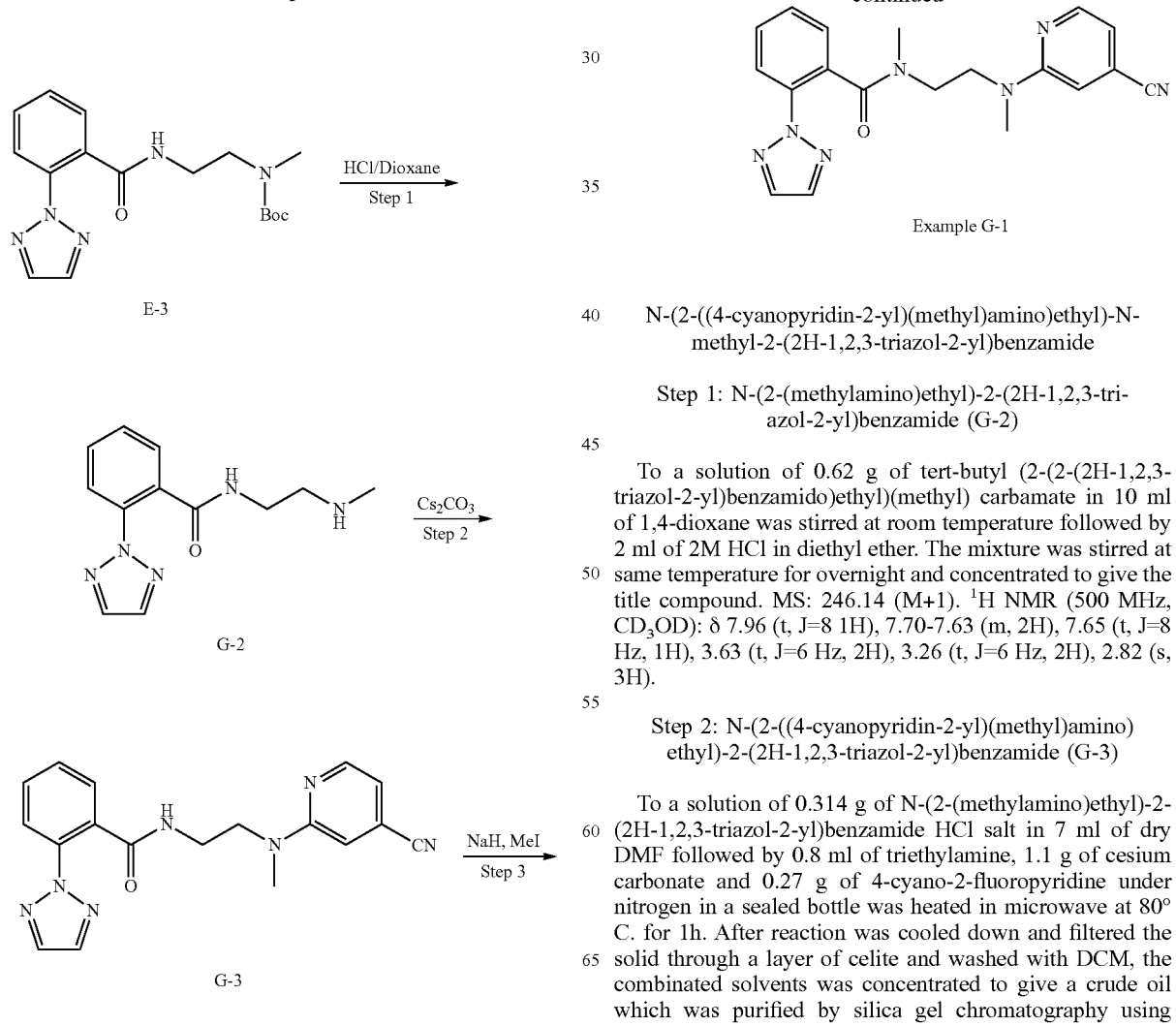

Example G

Example G-1

N-(2-((4-cyanopyridin-2-yl)(methyl)amino)ethyl)-N-methyl-2-(2H-1,2,3-triazol-2-yl)benzamide Step 1: N-(2-(methylamino)ethyl)-2-(2H-1,2,3-triazol-2-yl)benzamide (G-2)

To a solution of 0.62 g of tert-butyl (2-(2-(2H-1,2,3-triazol-2-yl)benzamido)ethyl)(methyl) carbamate in 10 ml of 1,4-dioxane was stirred at room temperature followed by 2 ml of 2M HCl in diethyl ether. The mixture was stirred at same temperature for overnight and concentrated to give the title compound. MS: 246.14 (M+1). $^1$H NMR (500 MHz, CD$_3$OD): δ 7.96 (t, J=8 1H), 7.70-7.63 (m, 2H), 7.65 (t, J=8 Hz, 1H), 3.63 (t, J=6 Hz, 2H), 3.26 (t, J=6 Hz, 2H), 2.82 (s, 3H).

Step 2: N-(2-((4-cyanopyridin-2-yl)(methyl)amino)ethyl)-2-(2H-1,2,3-triazol-2-yl)benzamide (G-3)

To a solution of 0.314 g of N-(2-(methylamino)ethyl)-2-(2H-1,2,3-triazol-2-yl)benzamide HCl salt in 7 ml of dry DMF followed by 0.8 ml of triethylamine, 1.1 g of cesium carbonate and 0.27 g of 4-cyano-2-fluoropyridine under nitrogen in a sealed bottle was heated in microwave at 80° C. for 1h. After reaction was cooled down and filtered the solid through a layer of celite and washed with DCM, the combinated solvents was concentrated to give a crude oil which was purified by silica gel chromatography using 0-30% of MeOH and DCM to afford the title product. MS: 348.26 (M+1). ¹H NMR (500 MHz, CD₃OD): δ 8.22-8.14 (m, 1H), 7.98 (s, 1H), 7.94-7.83 (m, 3H), 7.61 (t, J=8 Hz, 1H), 7.47 (t, J=8 Hz, 1H), 7.39 (d, J=7.7 Hz, 1H), 6.97 (s, 1H), 6.77 (d, J=5.1 Hz, 1H), 3.77 (t, J=6.4 Hz, 2H), 3.51 (t, J=6.4 Hz, 2H), 3.13 (s, 3H).

Step 3: N-(2-((4-cyanopyridin-2-yl)(methyl)amino)ethyl)-N-methyl-2-(2H-1,2,3-triazol-2-yl)benzamide (Example G-1)

To a solution of 45 mg of N-(2-((4-cyanopyridin-2-yl)(methyl)amino)ethyl)-2-(2H-1,2,3-triazol-2-yl)benzamide in 0.5 ml of DMF was treated with 27.6 mg of iodomethane and 7.7 mg of sodium hydride under nitrogen. The mixture was stirred at room temperature for overnight. After reaction was completed, residue was purified by preparative HPLC Reverse phase (C-18), eluting with Acetonitrile/Water+0.1% TFA to give the title compound G- as a TFA salt. MS: 362.16 (M+1). ¹H NMR (500 MHz, CDCl₃): δ 8.30-8.24 (m, 1H), 8.10-8.04 (m, 1H), 7.83 (s, 2H), 7.60 (t, J=8 Hz, 1H), 7.46 (t, J=8, 1H), 7.35-7.24 (m, 2H), 6.94-6.70 (m, 1H), 6.53 (s, 1H), 4.30-3.98 (bs, 2H), 3.81-3.72 (bs, 2H), 3.35 (S, 3H), 2.83 (S, 3H).

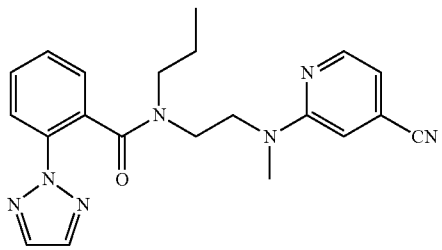 [SMILES: CCCN(CCN(C)c1cc(C#N)ccn1)C(=O)c1ccccc1-n1nccn1]

N-(2-((4-cyanopyridin-2-yl)(methyl)amino)ethyl)-N-propyl-2-(2H-1,2,3-triazol-2-yl)benzamide (Example G-4)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 14.7 mg of 1-iodopropane and 3.5 mg of sodium hydride under nitrogen. The mixture was stirred at room temperature for over night. After reaction was completed, residue was purified by preparative HPLC Reverse phase (C-18), eluting with Acetonitrile/Water+0.1% TFA to give the title compound G-4 as a TFA salt. LCMS: 390.25 (M+1).

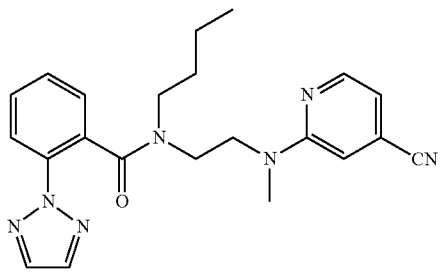 [SMILES: CCCCN(CCN(C)c1cc(C#N)ccn1)C(=O)c1ccccc1-n1nccn1]

N-butyl-N-(2-((4-cyanopyridin-2-yl)(methyl)amino)ethyl)-2-(2H-1,2,3-triazol-2-yl)benzamide (Example G-5)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 15.9 mg of 1-Iodobutane and 3.5 mg of Sodium hydride under nitrogen. The mixture was stirred at room temperature for over night. After reaction was completed, residue was purified by preparative HPLC Reverse phase (C-18), eluting with Acetonitrile/Water+0.1% TFA to give the title compound G-5 as a TFA salt. LCMS: 404.26 (M+1).

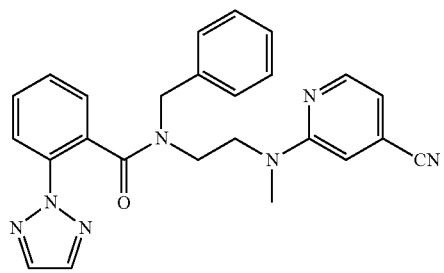 [SMILES: CN(CCN(Cc1ccccc1)C(=O)c1ccccc1-n1nccn1)c1cc(C#N)ccn1]

N-benzyl-N-(2-((4-cyanopyridin-2-yl)(methyl)amino)ethyl)-2-(2H-1,2,3-triazol-2-yl)benzamide (Example G-6)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 14.8 mg of benzyl bromide and 3.5 mg of sodium hydride under nitrogen. The mixture was stirred at room temperature for over night. After reaction was completed, residue was purified by preparative HPLC Reverse phase (C-18), eluting with Acetonitrile/Water+0.1% TFA to give the title compound G-6 as a TFA salt. LCMS: 438.27 (M+1).

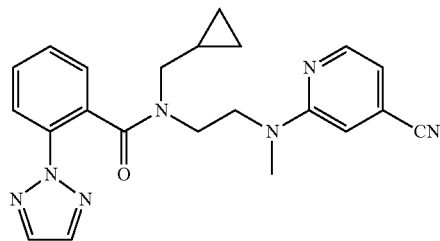 [SMILES: CN(CCN(CC1CC1)C(=O)c1ccccc1-n1nccn1)c1cc(C#N)ccn1]

N-(2-((4-cyanopyridin-2-yl)(methyl)amino)ethyl)-N-(cycloproplmethyl)-2-(2H-1,2,3-triazol-2-yl)benzamide (Example G-7)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 15.7 mg of (iodomethyl)cyclopropane and 3.5 mg of Sodium hydride under nitrogen. The mixture was stirred at room temperature for over night. Reaction was completed. After reaction was completed, residue was purified by preparative HPLC Reverse phase (C-18), eluting with Acetonitrile/Water+0.1% TFA to give the title compound G-7 as a TFA salt. LCMS: 402.29 (M+1).

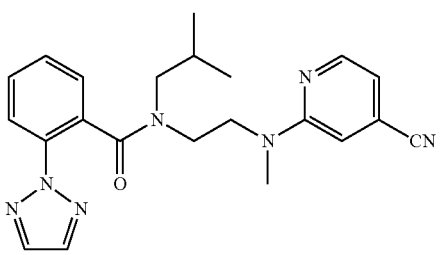 [SMILES: CC(C)CN(CCN(C)c1cc(C#N)ccn1)C(=O)c1ccccc1-n1nccn1]

N-(2-((4-cyanopyridin-2-yl)(methyl)amino)ethyl)-N-isobutyl-2-(2H-1,2,3-triazol-2-yl)benzamide (Example G-8)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 21.2 mg of 1-Iodo-2-methylpropane and 37.5 mg of cesium carbonate under nitrogen. The mixture was heated at 50° C. for 3 days. After reaction was completed, residue was purified by preparative HPLC Reverse phase (C-18), eluting with Acetonitrile/Water+0.1% TFA to give the title compound G-8 as a TFA salt. LCMS: 404.34 (M+1).

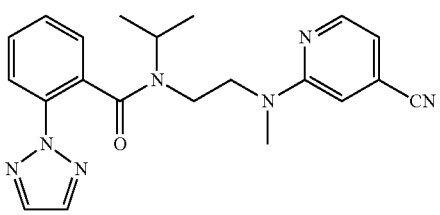 [SMILES: CC(C)N(CCN(C)c1cc(C#N)ccn1)C(=O)c1ccccc1-n1nccn1]

N-(2-((4-cyanopyridin-2-yl)(methyl)amino)ethyl)-N-isopropyl-2-(2H-1,2,3-triazol-2-yl)benzamide (Example G-9)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 14.7 mg of 2-Iodopropane and 3.5 mg of Sodium hydride under nitrogen. The mixture was heated at 50° C. for 3 days After reaction was completed, residue was purified by preparative HPLC Reverse phase (C-18), eluting with Acetonitrile/Water+0.1% TFA to give the title compound G-9 as a TFA salt. LCMS: 390.23 (M+1).

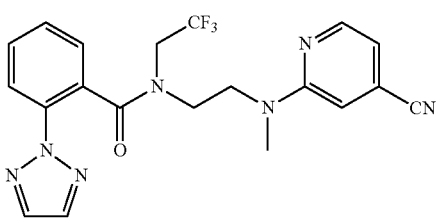 [SMILES: CN(CCN(CC(F)(F)F)C(=O)c1ccccc1-n1nccn1)c1cc(C#N)ccn1]

N-(2-((4-cyanopyridin-2-yl)(methyl)amino)ethyl)-2-(2H-1,2,3-triazol-2-yl)-N-(2,2,2-trifluoroethyl)benzamide (Example G-10)

To a solution of 20 mg of N-(2-((4-cyanopyridin-2-yl)(methyl)amino)ethyl)-2-(2H-1,2,3-triazol-2-yl)benzamide in 0.4 ml of DMF was treated with 24.2 mg of 2-Iodo-1,1,1-trifluoroethane and 37.5 mg of Cesium Carbonate under nitrogen. The mixture was heated at 50° C. for 3 days. After reaction was completed, residue was purified by preparative HPLC Reverse phase (C-18), eluting with Acetonitrile/Water+0.1% TFA to give the title compound G- as a TFA salt. LCMS: 430.98 (M+1).

Example H

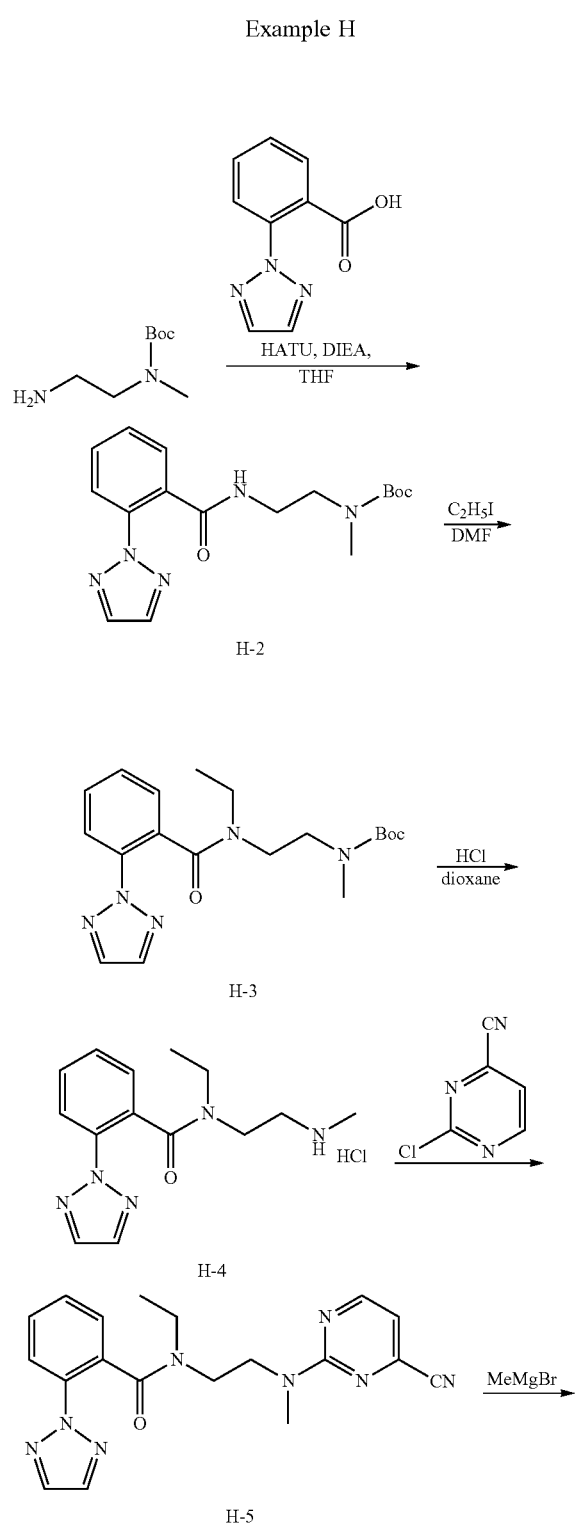

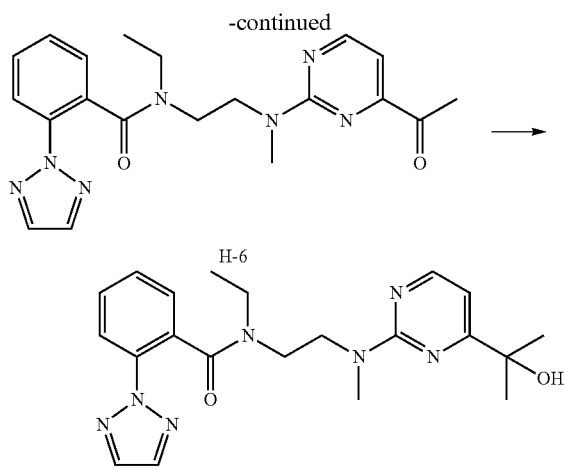

Example H-1

N-ethyl-N-(2-((4-(2-hydroxypropan-2-yl)pyrimidin-2-yl)(methylamino)ethyl)-2-(2H-1,2,3-triazol-2-yl)benzamide Step 1: tert-butyl (2-(2-(2H-1,2,3-triazol-2-yl)benzamido)ethyl)(methyl)carbamate (H-2)

To a mixture of 2-(2H-1,2,3-triazol-2-yl)benzoic acid (2.37 g, 12.5 mmol), HATU (6.0 g, 0.0158 mol) in THF (40 mL) was added DIEA (5.5 g, 0.042 mol). The mixture was stirred at RT for 10 min, then tert-butyl(2-aminoethyl)(methyl)carbamate (1.8 g, 10.5 mmol) was added. The resulting mixture was stirred at RT for 16 h, then poured into water and extracted with EtOAc (100 mL). The combined organic layers were washed with brine, dried over sodium sulfate, filtered and concentrated in vacuo. The residue was purified by column chromatography on silica gel (50% EtOAc in petroleum ether) to give the title compound H-2 (2.6 g). LRMS m/z (M+H) 346.3 found, 346.2 required.

Step 2: tert-butyl(2-(N-ethyl-2-(2H-1,2,3-triazol-2-yl)benzamido)ethyl)(methyl)carbamate (H-3)

To a solution of the H-2 (1.3 g, 3.77 mmol) in anhydrous DMF (12 mL) was added NaH (0.35 g, 8.7 mmol, 60%). The resulting mixture was stirred at 0° C. for 20 min, then iodoethane (1.12 g, 7.2 mmol) was added. The resulting mixture was stirred at RT overnight, quenched with water (20 mL) and extracted with EtOAc (50 mL×2). The combined organic layer was washed with brine (80 mL), dried over sodium sulfate, filtered and concentrated in vacuo. The residue was purified by silica gel gradient chromatography (50% EtOAc in petroleum ether) to give the title compound H-3 (1.3 g). LRMS m/z (M+H) 374.3 found, 374.2 required.

Step 3: N-ethyl-N-(2-(methylamino)ethyl)-2-(2H-1,2,3-triazol-2-yl)benzamide hydrochloride (H-4)

To a solution of the H-3 (0.3 g, 0.805 mmol) in EtOAc (2 mL) was added 4M HCl in dioxane (2 mL, 8.0 mmol). The mixture was stirred at 0° C. for 1 h and then concentrated in vacuo to afford the title compound H-4 as colorless oil (200 mg), which was used in the next step without further purification. LRMS m/z (M+H) 274.2 found, 274.2 required.

Step 4: N-(2-((4-cyanopyrimidin-2-yl)(methyl)amino)ethyl)-N-ethyl-2-(2H-1,2,3-triazol-2-yl)benzamide (H-5)

To a solution of the H-4 (250 mg, 0.807 mmol) in 1,4-dioxane (5 mL) were added 2-chloropyrimidine-4-carbonitrile (135 mg, 0.968 mmol) and Cs$_2$CO$_3$ (657 mg, 2.017 mmol). The resulting mixture was stirred at 90° C. for 12 h. LCMS indicated this experiment was completed. The mixture was diluted with water (100 mL) and extracted with EtOAc (100 mL×3). The combined organic layers were washed with brine, dried over sodium sulfate, filtered and the filtrate was concentrated in vacuo. The residue was purified by column chromatography on silica gel (50% EtOAc in petroleum ether) to give the title compound H-5 (250 mg). LRMS m/z (M+H) 377.1 found, 377.2 required.

Step 5: N-(2-((4-acetylpyrimidin-2-yl)(methyl)amino)ethyl)-N-ethyl-2-(2H-1,23-triazol-2-yl)benzamide (H-6)

To a solution of MeMgBr (1.1 ml, 3.3 mmol, 3M in ether) in dry THF (3 mL) was added a solution of the H-5 (250 mg, 0.664 mmol) in THF (2 mL) dropwise at 0° C. under nitrogen. The resulting mixture was stirred at 0° C. for 1.5 h. TLC (50% EtOAc in petroleum ether) indicated the reaction was completed. The mixture was quenched with saturated aqu. NH$_4$Cl solution and extracted with EtOAc (50 mL×3). The combined organic layers were washed with brine, dried over sodium sulfate, filtered and the filtrate was concentrated in vacuo. The residue was purified by silica gel chromatography (50% EtOAc in petroleum ether) to give the title compound H-6 (200 mg). LRMS m/z (M+H) 394.1 found, 394.2 required.

Step 6: N-ethyl-N-(2-((4-(2-hydroxypropan-2-yl)pyrimidin-2-yl)(methy)amino)ethyl)-2-(2H-1,2,3-triazol-2-yl)benzamide (Example H-1)

To a solution of MeMgBr (0.85 mL, 2.55 mmol, 3M in ether) in dry THF (3 mL) at 0° C. under nitrogen was added a solution of the H-6 (200 mg, 0.508 mmol) in THF (2 mL) dropwise. The resulting mixture was stirred at 0° C. for 1.5 h. TLC (50% EtOAc in petroleum ether) indicated the reaction was completed. The mixture was quenched with saturated aqu. NH4Cl solution and extracted with EtOAc (100 mL×3). The combined organic layer was washed with water (30 mL) and brine (50 mL), dried over anhydrous sodium sulfate, filtered and concentrated in vacuo. The residue was purified by HPLC to give the title compound H-1 (82 mg). LRMS m/z (M+H) 410.2 found, 410.2 required.

Example H-14

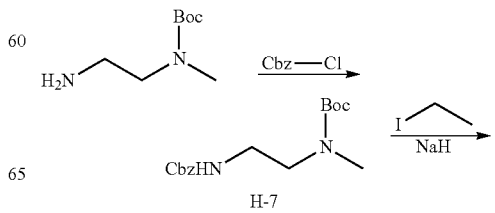

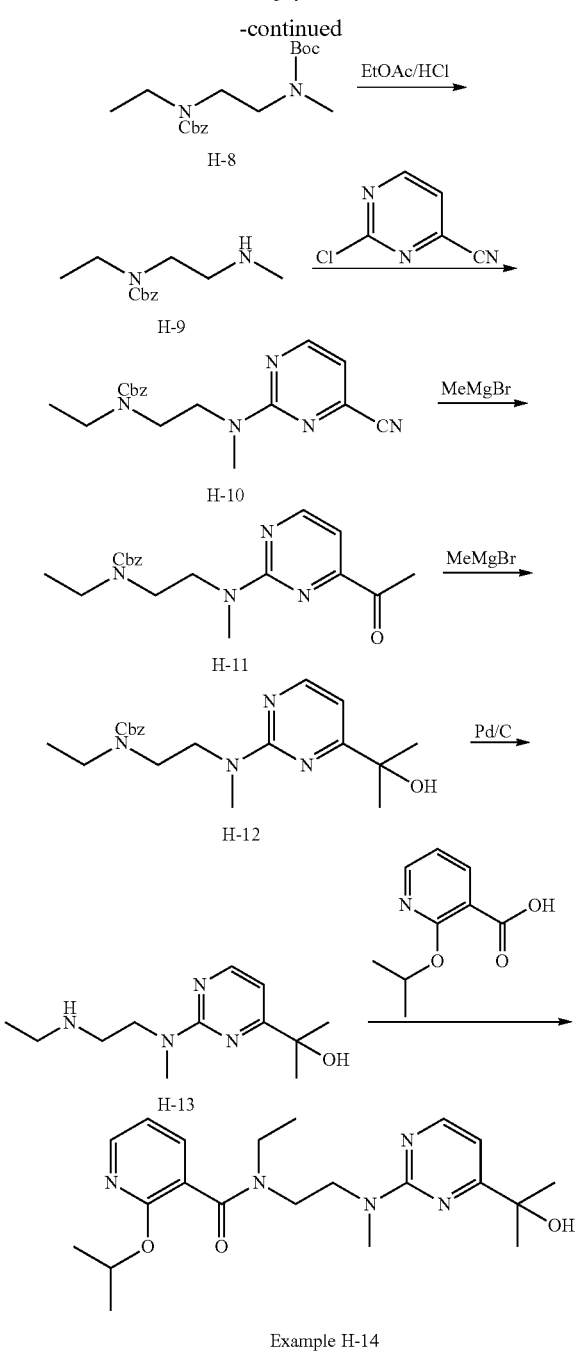

Example H-14

N-ethyl-N-(2-((4-(2-hydroxypropan-2-yl)pyrimidin-2-yl)(methyl)amino)ethyl)-2-isopropoxynicotinamide Step 1: tert-butyl (2-(((benzyloxy)carbonyl)amino)ethyl)(methyl)carbamate (H-7)

To a solution of tert-butyl (2-aminoethyl) (methyl)carbamate (5.0 g, 28.7 mmol) in THF (100 mL) was added NaHCO₃ (12.1 g, 143.5 mmol) at 0° C. The resulting mixture was stirred at the same temperature for 15 min. Cbz-Cl (5.9 g, 34.4 mmol) was added dropwise. The mixture was stirred at RT overnight, then filtered and the filtrate was concentrated in vacuo. The residue was purified by combiflash (10% EtOAc in petroleum ether) to give the title compound H-7. LRMS m/z (M+H) 309.1 found, 309.4 required.

Step 2: benzyl (2-((tert-butoxycarbonyl)(methyl)amino)ethyl)(ethyl)carbamate (H-8)

To a solution of the product H-7 (8.0 g, 25.94 mmol) in THF (150 mL) at 0° C. was added NaH (2.0 g, 51.9 mmol, 60% in mineral) in portions under N₂ atmosphere. After the mixture was stirred for 1 hour, EtI (8.1 g, 51.89 mmol) was added dropwise. The resulting mixture was stirred at RT overnight, then quenched with saturated aq. NH₄Cl (5 mL) and extracted with EtOAc (100 mL×3). The combined organic layers were dried over Na₂SO₄, filtered and concentrated in vacuo. The residue was purified by combiflash (10% EtOAc in petroleum) to give the title compound H-8. LRMS m/z (M+H) 337.1 found, 337.2 required.

Step 3: benzyl ethyl(2-(methylamino)ethyl)carbamate (H-9)

A solution of H-8 (6.8 g, 20.2 mmol) in HCl/EtOAc (150 mL) was stirred at RT for 1 h. The mixture was adjusted pH to 8~9 with NH₃.H₂O and then concentrated in vacuo. The residue was purified by combiflash (10% EtOAc in petroleum ether) to give the title compound H-9. LRMS m/z (M+H) 237.3 found, 237.1 required.

Step 4: benzyl (2-((4-cyanopyrimidin-2-yl)(methyl)amino)ethyl)(ethyl)carbamate (H-10)

To a mixture of the product H-9 (4.0 g, 16.93 mmol) in 1,4-dixoane (100 mL) were added 2-chloropyrimidine-4-carbonitrile (2.6 g, 18.62 mmol) and Cs₂CO₃ (22 g, 67.71 mmol). The resulting mixture was stirred at 80° C. overnight. After cooled to RT, the mixture was filtered and the filtrate was concentrated in vacuo. The residue was purified by combiflash (10% EtOAc in petroleum ether) to give the title compound H-10. LRMS m/z (M+H) 340.1 found, 340.2 required.

Step 5: benzyl (2-((4-acetylpyrimidin-2-yl)(methyl)amino)ethyl)(ethyl)carbamate (H-11)

To a solution of MeMgBr (20 mL, 60 mmol, 3 M in ether) at 0° C. was added a solution of the product from step 4 (5.5 g, 16.2 mmol) in THF (20 mL) dropwise. The resulting reaction was stirred at 0° C. for 1h, then quenched with saturated aq. NH₄Cl (2 mL), and then dried over Na₂SO₄, filtered and concentrated in vacuo. The residue was purified by combiflash (50% EtOAc in petroleum ether) to give the title compound H-11. LRMS m/z (M+H) 357.1 found, 357.2 required.

Step 6: benzylethyl(2-((4-(2-hydroxypropan-2-yl)pyrimidin-2-yl)-(methyl)amino)ethyl)-carbamate (H-12)

To a solution of CH₃MgBr (15 mL, 45 mmol, 3 M in ether) at 0° C. was added a solution of H-11 (4.2 g, 11.78 mmol) in THF (20 mL) dropwise. The resulting mixture was stirred at 0° C. for 1h, then quenched with saturated aq. NH₄Cl (2 mL), dried over Na₂SO₄, filtered and concentrated in vacuo. The residue was purified by combiflash (50%

EtOAc in petroleum ether) to give the title compound H-12. LRMS m/z (M+H) 373. found, 373.2 required.

Step 7: 2-(2-((2-(ethylamino)ethyl)(methyl)amino)pyrimidin-4-yl)propan-2-ol (H-13)

A solution of h-12 (1.8 g, 4.83 mmol) and Pd/C (500 mg) in THF (100 mL) was stirred at RT under 1 atm atmosphere of hydrogen overnight. The degassed mixture was then filtered over celite and the filtrate was concentrated in vacuo to give the title compound as colorless oil, which was used without further purification. LRMS m/z (M+H) 239.1 found, 239.2 required.

Step 8: N-ethyl-N-(2-((4-(2-hydroxypropan-2-yl)pyrimidin-2-yl)(methyl)amino)ethyl)-2-isopropoxynicotinamide (Example H-14)

To a solution of 2-isopropoxynicotinic acid (23 mg, 0.13 mmol) in DMF (2 mL) were added DIEA (20 mg, 0.13 mmol), HATU (43 mg, 0.13 mmol) and H-13 (30 mg, 0.13 mmol). The resulting mixture was stirred at room temperature overnight. The mixture was filtered and the filtrate was purified by Prep-HPLC to give the title compound H-14. LRMS m/z (M+H) 402.2 found, 402.2 required.

TABLE 5

The following compounds were prepared according to the general procedure provided in Example H-14 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| H-15 | 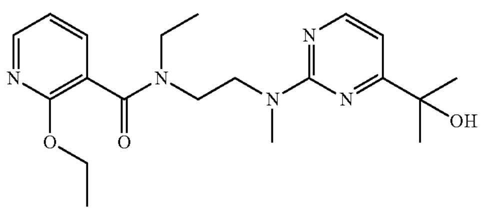 [SMILES: CCOc1ncccc1C(=O)N(CC)CCN(C)c1nccc(C(C)(C)O)n1] | 2-ethoxy-N-ethyl-N-(2-((4-(2-hydroxypropan-2-yl)pyrimidin-2-yl)(methyl)amino)ethyl)nicotinamide | Calc'd 388.2, found 388.2 |
| H-16 | 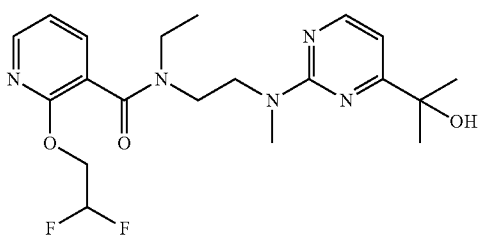 | 2-(2,2-difluoroethoxy)-N-ethyl-N-(2-((4-(2-hydroxypropan-2-yl)pyrimidin-2-yl)(methyl)amino)ethyl)nicotinamide | Calc'd 424.2, found 424.2 |
| H-17 | 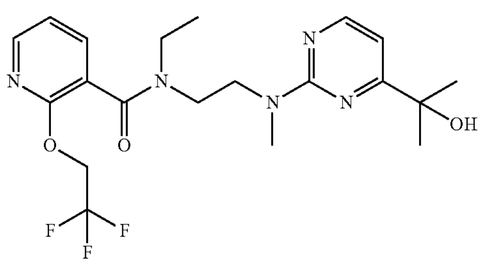 | 2-(2,2-difluoroethoxy)-N-ethyl-N-(2-((4-(2-hydroxypropan-2-yl)pyrimidin-2-yl)(methyl)amino)ethyl)nicotinamide | Calc'd 442.2, found 442.2 |
| H-18 | 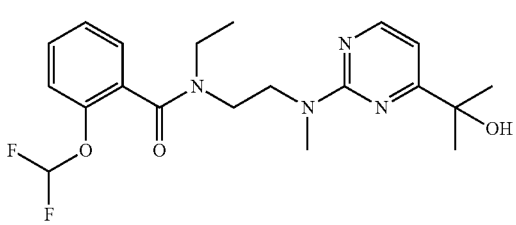 [SMILES: CCN(CCN(C)c1nccc(C(C)(C)O)n1)C(=O)c1ccccc1OC(F)F] | 2-(difluoromethoxy)-N-ethyl-N-(2-((4-(2-hydroxypropan-2-yl)pyrimidin-2-yl)(methyl)amino)ethyl)benzamide | Calc'd 409.2, found 409.1 |

TABLE 5-continued

The following compounds were prepared according to the general procedure provided in Example H-14 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| H-19 | 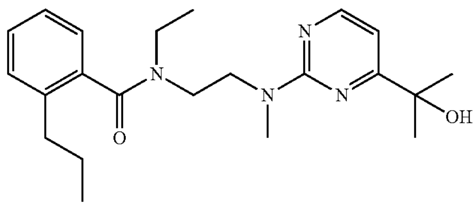 | N-ethyl-N-(2-((4-(2-hydroxypropan-2-yl)pyrimidin-2-yl)(methyl)amino)ethyl)-2-propylbenzamide | Calc'd 385.2 found 385.2 |
| H-20 | 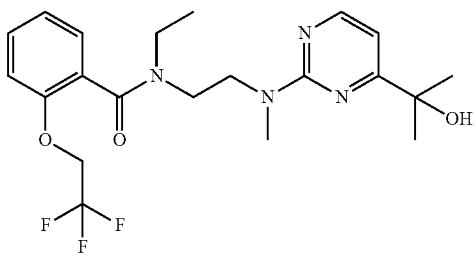 [SMILES: CCN(CCN(C)c1nccc(C(C)(C)O)n1)C(=O)c1ccccc1OCC(F)(F)F] | N-ethyl-N-(2-((4-(2-hydroxypropan-2-yl)pyrimidin-2-yl)(methyl)amino)ethyl)-2-(2,2,2-trifluoroethoxy)benzamide | Calc'd 441.2 found 441.1 |
| H-21 | 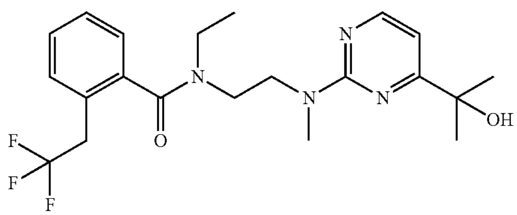 [SMILES: CCN(CCN(C)c1nccc(C(C)(C)O)n1)C(=O)c1ccccc1CC(F)(F)F] | N-ethyl-N-(2-((4-(2-hydroxypropan-2-yl)pyrimidin-2-yl)(methyl)amino)ethyl)-2-(2,2,2-trifluoroethyl)benzamide | Calc'd 425.2, found. 425.2 |
| H-22 | 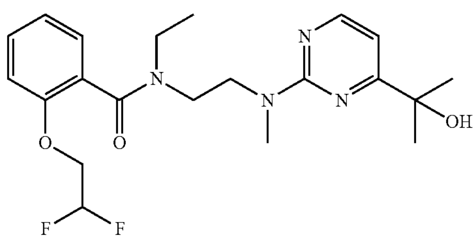 [SMILES: CCN(CCN(C)c1nccc(C(C)(C)O)n1)C(=O)c1ccccc1OCC(F)F] | 2-(2,2-difluoroethoxy)-N-ethyl-N-(2-((4-(2-hydroxypropan-2-yl)pyrimidin-2-yl)(methyl)amino)ethyl)benzamide | Calc'd 423.2, found 423.1 |
| H-23 | 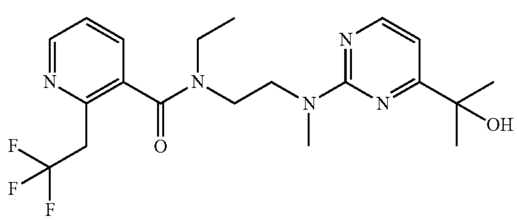 [SMILES: CCN(CCN(C)c1nccc(C(C)(C)O)n1)C(=O)c1cccnc1CC(F)(F)F] | N-ethyl-N-(2-((4-(2-hydroxypropan-2-yl)pyrimidin-2-yl)(methyl)amino)ethyl)-2-(2,2,2-trifluoroethyl)nicotinamide | Calc'd 426.2, found 426.2 |
| H-24 | 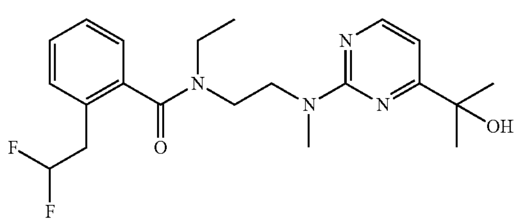 [SMILES: CCN(CCN(C)c1nccc(C(C)(C)O)n1)C(=O)c1ccccc1CC(F)F] | 2-(2,2-difluoroethyl)-N-ethyl-N-(2-((4-(2-hydroxypropan-2-yl)pyrimidin-2-yl)(methyl)amino)ethyl)benzamide | Calc'd 407.2 found 407.1 |

TABLE 5-continued

The following compounds were prepared according to the general procedure provided in Example H-14 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| H-25 | 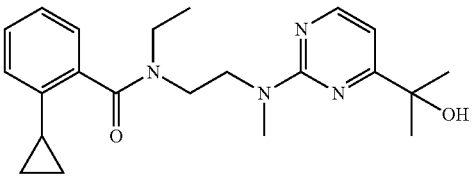 [SMILES: CCN(CCN(C)c1nccc(C(C)(C)O)n1)C(=O)c1ccccc1C1CC1] | 2-cyclopropyl-N-ethyl-N-(2-((4-(2-hydroxypropan-2-yl)pyrimidin-2-yl)(methyl)amino)ethyl)benzamide | Calc'd 383.2 found 383.2 |
| H-26 | 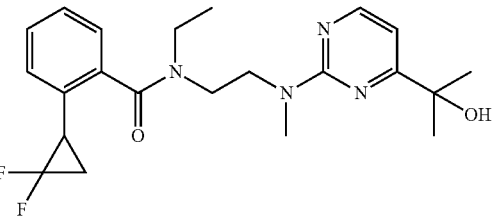 | 2-(2,2-difluorocyclopropyl)-N-ethyl-N-(2-((4-(2-hydroxypropan-2-yl)pyrimidin-2-yl)(methyl)amino)ethyl)benzamide | Calc'd 419.2, found 419.2 |
| H-27 | 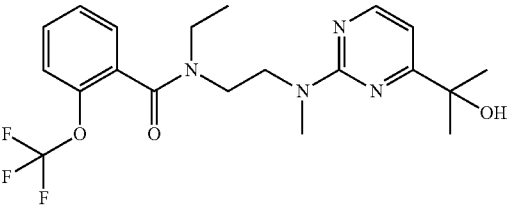 [SMILES: CCN(CCN(C)c1nccc(C(C)(C)O)n1)C(=O)c1ccccc1OC(F)(F)F] | N-ethyl-N-(2-((4-(2-hydroxypropan-2-yl)pyridin-2-yl)(methyl)amino)ethyl)-2-(trifluoromethoxy)benzamide | Calc'd 427.2, found 427.1 |
| H-28 | 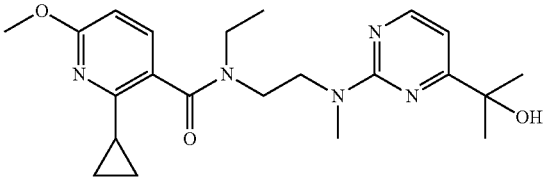 [SMILES: CCN(CCN(C)c1nccc(C(C)(C)O)n1)C(=O)c1ccc(OC)nc1C1CC1] | 2-cyclopropyl-N-ethyl-N-(2-((4-(2-hydroxypropan-2-yl)pyrimidin-2-yl)(methyl)amino)ethyl)-6-methoxynicotinamide | Calc'd 414.2, found 414.2 |
| H-29 | 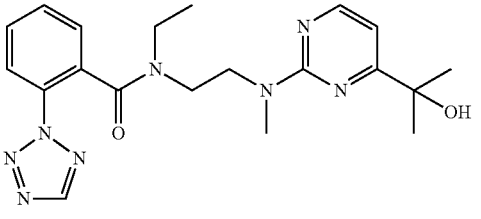 [SMILES: CCN(CCN(C)c1nccc(C(C)(C)O)n1)C(=O)c1ccccc1-n1ncnn1] | N-ethyl-N-(2-((4-(2-hydroxypropan-2-yl)pyrimidin-2-yl)(methyl)amino)ethyl)-2-(2H-tetrazol-2-yl)benzamide | Calc'd 411.2, found 411.2 |
| H-30 | 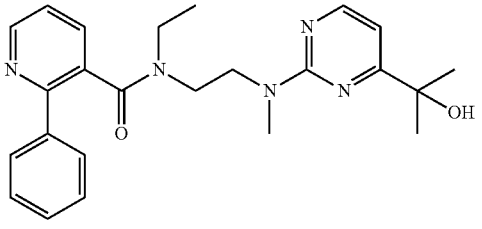 [SMILES: CCN(CCN(C)c1nccc(C(C)(C)O)n1)C(=O)c1cccnc1-c1ccccc1] | N-ethyl-N-(2-((4-(2-hydroxypropan-2-yl)pyrimidin-2-yl)(methyl)amino)ethyl)-2-phenylnicotinamide | Calc'd 420.2, found 420.2 |

TABLE 5-continued

The following compounds were prepared according to the general procedure provided in Example H-14 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| H-31 | 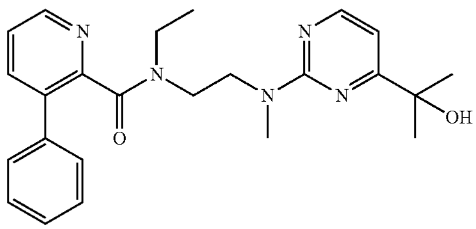 [SMILES: CCN(CCN(C)c1nccc(C(C)(C)O)n1)C(=O)c1ncccc1-c1ccccc1] | N-ethyl-N-(2-((4-(2-hydroxypropan-2-yl)pyrimidin-2-yl)(methyl)amino)ethyl)-3-phenylpicolinamide | Calc'd 420.2, found 420.2 |
| H-32 | 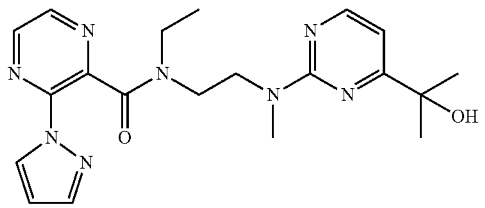 [SMILES: CCN(CCN(C)c1nccc(C(C)(C)O)n1)C(=O)c1nccnc1-n1cccn1] | N-ethyl-N-(2-((4-(2-hydroxypropan-2-yl)pyrimidin-2-yl)(methyl)amino)ethyl)-3-(1H-pyrazol-1-yl)pyrazine-2-carboxamide | Calc'd 411.2, found 411.2 |
| H-33 | 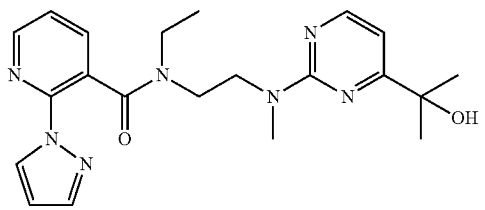 [SMILES: CCN(CCN(C)c1nccc(C(C)(C)O)n1)C(=O)c1cccnc1-n1cccn1] | N-ethyl-N-[2-[[4-(1-hydroxy-1-methyl-ethyl)pyrimidin-2-yl]-methyl-amino]ethyl]-2-pyrazol-1-yl-pyridine-3-carboxamide | Calc'd 410.2, found 410.2 |
| H-34 | 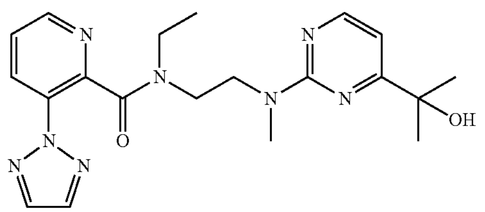 [SMILES: CCN(CCN(C)c1nccc(C(C)(C)O)n1)C(=O)c1ncccc1-n1nccn1] | N-ethyl-N-[2-[[4-(1-hydroxy-1-methyl-ethyl)pyrimidin-2-yl]-methyl-amino]ethyl]-3-(triazol-2-yl)pyridine-2-carboxamide | Calc'd 411.2, found 411.2 |

Example I

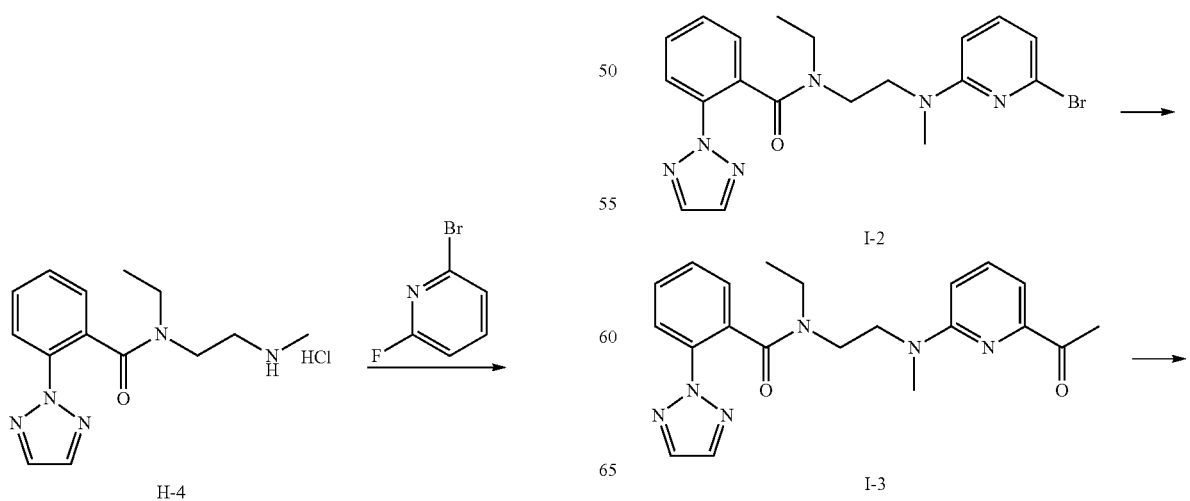

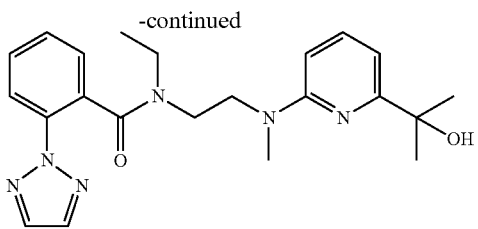

Example I-1

N-ethyl-N-(2-((6-(2-hydroxypropan-2-yl)pyridin-2-yl)(methyl)amino)ethyl)-2-(2H-1,2,3-triazol-2-yl)benzamide Step 1: N-(2-((6-bromopyridin-2-yl)(methyl)amino)ethyl)-N-ethyl-2-(2H-1,2,3-triazol-2-yl)benzamide (I-2)

To a solution of N-ethyl-N-(2-(methylamino)ethyl)-2-(2H-1,2,3-triazol-2-yl)benzamide hydrochloride H-4 (300 mg, 0.968 mmol) in dioxane (5 mL) were added 2-bromo-6-fluoropyridine (205 mg, 1.162 mmol) and Cs₂CO₃ (789 mg, 2.421 mmol). The resulting mixture was stirred at 100° C. overnight. LCMS indicated the reaction was completed. After cooled to RT, the mixture was filtered and concentrated in vacuo to give the title compound I-2 (200 mg). LRMS m/z (M+H) 429.1, 431.2 found, 429.1, 431.1 required.

Step 2: N-(2-((6-acetylpyridin-2-yl)(methyl)amino)ethyl)-N-ethyl-2-(2H-1,2,3-triazol-2-yl)benzamide (I-3)

To a solution of I-2 (200 mg, 0.466 mmol) in toluene (3 ml) was added TETRAKIS(TRIPHENYLPHOSPHINE)PALLADIUM(0) (30 mg, 0.026 mmol) and tributyl(1-ethoxyvinyl)stannane (1.57 g, 4.35 mmol). The mixture was stirred at 100° C. overnight and then cooled to RT. Then conc. HCl (1 mL) was added. After the mixture was stirred for additional 1h, LC-MS showed the reaction was completed. The mixture was diluted with water and extracted with EtOAc (100 mL×3). The combined organic layers were washed with brine, dried over Na₂SO₄ and filtered. The filtrate was concentrated in vacuo and the residue was purified by column chromatography (50% EtOAc in petroleum ether) to give the title compound I-3 (150 mg). LRMS m/z (M+H) 393.2 found, 393.2 required.

Step 3: N-ethyl-N-(2-((6-(2-hydroxypropan-2-yl)pyridin-2-yl)(methyl)amino)ethyl)-2-(2H-1,2,3-triazol-2-yl)benzamide (Example I-1)

To a solution of I-3 (150 mg, 0.382 mmol) in THF (2 ml) was added MeMgBr (0.64 ml, 1.911 mmol, 3M in ether) at 0° C. dropwise. The resulting mixture was stirred at RT for 1 hour. LCMS indicated the reaction was completed. The mixture was quenched with aq. NH4Cl, and extracted with EtOAc (50 mL×3). The combined organic layers were dried over Na₂SO₄, filtered and the filtrate was concentrated in vacuo. The residue was purified by Prep-HPLC to give the title compound I-1 (71 mg). LRMS m/z (M+H) 409.2 found, 409.2 required.

Example I-4

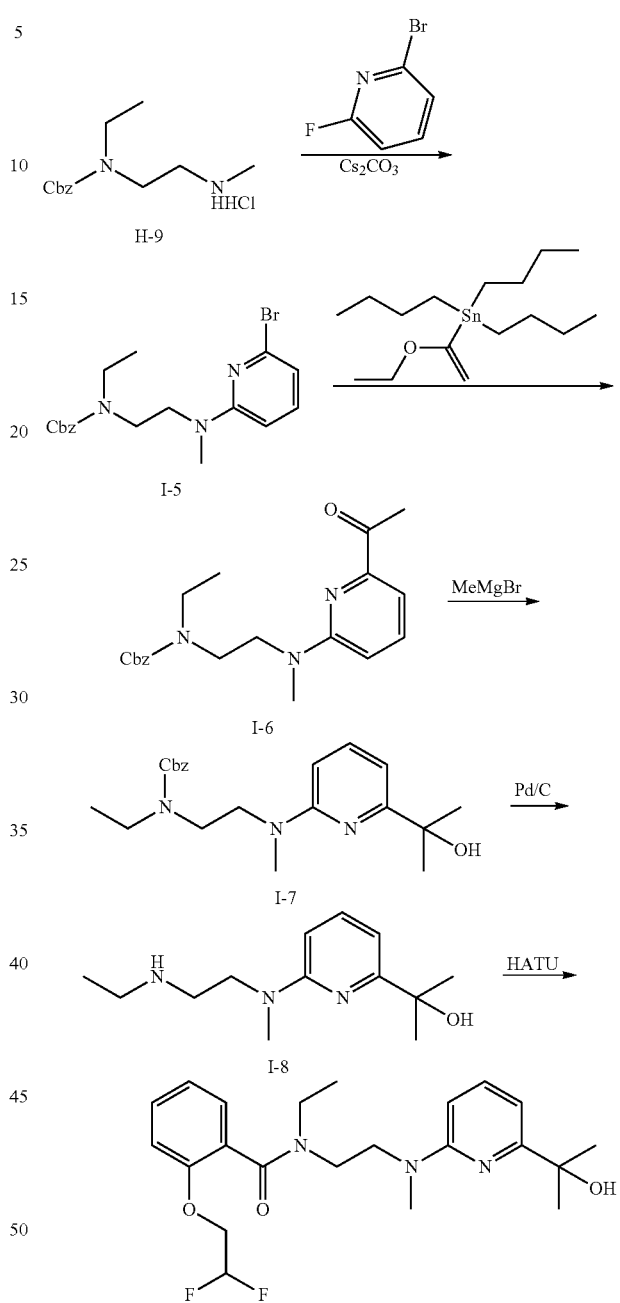

Example I-4

2-(2,2-difluoroethoxy)-N-ethyl-N-(2-((6-(2-hydroxypropan-2-yl)pyridin-2-yl)(methyl)amino)ethyl)benzamide Step 1: benzyl (2-((6-bromopyridin-2-yl)(methyl)amino)ethyl)(ethyl)carbamate (I-5)

To a solution of benzyl ethyl(2-(methylamino)ethyl)carbamate hydrochloride H-9 (1.3 g, 4.77 mmol) in dioxane (13 mL) was added 2-bromo-6-fluoropyridine (1.0 g, 5.72 mmol) and Cs₂CO₃ (6.21 g, 19.06 mmol). The mixture was allowed to be stirred at 100° C. for 16 h. After cooled to RT, the mixture was diluted with water (20 mL) and extracted with EtOAc (100 mL×3). The combined organic layers were dried over $MgSO_4$ and filtered. The filtrate was concentrated in vacuo. The residue was purified by column chromatography (15% EtOAc in petroleum ether) to give the title compound I-5. RMS m/z (M+H) 392.0, 394.0 found, 392.1 394.1 required.

Step 2: benzyl (2-((6-acetylpyridin-2-yl)(methyl) amino)ethyl)(ethyl)carbamate (I-6)

To a solution of I-5 (1.5 g, 3.82 mmol) in toluene (15 mL) was added ethyl tributylstannanecarboxylate (3.47 g, 9.56 mmol) and $Pd(PPh_3)_4$ (0.221 g, 0.191 mmol). The mixture was stirred at 100° C. under $N_2$ overnight. After the mixture was cooled to RT, conc. HCl (2 mL) was added. The resulting mixture was stirred at RT for 1 h, then diluted with water (30 mL) and extracted with EtOAc (100 mL×3). The combined organic layers were dried over $Na_2SO_4$, filtered and concentrated in vacuo. The residue was purified by column chromatography (50% EtOAc in petroleum ether) to give product I-6. LRMS m/z (M+H) 356.2 found, 356.2 required.

Step 3: benzyl ethyl(2-((6-(2-hydroxypropan-2-yl) pyridin-2-yl)(methyl)amino)ethyl)carbamate (I-7)

To a solution of I-6 (1.0 g, 2.81 mmol) in dry THF (15 mL) at 0° C. was added a solution of $CH_3MgBr$ (4.69 mL, 14.07 mmol, 3M in ether) dropwise. The resulting mixture was stirred at 0° C. for 2.5 h, then quenched with water (20 mL) and extracted with EtOAc (100 mL×3). The combined organic layers were dried over $MgSO_4$ and filtered. The filtrate was concentrated in vacuo. The residue was purified by column chromatography (50% EtOAc in petroleum ether) to give the title compound I-7. LRMS m/z (M+H) 372.2 found, 372.2 required.

Step 4: 2-(6-((2-(ethylamino)ethyl)(methyl)amino) pyridin-2-yl)propan-2-ol (I-8)

To a solution of I-7 (900 mg, 2.42 mmol) in MeOH (15 mL) was added Pd/C (258 mg, 10 w %). The mixture was stirred under $H_2$ balloon at room temperature for 2h, then filtered and the filtrate was concentrated in vacuo to provide the title compound I-8. LRMS m/z (M+H) 238.1 found, 238.2 required.

Step 5: 2-(2,2-difluoroethoxy)-N-ethyl-N-(2-((6-(2-hydroxypropan-2-yl)pyridin-2-yl)(methyl)amino) ethyl)benzamide (Example I-4)

To a solution of 2-(2,2-difluoroethoxy)benzoic acid I-8 (25.6 mg, 0.126 mmol) in DMF (3 mL) was added DIEA (0.088 mL, 0.506 mmol) and HATU (57.7 mg, 0.152 mmol) and the product from step 4 (30 mg, 0.126 mmol). The resulting mixture was stirred at room temperature overnight. LCMS indicated the reaction was completed. The mixture was filtered and the filtrate was purified by prep-HPLC to give the title compound I-4. LRMS m/z (M+H) 422.2 found, 422.2 required.

TABLE 6

The following compounds were prepared according to the general procedure provided in Example 1-4 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| I-9 | 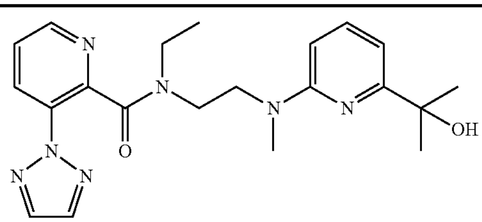 | N-ethyl-N-(2-((6-(2-hydroxypropan-2-yl)pyridin-2-yl)(methyl)amino)ethyl)-3-(2H-1,2,3-triazol-2-yl)picolinamide | Calc'd 410.2, found 410.2 |
| I-10 | 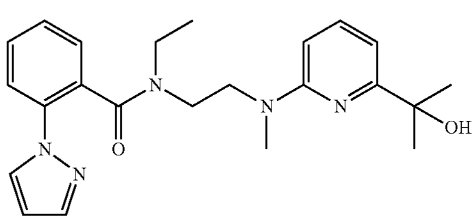 [SMILES: CCN(CCN(C)c1cccc(C(C)(C)O)n1)C(=O)c1ccccc1-n1cccn1] | N-ethyl-N-(2-((6-(2-hydroxypropan-2-yl)pyridin-2-yl)(methyl)amino)ethyl)-2-(1H-pyrazol-1-yl)benzamide | Calc'd 408.2, found 408.2 |
| I-11 | 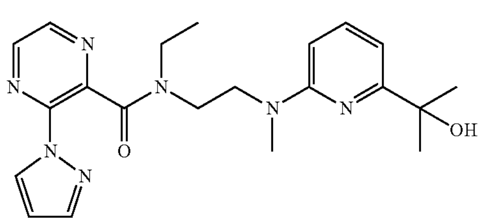 [SMILES: CCN(CCN(C)c1cccc(C(C)(C)O)n1)C(=O)c1nccnc1-n1cccn1] | N-ethyl-N-(2-((6-(2-hydroxypropan-2-yl)pyridin-2-yl)(methyl)amino)ethyl)-3-(1H-pyrazol-1-yl)pyrazine-2-carboxamide | Calc'd 410.2, found 410.2 |

TABLE 6-continued

The following compounds were prepared according to the general procedure provided in Example 1-4 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| I-12 | 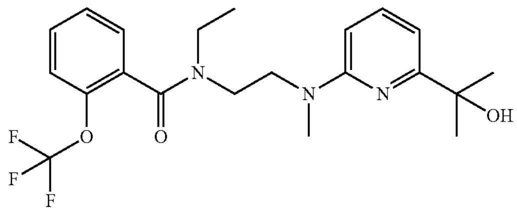 | N-ethyl-N-(2-((6-(2-hydroxypropan-2-yl)pyridin-2-yl)(methyl)amino)ethyl)-2-(trifluoromethoxy)benzamide | Calc'd 426.2, found 426.2 |
| I-13 | 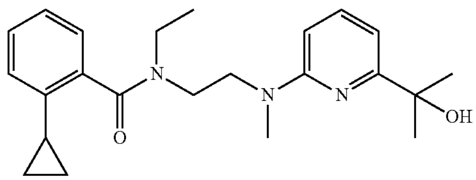 [SMILES: CCN(CCN(C)c1cccc(C(C)(C)O)n1)C(=O)c1ccccc1C1CC1] | 2-cyclopropyl-N-ethyl-N-(2-((6-(2-hydroxypropan-2-yl)pyridin-2-yl)(methyl)amino)ethyl)benzamide | Calc'd 382.2, found 382.2c |
| I-14 | 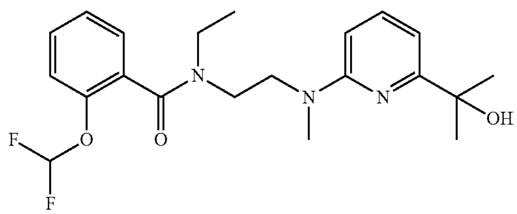 [SMILES: CCN(CCN(C)c1cccc(C(C)(C)O)n1)C(=O)c1ccccc1OC(F)F] | 2-(difluoromethoxy)-N-ethyl-N-(2-((6-(2-hydroxypropan-2-yl)pyridin-2-yl)(methyl)amino)ethyl)benzamide | Calc'd 408.2, found 408.2 |
| I-15 | 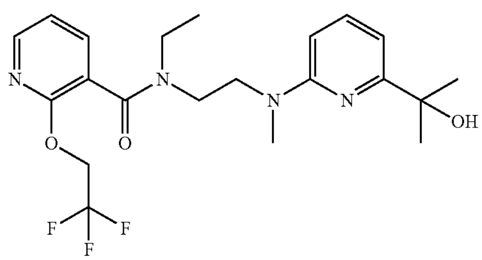 [SMILES: CCN(CCN(C)c1cccc(C(C)(C)O)n1)C(=O)c1cccnc1OCC(F)(F)F] | N-ethyl-N-(2-((6-(2-hydroxypropan-2-yl)pyridin-2-yl)(methyl)amino)ethyl)-2-(2,2,2-trifluoroethoxy)nicotinamide | Calc'd 441.2, found 441.2 |
| I-16 | 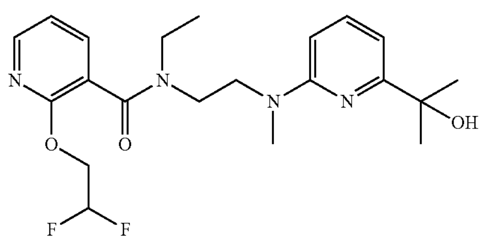 [SMILES: CCN(CCN(C)c1cccc(C(C)(C)O)n1)C(=O)c1cccnc1OCC(F)F] | 2-(2,2-difluoroethoxy)-N-ethyl-N-(2-((6-(2-hydroxypropan-2-yl)pyridin-2-yl)(methyl)amino)ethyl)nicotinamide | Calc'd 423.2, found 423.2 |
| I-17 | 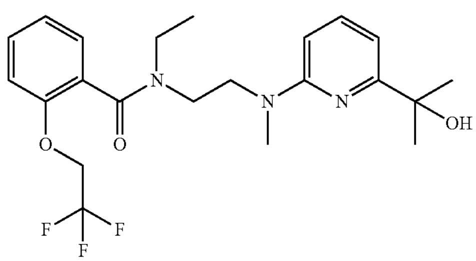 [SMILES: CCN(CCN(C)c1cccc(C(C)(C)O)n1)C(=O)c1ccccc1OCC(F)(F)F] | N-ethyl-N-(2-((6-(2-hydroxypropan-2-yl)pyridin-2-yl)(methyl)amino)ethyl)-2-(2,2,2-trifluoroethoxy)benzamide | Calc'd 440.2, found 440.2 |

TABLE 6-continued

The following compounds were prepared according to the general procedure provided in Example 1-4 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| I-18 | 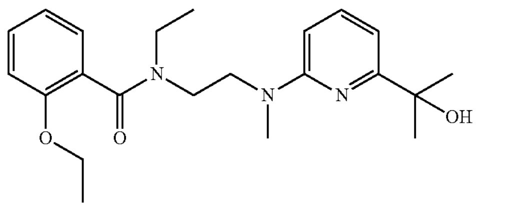 [SMILES: CCOc1ccccc1C(=O)N(CC)CCN(C)c1cccc(C(C)(C)O)n1] | 2-ethoxy-N-ethyl-N-(2-((6-(2-hydroxypropan-2-yl)pyridin-2-yl)(methyl)amino)ethyl)benzamide | Calc'd 386.2, found 386.2 |
| I-19 | 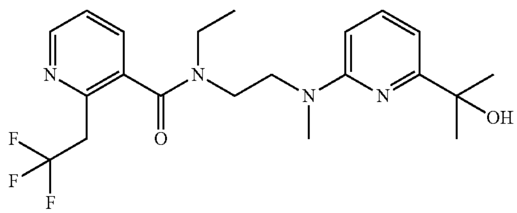 [SMILES: CCN(CCN(C)c1cccc(C(C)(C)O)n1)C(=O)c1cccnc1CC(F)(F)F] | N-ethyl-N-(2-((6-(2-hydroxypropan-2-yl)pyridin-2-yl)(methyl)amino)ethyl)-2-(2,2,2-trifluoroethyl)nicotinamide | Calc'd 425.2, found 425.2 |
| I-20 | 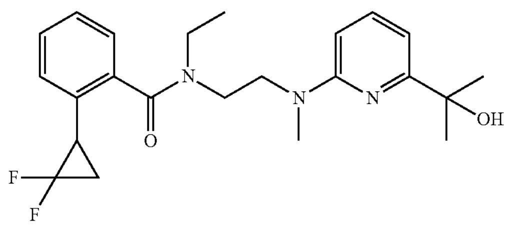 [SMILES: CCN(CCN(C)c1cccc(C(C)(C)O)n1)C(=O)c1ccccc1C1CC1(F)F] | 2-(2,2-difluorocyclopropyl)-N-ethyl-N-(2-((6-(2-hydroxypropan-2-yl)pyridin-2-yl)(methyl)amino)ethyl)benzamide | Calc'd 418.2, found 418.2 |
| I-21 | 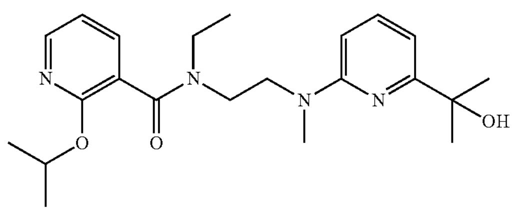 [SMILES: CCN(CCN(C)c1cccc(C(C)(C)O)n1)C(=O)c1cccnc1OC(C)C] | N-ethyl-N-(2-((6-(2-hydroxypropan-2-yl)pyridin-2-yl)(methyl)amino)ethyl)-2-isopropoxynicotinamide | Calc'd 401.2, found 401.2 |
| I-22 | 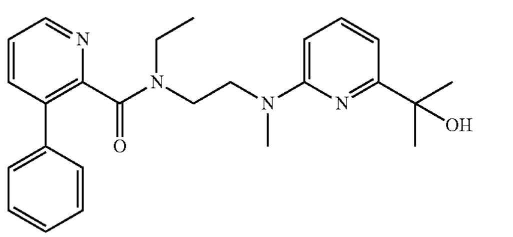 [SMILES: CCN(CCN(C)c1cccc(C(C)(C)O)n1)C(=O)c1ncccc1-c1ccccc1] | N-ethyl-N-(2-((6-(2-hydroxypropan-2-yl)pyridin-2-yl)(methyl)amino)ethyl)-3-phenylpicolinamide | Calc'd 419.2, found 419.2 |
| I-23 | 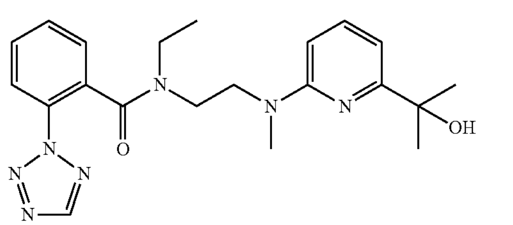 [SMILES: CCN(CCN(C)c1cccc(C(C)(C)O)n1)C(=O)c1ccccc1-n1ncnn1] | N-ethyl-N-(2-((6-(2-hydroxypropan-2-yl)pyridin-2-yl)(methyl)amino)ethyl)-2-(2H-tetrazol-2-yl)benzamide | Calc'd 410.2, found 410.2 |

TABLE 6-continued

The following compounds were prepared according to the general procedure provided in Example 1-4 and procedures herein, but substituting the appropriate aryl amide, as described in the foregoing Reaction Schemes and Examples. The requisite starting materials are either prepared as described in the intermediates section, commercially available, or may be prepared from commercially available reagents using conventional reactions well known in the art without undue experimentation.

| Ex. | Structure | Name | Mass [M + H] |
|---|---|---|---|
| I-24 | 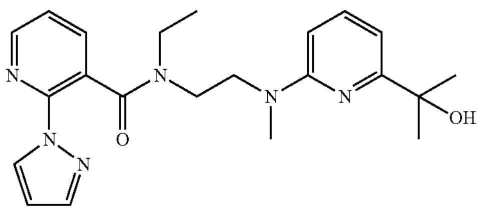 [SMILES: CCN(CCN(C)c1cccc(C(C)(C)O)n1)C(=O)c1cccnc1-n1cccn1] | N-ethyl-N-(2-((6-(2-hydroxypropan-2-yl)pyridin-2-yl)(methyl)amino)ethyl)-2-(1H-pyrazol-1-yl)nicotinamide | Calc'd 409.2, found 409.2 |
| I-25 | 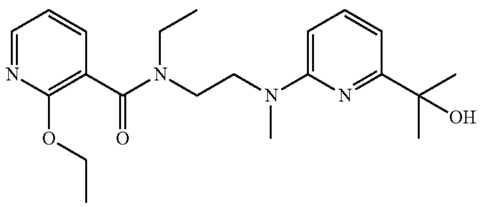 | 2-ethoxy-N-ethyl-N-(2-((6-(2-hydroxypropan-2-yl)pyridin-2-yl)(methyl)amino)ethyl)nicotinamide | Calc'd 387.2, found 387.2 |

TABLE 7

The following table shows representative data for the compounds of the Examples as orexin receptor antagonists as determined by the assays described herein.

| Example | hOX2R FLIPR IC$_{50}$ (nM) | hOX1R FLIPR IC$_{50}$ (nM) |
|---|---|---|
| A-1 | 36.5 | 2453 |
| A-5 | 1760 | 10000 |
| B-1 | 26.4 | 2727 |
| B-5 | 80.0 | 10000 |
| B-6 | 68.1 | 10000 |
| B-7 | 9.4 | 1109 |
| B-8 | 18.5 | 2175 |
| B-9 | 26.4 | 10000 |
| B-10 | 40.6 | 10000 |
| B-11 | 19.8 | 6093 |
| B-12 | 12.6 | 2827 |
| B-13 | 16 | 2006 |
| B-14 | 13.9 | 2600 |
| B-15 | 1271 | 10000 |
| B-16 | 19.9 | 1650 |
| B-17 | 11.2 | 2031 |
| B-18 | 36.2 | 3637 |
| B-19 | 32.1 | 9682 |
| B-20 | 9.2 | 1559 |
| B-21 | 424.1 | 10000 |
| B-22 | 32.4 | 10000 |
| B-23 | 94.9 | 10000 |
| B-24 | 12.8 | 5081 |
| B-25 | 324.3 | 10000 |
| B-26 | 20.4 | 1183 |
| B-27 | 12.5 | 758.9 |
| B-28 | 18.7 | 10000 |
| B-29 | 18.9 | 3013 |
| B-30 | 18.5 | 789.9 |
| B-31 | 8.8 | 2564 |
| B-32 | 19.5 | 984.8 |
| B-33 | 23 | 7200 |
| C-1 | 36.6 | 3173 |
| C-3 | 1457 | 10000 |
| D-1 | 56.1 | 3295 |
| E-1 | 14.5 | 7631 |
| E-7 | 198.1 | 10000 |
| E-8 | 109.9 | 10000 |
| E-9 | 341.1 | 8214 |
| E-10 | 244.4 | 10000 |
| E-11 | 18.4 | 1145 |
| E-14 | 568.7 | 10000 |
| E-16 | 84.7 | 236.2 |
| E-22 | 569 | 10000 |
| F-1 | 58.2 | 10000 |
| F-5 | 10000 | 10000 |
| F-6 | 97.9 | 9555 |
| F-7 | 10000 | 10000 |
| F-8 | 1992 | 10000 |
| F-9 | 10000 | 10000 |
| F-10 | 7195 | 10000 |
| F-11 | 22.96 | 10000 |
| F-12 | 49.6 | 10000 |
| F-13 | 48.4 | 10000 |
| F-14 | 77.4 | 10000 |
| F-15 | 33.9 | 10000 |
| F-16 | 688 | 10000 |
| F-17 | 945.3 | 10000 |
| F-18 | 10000 | 10000 |
| F-19 | 10000 | 10000 |
| F-20 | 16.2 | 1621 |
| F-21 | 341.1 | 10000 |
| F-22 | 31.8 | 10000 |
| F-23 | 10000 | 10000 |
| F-24 | 1633 | 10000 |
| F-25 | 4390 | 10000 |
| F-26 | 18.9 | 7711 |
| F-27 | 24.0 | 8355 |
| F-28 | 461.4 | 10000 |
| F-29 | 10000 | 10000 |
| F-30 | 24.4 | 9438 |
| F-31 | 10000 | 10000 |
| G-1 | 88 | 10000 |
| G-4 | 12.1 | 1469 |

TABLE 7-continued

The following table shows representative data for the compounds of the Examples as orexin receptor antagonists as determined by the assays described herein.

| Example | hOX2R FLIPR IC$_{50}$ (nM) | hOX1R FLIPR IC$_{50}$ (nM) |
|---|---|---|
| G-5 | 19.8 | 3214 |
| G-6 | 112.1 | 3855 |
| G-7 | 35.8 | 8426 |
| G-8 | 12.2 | 1178 |
| G-9 | 76.5 | 9196 |
| G-10 | 113.2 | 10000 |
| H-1 | 11 | 4070 |
| H-14 | 65.4 | 10000 |
| H-15 | 77.3 | 10000 |
| H-16 | 24.19 | 10000 |
| H-17 | 21.7 | 10000 |
| H-18 | 49.3 | 10000 |
| H-19 | 13.1 | 10000 |
| H-20 | 32.0 | 10000 |
| H-21 | 17.97 | 10000 |
| H-22 | 17.7 | 10000 |
| H-23 | 178.6 | 10000 |
| H-24 | 20.6 | 10000 |
| H-25 | 9.1 | 10000 |
| H-26 | 16.9 | 10000 |
| H-27 | 10 | 10000 |
| H-28 | 20 | 10000 |
| H-29 | 17 | 10000 |
| H-30 | 53 | 10000 |
| H-31 | 23 | 10000 |
| H-32 | 54 | 10000 |
| H-33 | 37 | 10000 |
| H-34 | 43 | 10000 |
| I-1 | 12.4 | 10000 |
| I-4 | 179.1 | 10000 |
| I-9 | 311.8 | 10000 |
| I-10 | 93.3 | 10000 |
| I-11 | 327.8 | 10000 |
| I-12 | 73.7 | 10000 |
| I-13 | 53.67 | 10000 |
| I-14 | 201 | 10000 |
| I-15 | 306.1 | 10000 |
| I-16 | 234.5 | 10000 |
| I-17 | 326 | 10000 |
| I-18 | 154 | 10000 |
| I-19 | 2266 | 10000 |
| I-20 | 36.37 | 10000 |
| I-21 | 386.8 | 10000 |
| I-22 | 211.1 | 10000 |
| I-23 | 69.59 | 10000 |
| I-24 | 103.7 | 10000 |
| I-25 | 465.9 | 10000 |

As indicated by the data herein, the compounds of the present examples provide greater functional selectivity for the orexin-2 receptor over the orexin-1 receptor. The distinction in potency between the orexin-2 receptor and the orexin-1 receptor in the whole cell FLIPR functional assay provides enhanced predictive value for determining in vivo efficacy. Increasing the functional selectivity for the orexin-2 receptor reduces the potential for dual receptor antagonism in vivo. Such greater functional selectivity may provide benefits over other orexin receptor antagonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

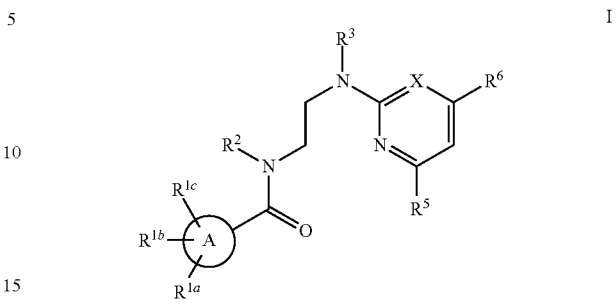

wherein:
A is selected from the group consisting of phenyl, pyridyl, pyrazinyl, benzimidazolyl, and benzoxazolyl;
X is N or CH;
each of $R^{1a}$, $R^{1b}$ and $R^{1c}$ is independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) —CN, and
(7) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or—$NO_2$;
$R^2$ is $C_{1-6}$alkyl, which is which is unsubstituted or substituted with halo, $C_{3-6}$cycloalkyl or phenyl;
$R^3$ is $C_{1-6}$alkyl, which is which is unsubstituted or substituted with halo or hydroxyl;
$R^5$ is selected from the group consisting of:
(1) hydrogen,
(2) halogen,
(3) —CN,
(4) $C_{1-6}$alkyl, which is unsubstituted or substituted with halogen, hydroxyl or phenyl,
(5) —O—$C_{1-6}$alkyl, which is unsubstituted or substituted with halogen or phenyl,
(6) —O—$C_{3-6}$cycloalkyl, which is unsubstituted or substituted with $C_{1-6}$alkyl, halogen or phenyl, and
(7) —(C=O)—O—$C_{1-6}$alkyl;
$R^6$ is selected from the group consisting of:
(1) hydrogen,
(2) halogen,
(3) —CN,
(4) $C_{1-6}$alkyl, which is unsubstituted or substituted with halogen, hydroxyl or phenyl,
(5) —O—$C_{1-6}$alkyl, which is unsubstituted or substituted with halogen or phenyl,
(6) —O—$C_{3-6}$cycloalkyl, which is unsubstituted or substituted with $C_{1-6}$alkyl, halogen or phenyl, and
(7) —(C=O)—O—$C_{1-6}$alkyl
with the proviso that at least one of $R^5$ and $R^6$ is other than hydrogen;
or a pharmaceutically acceptable salt thereof.

2. The compound of claim 1 of the formula Ia:

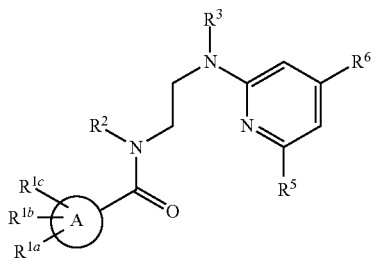

or a pharmaceutically acceptable salt thereof.

3. The compound of claim 1 of the formula Ib:

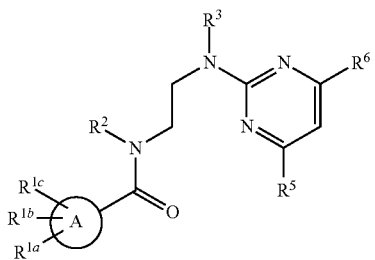

or a pharmaceutically acceptable salt thereof.

4. The compound of claim 1 or a pharmaceutically acceptable salt thereof wherein $R^2$ is ethyl.

5. The compound of claim 1 or a pharmaceutically acceptable salt thereof wherein $R^3$ is methyl.

6. The compound of claim 1 or a pharmaceutically acceptable salt thereof wherein $R^5$ is selected from the group consisting of:
(1) hydrogen,
(2) methyl,
(3) —C(CH$_3$)$_2$OH,
(4) —CH(OH)CF$_3$,
(5) —CH(OH)CH$_3$,
(6) —C(OH)(CF$_3$)CH$_3$, and
(7) —C(=O)OCH$_3$.

7. The compound of claim 1 or a pharmaceutically acceptable salt thereof wherein $R^6$ is selected from the group consisting of: hydrogen, —CN, and methyl.

8. A compound which is selected from the group consisting of:
N-(2-((4,6-dimethylpyrimidin-2-yl)(methyl)amino) ethyl)-N-ethyl-2-(2H-1,2,3-triazol-2-yl)benzamide;
2-cyclopropyl-N-(2-((4,6-dimethylpyrimidin-2-yl) (methyl)amino)ethyl)-N-ethylbenzamide;
N-(2-((4,6-dimethylpyrimidin-2-yl)(methyl)amino) ethyl)-N-ethyl-2-isopropoxynicotinamide;
N-(2-((4,6-dimethylpyrimidin-2-yl)(methyl)amino) ethyl)-2-ethoxy-N-ethylnicotinamide;
N-(2-((4,6-dimethylpyrimidin-2-yl)(methyl)amino) ethyl)-N-ethyl-2-(trifluoromethoxy)benzamide;
2-(difluoromethoxy)-N-(2-((4,6-dimethylpyrimidin-2-yl) (methyl)amino)ethyl)-N-ethylbenzamide;
N-(2-((4,6-dimethylpyrimidin-2-yl)(methyl)amino) ethyl)-N-ethyl-2-phenylnicotinamide;
2-(2,2-difluoroethoxy)-N-(2-(4,6-dimethylpyrimidin-2-yl)(methyl)amino)ethyl)-N-ethylnicotinamide;
N-(2-((4,6-dimethylpyrimidin-2-yl)(methyl)amino) ethyl)-N-ethyl-2-(2,2,2-trifluoroethoxy)nicotinamide;
N-(2-((4,6-dimethylpyrimidin-2-yl)(methyl)amino) ethyl)-N-ethyl-4-fluoro-2-(2H-1,2,3-triazol-2-yl)benzamide
N-(2-((4,6-dimethylpyrimidin-2-yl)(methyl)amino) ethyl)-2-ethoxy-N-ethylbenzamide;
N-(2-((4,6-dimethylpyrimidin-2-yl)(methyl)amino) ethyl)-N-ethyl-2-(1H-pyrazol-1-yl)benzamide;
N-(2-((4,6-dimethylpyrimidin-2-yl)(methyl)amino) ethyl)-N-ethyl-3-(2H-1,2,3-triazol-2-yl)pyrazine-2-carboxamide;
N-{2-[(4,6-dimethylpyrimidin-2-yl)(methyl)amino] ethyl}-N-ethyl-2-propylbenzamide;
N-{2-[(4,6-dimethylpyrimidin-2-yl)(methyl)amino] ethyl}-N-ethyl-2-(2,2,2-trifluoroethoxy)-benzamide;
N-{2-[(4,6-dimethylpyrimidin-2-yl)(methyl)amino] ethyl}-N-ethyl-2-(2,2,2-trifluoroethyl)benzamide;
2-cyclopropyl-N-{2-[(4,6-dimethylpyrimidin-2-yl) (methyl)amino]ethyl}-N-ethyl-6-methoxypyridine-3-carboxamide;
2-(2,2-difluoroethoxy)-N-{2-[(4,6-dimethylpyrimidin-2-yl)(methyl)amino]ethyl}-N-ethylbenzamide;
N-{2-[(4,6-dimethylpyrimidin-2-yl)(methyl)amino] ethyl}-N-ethyl-2-(2,2,2-trifluoroethyl)pyridine-3-carboxamide;
N-{2-[(4,6-dimethylpyrimidin-2-yl)(methyl)amino] ethyl}-N-ethyl-3 -(2H-1,2,3-triazol-2-yl)pyridine-2-carboxamide;
2-(2,2-difluoroethyl)-N-{2-[(4,6-dimethylpyrimidin-2-yl)(methyl)amino]ethyl}-N-ethylbenzamide;
N-{2-[(4,6-dimethylpyrimidin-2-yl)(methyl)amino] ethyl}-N-ethyl-2-(1H-pyrazol-1-yl)pyridine-3-carboxamide;
N-{2-[(4,6-dimethylpyrimidin-2-yl)(methyl)amino] ethyl}-N-ethyl-3-pyrrolidin-1-ylpyrazine-2-carboxamide;
2-cyclobutyl-N-{2[(4,6-dimethylpyrimidin-2-yl)(methyl) amino]ethyl}-N-ethylbenzamide;
N-{2-[(4,6-dimethylpyrimidin-2-yl)(methyl)amino] ethyl}-N-ethyl-3-phenylpyridine-2-carboxamide;
N-{2-[(4,6-dimethylpyrimidin-2-yl)(methyl)amino] ethyl}-N-ethyl-3-(1H-pyrazol-1-yl)pyrazine-2-carboxamide;
2-(2,2-difluorocyclopropyl)-N-{2-[(4,6-dimethylpyrimidin-2-yl)(methyl)amino]ethyl}-N-ethylbenzamide;
N-{2-[(4,6-dimethylpyrimidin-2-yl)(methyl)amino] ethyl}-N-ethyl-2-pyrrolidin-1-ylbenzamide;
N-{2-[(4,6-dimethylpyrimidin-2-yl)(methyl)amino] ethyl}-N-ethyl-2-(2H-tetrazol-2-yl)benzamide;
N-{2-[(4,6-dimethylpyrimidin-2-yl)(methyl)amino] ethyl}-N-ethyl-2-pyrimidin-2-ylbenzamide;
N-{2-[(4,6-dimethylpyrimidin-2-yl)(methyl)amino] ethyl}-N-ethyl-3-pyridin-2-ylpyrazine-2-carboxamide;
N-(2-((4,6-dimethylpyrimidin-2-yl)(ethyl)amino)ethyl)-N-ethyl-2-(2H-1,2,3-triazol-2-yl)benzamide;
N-(2-((4,6-dimethylpyrimidin-2-yl)(isopropyl)amino) ethyl)-N-ethyl-2-(2H-1,2,3-triazol-2-yl)benzamide;
N-(2-((2,2-difluoroethyl)(4,6-dimethylpyrimidin-2-yl) amino)ethyl)-N-ethyl-2-(2H-1,2,3-triazol-2-yl)benzamide;
N-(2-((4-cyanopyridin-2-yl)(methyl)amino)ethyl)-N-ethyl-2-(2H-1,2,3-triazol-2-yl)benzamide;
N-(2-((4-cyano-3-methylpyridin-2-yl)(methyl)amino) ethyl)-N-ethyl-2-(2H-1,2,3-triazol-2-yl)benzamide;
N-{2-[(3-chloro-4-cyanopyridin-2-yl)(methyl)amino] ethyl}-N-ethyl-2-(2H-1,2,3-triazol-2-yl)benzamide;

N-{2-[(4,6-dimethoxypyrimidin-2-yl)(methyl)amino]
ethyl}-N-ethyl-2-(2H-1,2,3-triazol-2-yl)benzamide;
N-{2-[(4-cyanopyrimidin-2-yl)(methyl)amino]ethyl}-N-
ethyl-2-(2H-1,2,3-triazol-2-yl)benzamide;
N-(2-{[4-chloro-6-(dimethylamino)pyrimidin-2-yl]
(methyl)amino}ethyl)-N-ethyl-2-(2H-1,2,3-triazol-2-
yl)benzamide;
N-{2-[(6-cyanopyridin-2-yl)(methyl)amino]ethyl}-N-
ethyl-2-(2H-1,2,3-triazol-2-yl)benzamide;
N-(2-{[5-chloro-4-(trifluoromethyl)pyrimidin-2-yl]
(methyl)amino}ethyl)-N-ethyl-2-(2H-1,2,3-triazol-2-
yl)benzamide;
N-{2-[(6-cyanopyridin-2-yl)(methyl)amino]ethyl}-N-
ethyl-2-(2H-1,2,3-triazol-2-yl)benzamide;
{2-[(4-cyanopyridin-2-yl)(methyl)amino]ethyl}-N-ethyl-
2-(trifluoromethoxy)benzamide;
N-{2-[(4-cyanopyridin-2-yl)(methyl)amino]ethyl}-N-
ethyl-2-(1H-tetrazol-5-yl)benzamide;
2-(benzyloxy)-N-{2-[(4-cyanopyridin-2-yl)(methyl)
amino]ethyl}-N-ethylpyridine-3-carboxamide;
N-{2-[(4-cyanopyridin-2-yl)(methyl)amino]ethyl}-N-
ethyl-2-phenoxypyridine-3-carboxamide;
N-{2-[(4-cyanopyridin-2-yl)(methyl)amino]ethyl}-N-
ethyl-2-(trifluoromethyl)pyridine-3-carboxamide;
N-{2-[(4-cyanopyridin-2-yl)(methyl)amino]ethyl}-N-
ethyl-2-(1H-imidazol-1-yl)benzamide;
N-{2-[(4-cyanopyridin-2-yl)(methyl)amino]ethyl}-2-(4-
cyanotetrahydro-2H-pyran-4-yl)-N-ethylbenzamide;
N-{2-[(4-cyanopyridin-2-yl)(methyl)amino]ethyl}-N-
ethyl-2-pyrazin-2-ylbenzamide;
N-{2-[(4-cyanopyridin-2-yl)(methyl)amino]ethyl}-N-
ethyl-2-(1H-pyrazol-1-yl)benzamide;
N-{2-[(4-cyanopyridin-2-yl)(methyl)amino]ethyl}-N-
ethyl-2-(2-fluoroethoxy)benzamide;
N-{2-[(4-cyanopyridin-2-yl)(methyl)amino]ethyl}-N-
ethyl-2-(2,2,2-trifluoroethoxy)-benzamide;
N-{2-[(4-cyanopyridin-2-yl)(methyl)amino]ethyl}-N-
ethyl-2-fluoro-6-(2H-1,2,3-triazol-2-yl)benzamide;
N-{2-[(4-cyanopyridin-2-yl)(methyl)amino]ethyl}-N-
ethyl-2-(methoxymethyl)benzamide;
N-{2-[(4-cyanopyridin-2-yl)(methyl)amino]ethyl}-N-
ethyl-2-fluoro-6-(1H-1,2,3-triazol-1-yl)benzamide;
N-{2-[(4-cyanopyridin-2-yl)(methyl)amino]ethyl}-N-
ethyl-2-oxo-2,3-dihydro-1,3-benzoxazole-7-carbox-
amide;
N-{2-[(4-cyanopyridin-2-yl)(methyl)amino]ethyl}-2-
ethoxy-N-ethyl-1H-benzimidazole-7-carboxamide;
N-{2-[(4-cyanopyridin-2-yl)(methyl)amino]ethyl}-N-
ethyl-5-methyl-2-(2H-1,2,3-triazol-2-yl)benzamide;
N-{2-[(4-cyanopyridin-2-yl)(methyl)amino]ethyl}-N-
ethyl-2-(4-methyl-1H-1,2,3-triazol-1-yl)benzamide;
N-{2-[(4-cyanopyridin-2-yl)(methyl)amino]ethyl}-N-
ethyl-2-pyrrolidin-1-ylbenzamide;
N-{2-[(4-cyanopyridin-2-yl)(methyl)amino]ethyl}-N-
ethyl-2-oxo-2,3-dihydro-1,3-benzoxazole-4-carbox-
amide;
N-{2-[(4-cyanopyridin-2-yl)(methyl)amino]ethyl}-N-
ethyl-2-(1H-imidazol-2-yl)benzamide;
N-{2-[(4-cyanopyridin-2-yl)(methyl)amino]ethyl}-N-
ethyl-2-(1H-tetrazol-1-yl)benzamide;
2(1-cyanocyclopropyl)-N-{2-[(4-cyanopyridin-2-yl)
(methyl)amino]ethyl}-N-ethylbenzamide;
N-{2-[(4-cyanopyridin-2-yl)(methyl)amino]ethyl}-N-
ethyl-2-(3-methyl-1,2,4-oxadiazol-5-yl)benzamide;
N-{2-[(4-cyanopyridin-2-yl)(methyl)amino]ethyl}-N-
ethyl-2-(1H-1,2,3-triazol-1-yl)benzamide;
N-{2-[(4-cyanopyridin-2-yl)(methyl)amino]ethyl}-3-
ethoxy-N-ethyl-2-methoxybenzamide;
N-{2-[(4-cyanopyridin-2-yl)(methyl)amino]ethyl}-N-
ethyl-5-fluoro-2-(2H-1,2,3-triazol-2-yl)benzamide;
N-{2-[(4-cyanopyridin-2-yl)(methyl)amino]ethyl}-N-
ethyl-6-(2,2,2-trifluoroethoxy)pyridine-3-carboxam-
ide;
N-(2-((4-cyanopyridin-2-yl)(methyl)amino)ethyl)-N-
methyl-2-(2H-1,2,3-triazol-2-yl)benzamide;
N-(2-((4-cyanopyridin-2-yl)(methyl)amino)ethyl)-N-pro-
pyl-2-(2H-1,2,3-triazol-2-yl)benzamide;
N-butyl-N-(2-((4-cyanopyridin-2-yl)(methyl)amino)
ethyl)-2-(2H-1,2,3-triazol-2-yl)benzamide;
N-benzyl-N-(2-((4-cyanopyridin-2-yl)(methyl)amino)
ethyl)-2-(2H-1,2,3-triazol-2-yl)benzamide;
N-(2-((4-cyanopyridin-2-yl)(methyl)amino)ethyl)-N-(cy-
clopropylmethyl)-2-(2H-1,2,3-triazol-2-yl)benzamide;
N-(2-((4-cyanopyridin-2-yl)(methyl)amino)ethyl)-N-
isobutyl-2-(2H-1,2,3-triazol-2-yl)benzamide
N-(2-((4-cyanopyridin-2-yl)(methyl)amino)ethyl)-N-iso-
propyl-2-(2H-1,2,3-triazol-2-yl)benzamide;
N-(2-((4-cyanopyridin-2-yl)(methyl)amino)ethyl)-2-(2H-
1,2,3-triazol-2-yl)-N-(2,2,2-trifluoroethyl)benzamide;
N-ethyl-N-(2-((4-(2-hydroxypropan-2-yl)pyrimidin-2-yl)
(methyl)amino)ethyl)-2-(2H-1,2,3-triazol-2-yl)benz-
amide;
N-ethyl-N-(2-((4-(2-hydroxypropan-2-yl)pyrimidin-2-yl)
(methyl)amino)ethyl)-2-isopropoxynicotinamide;
2-ethoxy-N-ethyl-N-(2-((4-(2-hydroxypropan-2-yl)py-
rimidin-2-yl)(methyl)amino)ethyl)-nicotinamide;
2-(2,2-difluoroethoxy)-N-ethyl-N-(2-((4-(2-hydroxypro-
pan-2-yl)pyrimidin-2-yl)(methyl)amino)ethyl)nicoti-
namide;
2-(2,2-difluoroethoxy)-N-ethyl-N-(2-((4-(2-hydroxypro-
pan-2-yl)pyrimidin-2-yl)(methyl)amino)ethyl)nicoti-
namide;
2-(difluoromethoxy)-N-ethyl-N-(2-((4-(2-hydroxypro-
pan-2-yl)pyrimidin-2-yl)(methyl)amino)ethyl)benz-
amide;
N-ethyl-N-(2-((4-(2-hydroxypropan-2-yl)pyrimidin-2-yl)
(methyl)amino)ethyl)-2-propylbenzamide;
N-ethyl-N-(2-((4-(2-hydroxypropan-2-yl)pyrimidin-2-yl)
(methyl)amino)ethyl)-2-(2,2,2-trifluoroethoxy)benz-
amide;
N-ethyl-N-(2-((4-(2-hydroxypropan-2-yl)pyrimidin-2-yl)
(methyl)amino)ethyl)-2-(2,2,2-trifluoroethyl)benz-
amide;
2-(2,2-difluoroethoxy)-N-ethyl-N-(2-((4-(2-hydroxypro-
pan-2-yl)pyrimidin-2-yl)(methyl)amino)ethyl)benz-
amide;
N-ethyl-N-(2-((4-(2-hydroxypropan-2-yl)pyrimidin-2-yl)
(methyl)amino)ethyl)-2-(2,2,2-trifluoroethyl)nicotina-
mide;
2-(2,2-difluoroethyl)-N-ethyl-N-(2-((4-(2-hydroxypro-
pan-2-yl)pyrimidin-2-yl)(methyl)amino)ethyl)benz-
amide;
2-cyclopropyl-N-ethyl-N-(2-((4-(2-hydroxypropan-2-yl)
pyrimidin-2-yl)(methyl)amino)ethyl)benzamide;
2-(2,2-difluorocyclopropyl)-N-ethyl-N-(2-((4-(2-hy-
droxypropan-2-yl)pyrimidin-2-yl)(methyl)amino)
ethyl)benzamide;
N-ethyl-N-(2-((4-(2-hydroxypropan-2-yl)pyrimidin-2-yl)
(methyl)amino)ethyl)-2-(trifluoromethoxy)benzamide;
2-cyclopropyl-N-ethyl-N-(2-((4-(2-hydroxypropan-2-yl)
pyrimidin-2-yl)(methyl)amino)ethyl)-6-methoxynico-
tinamide;

N-ethyl-N-(2-((4-(2-hydroxypropan-2-yl)pyrimidin-2-yl)(methyl)amino)ethyl)-2-(2H-tetrazol-2-yl)benzamide;
N-ethyl-N-(2-((4-(2-hydroxypropan-2-yl)pyrimidin-2-yl)(methyl)amino)ethyl)-2-phenylnicotinamide;
N-ethyl-N-(2-((4(4-(2-hydroxypropan-2-yl)pyrimidin-2-yl)(methyl)amino)ethyl)-3-phenylpicolinamide;
N-ethyl-N-(2-((4(4-(2-hydroxypropan-2-yl)pyrimidin-2-yl)(methyl)amino)ethyl)-3-(1H-pyrazol-1-yl)pyrazine-2-carboxamide;
N-ethyl-N-[2-[[4-(1-hydroxy- 1-methyl-ethyl)pyrimidin-2-yl]-methyl-amino]ethyl]-2-pyrazol-1-yl-pyridine-3-carboxamide;
N-ethyl-N-[2-[[4-(1-hydroxy- 1-methyl-ethyl)pyrimidin-2-yl]-methyl-amino]ethyl]-3 -(triazol-2-yl)pyridine-2-carboxamide;
N-ethyl-N-(2-((6-(2-hydroxypropan-2-yl)pyridin-2-yl)(methyl)amino)ethyl)-2-(2H-1,2,3-triazol-2-yl)benzamide;
2-(2,2-difluoroethoxy)-N-ethyl-N-(2-((6-(2-hydroxypropan-2-yl)pyridin-2-yl)(methyl)amino)ethyl)benzamide;
N-ethyl-N-(2-((6-(2-hydroxypropan-2-yl)pyridin-2-yl)(methyl)amino)ethyl)-3-(2H-1,2,3-triazol-2-yl)picolinamide;
N-ethyl-N-(2-((6-(2-hydroxypropan-2-yl)pyridin-2-yl)(methyl)amino)ethyl)-2-(1H-pyrazol-1-yl)benzamide;
N-ethyl-N-(2-((6-(2-hydroxypropan-2-yl)pyridin-2-yl)(methyl)amino)ethyl)-3-(1H-pyrazol-1-yl)pyrazine-2-carboxamide;
N-ethyl-N-(2-((6-(2-hydroxypropan-2-yl)pyridin-2-yl)(methyl)amino)ethyl)-2-(trifluoromethoxy)benzamide;
2-cyclopropyl-N-ethyl-N-(2-((6-(2-hydroxypropan-2-yl)pyridin-2-yl)(methyl)amino)ethyl)benzamide;
2-(difluoromethoxy)-N-ethyl-N-(2-((6-(2-hydroxypropan-2-yl)pyridin-2-yl)(methyl)amino)ethyl)benzamide;
N-ethyl-N-(2-((6-(2-hydroxypropan-2-yl)pyridin-2-yl)(methyl)amino)ethyl)-2-(2,2,2-trifluoroethoxy)nicotinamide;
2-(2,2-difluoroethoxy)-N-ethyl-N-(2-((6-(2-hydroxypropan-2-yl)pyridin-2-yl)(methyl)amino)ethyl)nicotinamide;
N-ethyl-N-(2-((6-(2-hydroxypropan-2-yl)pyridin-2-yl)(methyl)amino)ethyl)-2-(2,2,2-trifluoroethoxy)benzamide;
2-ethoxy-N-ethyl-N-(2-((6-(2-hydroxypropan-2-yl)pyridin-2-yl)(methyl)amino)ethyl)benzamide;
N-ethyl-N-(2-((6-(2-hydroxypropan-2-yl)pyridin-2-yl)(methyl)amino)ethyl)-2-(2,2,2-trifluoroethyl)nicotinamide;
2-(2,2-difluorocyclopropyl)-N-ethyl-N-(2-((6-(2-hydroxypropan-2-yl)pyridin-2-yl)(methyl)amino)ethyl)benzamide;
N-ethyl-N-(2-((6-(2-hydroxypropan-2-yl)pyridin-2-yl)(methyl)amino)ethyl)-2-isopropoxynicotinamide;
N-ethyl-N-(2-((6-(2-hydroxypropan-2-yl)pyridin-2-yl)(methyl)amino)ethyl)-3-phenylpicolinamide;
N-ethyl-N-(2-((6-(2-hydroxypropan-2-yl)pyridin-2-yl)(methyl)amino)ethyl)-2-(2H-tetrazol-2-yl)benzamide;
N-ethyl-N-(2-((6-(2-hydroxypropan-2-yl)pyridin-2-yl)(methyl)amino)ethyl)-2-(1H-pyrazol-1-yl)nicotinamide; and
2-ethoxy-N-ethyl-N-(2-((6-(2-hydroxypropan-2-yl)pyridin-2-yl)(methyl)amino)ethyl)nicotinamide;
or a pharmaceutically acceptable salt thereof.

9. A pharmaceutical composition which comprises an inert carrier and a compound of claim 1 or a pharmaceutically acceptable salt thereof.

10. A method for treating insomnia in a mammalian patient in need thereof which comprises administering to the patient a therapeutically effective amount of the compound of claim 1 or a pharmaceutically acceptable salt thereof.

* * * * *